US012653888B2

(12) United States Patent
Bandukwala et al.

(10) Patent No.: US 12,653,888 B2
(45) Date of Patent: Jun. 16, 2026

(54) COMPOSITIONS, DEVICES AND METHODS FOR INDUCING IMMUNE RESPONSES TO INFECTIOUS AGENTS

(71) Applicant: SIGILON THERAPEUTICS, INC., Cambridge, MA (US)

(72) Inventors: Hozefa Bandukwala, Southborough, MA (US); David E. Moller, Newton, MA (US); David Peritt, Skokie, IL (US)

(73) Assignee: SIGILON THERAPEUTICS, INC., Cambridge, MA (US)

( * ) Notice: Subject to any disclaimer, the term of this patent is extended or adjusted under 35 U.S.C. 154(b) by 615 days.

(21) Appl. No.: 17/923,283

(22) PCT Filed: May 4, 2021

(86) PCT No.: PCT/US2021/030725
§ 371 (c)(1),
(2) Date: Nov. 4, 2022

(87) PCT Pub. No.: WO2021/226137
PCT Pub. Date: Nov. 11, 2021

(65) Prior Publication Data

US 2023/0233679 A1 Jul. 27, 2023

Related U.S. Application Data

(60) Provisional application No. 63/019,825, filed on May 4, 2020.

(51) Int. Cl.

| | |
|---|---|
| ***A61K 39/00*** | (2006.01) |
| ***A61K 9/00*** | (2006.01) |
| ***A61K 9/06*** | (2006.01) |
| ***A61K 9/48*** | (2006.01) |
| ***A61K 39/155*** | (2006.01) |
| ***A61K 39/21*** | (2006.01) |
| ***A61K 39/215*** | (2006.01) |
| ***A61K 39/245*** | (2006.01) |
| ***A61K 39/39*** | (2006.01) |
| ***A61K 40/34*** | (2025.01) |
| ***A61K 40/35*** | (2025.01) |

(52) U.S. Cl.
CPC ............ *A61K 40/34* (2025.01); *A61K 9/0024* (2013.01); *A61K 9/06* (2013.01); *A61K 9/4808* (2013.01); *A61K 9/4866* (2013.01); *A61K 39/155* (2013.01); *A61K 39/21* (2013.01); *A61K 39/215* (2013.01); *A61K 39/245* (2013.01); *A61K 39/39* (2013.01); *A61K 40/35* (2025.01); *A61K 2039/5156* (2013.01); *A61K 2039/55522* (2013.01)

(58) Field of Classification Search
CPC ...... A61K 2039/55522; A61K 47/6957; A61K 39/12; A61K 39/215; A61K 39/39
See application file for complete search history.

(56) References Cited

U.S. PATENT DOCUMENTS

2004/0005302 A1 1/2004 Hortelano

FOREIGN PATENT DOCUMENTS

WO 2004/092360 A2 10/2004
WO 2019/195055 A1 10/2019

OTHER PUBLICATIONS

International search report and written opinion for application No. PCT/US2021/030725 mailed Oct. 22, 2021.

*Primary Examiner* — Barry A Chestnut
(74) *Attorney, Agent, or Firm* — Quarles & Brady, LLP

(57) ABSTRACT

Described herein are implantable devices comprising cells engineered to express and secrete antigens of infectious agents. The devices are useful for inducing protective immune responses against infectious agents.

22 Claims, 14 Drawing Sheets

Specification includes a Sequence Listing.

Surface glycoprotein (SEQ ID NO:2)

```
   1 MFVFLVLLPL VSSQCVNLTT RTQLPPAYTN SFTRGVYYPD KVFRSSVLHS TQDLFLPFFS
  61 NVTWFHAIHV SGTNGTKRFD NPVLPFNDGV YFASTEKSNI IRGWIFGTTL DSKTQSLLIV
 121 NNATNVVIKV CEFQFCNDPF LGVYYHKNNK SWMESEFRVY SSANNCTFEY VSQPFLMDLE
 181 GKQGNFKNLR EFVFKNIDGY FKIYSKHTPI NLVRDLPQGF SALEPLVDLP IGINITRFQT
 241 LLALHRSYLT PGDSSSGWTA GAAAYYVGYL QPRTFLLKYN ENGTITDAVD CALDPLSETK
 301 CTLKSFTVEK GIYQTSNFRV QPTESIVRFP NITNLCPFGE VFNATRFASV YAWNRKRISN
 361 CVADYSVLYN SASFSTFKCY GVSPTKLNDL CFTNVYADSF VIRGDEVRQI APGQTGKIAD
 421 YNYKLPDDFT GCVIAWNSNN LDSKVGGNYN YLYRLFRKSN LKPFERDIST EIYQAGSTPC
 481 NGVEGFNCYF PLQSYGFQPT NGVGYQPYRV VVLSFELLHA PATVCGPKKS TNLVKNKCVN
 541 FNFNGLTGTG VLTESNKKFL PFQQFGRDIA DTTDAVRDPQ TLEILDITPC SFGGVSVITP
 601 GTNTSNQVAV LYQDVNCTEV PVAIHADQLT PTWRVYSTGS NVFQTRAGCL IGAEHVNNSY
 661 ECDIPIGAGI CASYQTQTNS PRRARSVASQ SIIAYTMSLG AENSVAYSNN SIAIPTNFTI
 721 SVTTEILPVS MTKTSVDCTM YICGDSTECS NLLLQYGSFC TQLNRALTGI AVEQDKNTQE
 781 VFAQVKQIYK TPPIKDFGGF NFSQILPDPS KPSKRSFIED LLFNKVTLAD AGFIKQYGDC
 841 LGDIAARDLI CAQKFNGLTV LPPLLTDEMI AQYTSALLAG TITSGWTFGA GAALQIPFAM
 901 QMAYRFNGIG VTQNVLYENQ KLIANQFNSA IGKIQDSLSS TASALGKLQD VVNQNAQALN
 961 TLVKQLSSNF GAISSVLNDI LSRLDKVEAE VQIDRLITGR LQSLQTYVTQ QLIRAAEIRA
1021 SANLAATKMS ECVLGQSKRV DFCGKGYHLM SFPQSAPHGV VFLHVTYVPA QEKNFTTAPA
1081 ICHDGKAHFP REGVFVSNGT HWFVTQRNFY EPQIITTDNT FVSGNCDVVI GIVNNTVYDP
1141 LQPELDSFKE ELDKYFKNHT SPDVDLGDIS GINASVVNIQ KEIDRLNEVA KNLNESLIDL
1201 QELGKYEQYI KWPWYIWLGF IAGLIAIVMV TIMLCCMTSC CSCLKGCCSC GSCCKFDEDD
1261 SEPVLKGVKL HYT
```

FIG. 1A

Nsp3 (SEQ ID NO:3)

```
   1 APTKVTFGDD TVIEVQGYKS VNITFELDER IDKVLNEKCS AYTVELGTEV NEFACVVADA
  61 VIKTLQPVSE LLTPLGIDLD EWSMATYYLF DESGEFKLAS HMYCSFYPPD EDEEEGDCEE
 121 EEFEPSTQYE YGTEDDYQGK PLEFGATSAA LQPEEEQEED WLDDDSQQTV GQQDGSEDNQ
 181 TTTIQTIVEV QPQLEMELTP VVQTIEVNSF SGYLKLTDNV YIKNADIVEE AKKVKPTVVV
 241 NAANVYLKHG GGVAGALNKA TNNAMQVESD DYIATNGPLK VGGSCVLSGH NLAKHCLHVV
 301 GPNVNKGEDI QLLKSAYENF NQHEVLLAPL LSAGIFGADP IHSLRVCVDT VRTNVYLAVF
 361 DKNLYDKLVS SFLEMKSEKQ VEQKIAEIPK EEVKPFITES KPSVEQRKQD DKKIKACVEE
 421 VTTTLEETKF LTENLLLYID INGNLHPDSA TLVSDIDITF LKKDAPYIVG DVVQEGVLTA
 481 VVIPTKKAGG TTEMLAKALR KVPTDNYITT YPGQGLNGYT VEEAKTVLKK CKSAFYILPS
 541 IISNEKQEIL GTVSWNLREM LAHAEETRKL MPVCVETKAI VSTIQRKYKG IKIQEGVVDY
 601 GARFYFYTSK TTVASLINTL NDLNETLVTM PLGYVTHGLN LEEAARYMRS LKVPATVSVS
 661 SPDAVTAYNG YLTSSSKTPE EHFIETISLA GSYKDWSYSG QSTQLGIEFL KRGDKSVYYT
 721 SNPTTFHLDG EVITFDNLKT LLSLREVRTI KVFTTVDNIN LHTQVVDMSM TYGQQFGPTY
 781 LDGADVTKIK PHNSHEGKTF YVLPNDDTLR VEAFEYYHTT DPSFLGRYMS ALNHTKKWKY
 841 PQVNGLTSIK WADNNCYLAT ALLTLQQIEL KFNPPALQDA YYRARAGEAA NFCALILAYC
 901 NKTVGELGDV RETMSYLFQH ANLDSCKRVL NVVCKTCGQQ QTTLKGVEAV MYMGTLSYEQ
 961 FKKGVQIPCT CGKQATKYLV QQESPFVMMS APPAQYELKH GTFTCASEYT GNYQCGHYKH
1021 ITSKETLYCI DGALLTKSSE YKGPITDVFY KENSYTTTIK PVTYKLDGVV CTEIDPKLDN
1081 YYKKDNSYFT EQPIDLVPNQ PYPNASFDNF KFVCDNIKFA DDLNQLTGYK KPASRELKVT
1141 FFPDLNGDVV AIDYKHYTPS FKKGAKLLHK PIVWHVNNAT NKATYKPNTW CIRCLWSTKP
1201 VETSNSFDVL KSEDAQGMDN LACEDLKPVS EEVVENPTIQ KDVLECNVKT TEVVGDIILK
1261 PANNSLKITE EVGHTDLMAA YVDNSSLTIK KPNELSRVLG LKTLATHGLA AVNSVPWDTI
1321 ANYAKPFLNK VVSTTTNIVT RCLNRVCTNY MPYFFTLLLQ LCTFTRSTNS RIKASMPTTI
1381 AKNTVKSVGK FCLEASFNYL KSPNFSKLIN IIIWFLLLSV CLGSLIYSTA ALGVLMSNLG
1441 MPSYCTGYRE GYLNSTNVTI ATYCTGSIPC SVCLSGLDSL DTYPSLETIQ ITISSFKWDL
1501 TAFGLVAEWF LAYILFTRFF YVLGLAAIMQ LFFSYFAVHF ISNSWLMWLI INLVQMAPIS
1561 AMVRMYIFFA SFYYVWKSYV HVVDGCNSST CMMCYKRNRA TRVECTTIVN GVRRSFYVYA
1621 NGGKGFCKLH NWNCVNCDTF CAGSTFISDE VARDLSLQFK RPINPTDQSS YIVDSVTVKN
1681 GSIHLYFDKA GQKTYERHSL SHFVNLDNLR ANNTKGSLPI NVIVFDGKSK CEESSAKSAS
1741 VYYSQLMCQP ILLLDQALVS DVGDSAEVAV KMFDAYVNTF SSTFNVPMEK LKTLVATAEA
1801 ELAKNVSLDN VLSTFISAAR QGFVDSDVET KDVVECLKLS HQSDIEVTGD SCNNYMLTYN
1861 KVENMTPRDL GACIDCSARH INAQVAKSHN IALIWNVKDF MSLSEQLRKQ IRSAAKKNNL
1921 PFKLTCATTR QVVNVVTTKI ALKGG
```

FIG. 1B

Nsp8 (SEQ ID NO:4)

```
  1 AIASEFSSLP SYAAFATAQE AYEQAVANGD SEVVLKKLKK SLNVAKSEFD RDAAMQRKLE
 61 KMADQAMTQM YKQARSEDKR AKVTSAMQTM LFTMLRKLDN DALNNIINNA RDGCVPLNII
121 PLTTAAKLMV VIPDYNTYKN TCDGTTFTYA SALWEIQQVV DADSKIVQLS EISMDNSPNL
181 AWPLIVTALR ANSAVKLQ
```

FIG. 1C

Nsp9 (SEQ ID NO:5)

```
  1 NNELSPVALR QMSCAAGTTQ TACTDDNALA YYNTTKGGRF VLALLSDLQD LKWARFPKSD
 61 GTGTIYTELE PPCRFVTDTP KGPKVKYLYF IKGLNNLNRG MVLGSLAATV RLQ
```

FIG. 1D

Nsp10 (SEQ ID NO:6)

```
  1 AGNATEVPAN STVLSFCAFA VDAAKAYKDY LASGGQPITN CVKMLCTHTG TGQAITVTPE
 61 ANMDQESFGG ASCCLYCRCH IDHPNPKGFC DLKGKYVQIP TTCANDPVGF TLKNTVCTVC
121 GMWKGYGCSC DQLREPMLQ
```

FIG. 1E

3CL protease (SEQ ID NO:7)

```
  1 SGFRKMAFPS GKVEGCMVQV TCGTTTLNGL WLDDVVYCPR HVICTSEDML NPNYEDLLIR
 61 KSNHNFLVQA GNVQLRVIGH SMQNCVLKLK VDTANPKTPK YKFVRIQPGQ TFSVLACYNG
121 SPSGVYQCAM RPNFTIKGSF LNGSCGSVGF NIDYDCVSFC YMHHMELPTG VHAGTDLEGN
181 FYGPFVDRQT AQAAGTDTTI TVNVLAWLYA AVINGDRWFL NRFTTTLNDF NLVAMKYNYE
241 PLTQDHVDIL GPLSAQTGIA VLDMCASLKE LLQNGMNGRT ILGSALLEDE FTPFDVVRQC
301 SGVTFQ
```

FIG. 1F

Nucleocapsid phosphoprotein (SEQ ID NO:8)

```
  1 MSDNGPQNQR NAPRITFGGP SDSTGSNQNG ERSGARSKQR RPQGLPNNTA SWFTALTQHG
 61 KEDLKFPRGQ GVPINTNSSP DDQIGYYRRA TRRIRGGDGK MKDLSPRWYF YYLGTGPEAG
121 LPYGANKDGI IWVATEGALN TPKDHIGTRN PANNAAIVLQ LPQGTTLPKG FYAEGSRGGS
181 QASSRSSSRS RNSSRNSTPG SSRGTSPARM AGNGGDAALA LLLLDRLNQL ESKMSGKGQQ
241 QQGQTVTKKS AAEASKKPRQ KRTATKAYNV TQAFGRRGPE QTQGNFGDQE LIRQGTDYKH
301 WPQIAQFAPS ASAFFGMSRI GMEVTPSGTW LTYTGAIKLD DKDPNFKDQV ILLNKHIDAY
361 KTFPPTEPKK DKKKADETQ ALPQRQKKQQ TVTLLPAADL DDFSKQLQQS MSSADSTQA
```

FIG. 1G

327c SOSIP (SEQ ID NO:9)

```
  1 MGNLWVTVYY GVPVWKEAKT TLFCASDAKA YEQEVHNVWA THACVPTDPN PQEMRMENVT
 61 ENFNMWKNDM VDQMHEDIIS LWDQSLKPCV KLTPLCVTLD CQNVNATQNT NDTISTMKNC
121 TFNTTADLGD KKQKGRALFY NLDIVQLNPN SNSSEYRLIS CNTSTITQAC PKVSFEPIPI
181 HYCAPAGYAI LKCNNKTFNG LGPCTNVSTV QCTHGIKPVV STQLLLNGSL AEGEIIIRSE
241 NLTDNGKTII VHLNESVKIV CIRPNNNTRK SIRIGPGQTF FATDIIGDIR QAYCNISRED
301 WNKTLDRVRK KLEEHFPNKT IEFKRHSGGD LEVTQHSFNC RGEFFYCNTT HLFENTTYTN
361 SSNITLPCRI KQIINMWQGV GRAMYAPPIA GNITCISNIT GILLTRDGGN NGTNETFRPG
421 GGDMRDNWRS ELYKYKVVEI KPLGIAPTKC KRRVVERRRR RRAVGMGALF LGFLGAAGST
481 MGAASMTLTV QARQLLSGIV QQQSNLLRAP EAQQHMLQLT VWGIKQLQAR VLALERYLQD
541 QQLLGIWGCS GKLICCTAVP WNSSWSNKTY NDIWDNMTWM QWEREISNYT NTIYTLLEVS
601 QNQQEQNEKD LLALDRQAYC NISREDWNKT LDRVRKKLEE HFPNKTIEFK RHSGGDLEVT
661 QHSFNCRGEF FYCNTTHLFE NTTYTNSSNI TLPCRIKQII NMWQGVGRAM YAPPIAGNIT
721 CISNITGILL TRDGGNNGTN ETFRPGGGDM RDNWRSELYK YKVVEIKPLG IAPTKCKRRV
781 VERRRRRRAV GMGALFLGFL GAAGSTMGAA SMTLTVQARQ LLSGIVQQQS NLLRAPEAQQ
841 HMLQLTVWGI KQLQARVLAL ERYLQDQQLL GIWGCSGKLI CCTAVPWNSS WSNKTYNDIW
901 DNMTWMQWER EISNYTNTIY TLLEVSQNQQ EQNEKDLLAL D
```

FIG. 2A

327c MD377 (SEQ ID NO:10)

```
  1 MGNLWVTVYY GVPVWKEAKT TLFCASDAKA YEQEVHNVWA THACVPTDPN PQEMRMENVT
 61 ENFNMWKNDM VDQMHEDIIS LWDQSLKPCC KLTPLCVTLD CQNVNATQNT NDTISTMKNC
121 TFNTTADLGD KKQKGRALFY NLDIVQLNPN SNSSEYRLIS CNTSTCTQAC PKVSFEPIPI
181 HYCAPAGYAI LKCNNKTFNG LGPCTNVSTV QCTHGIKPVV STQLLLNGSL AEGEIIIRSE
241 NLTDNGKTII VHLNESVKIV CIRPNNNTRK SIRIGPGCTF FATDIIGDIR QAYCNISRED
301 WNKTLDRVRK KLEEHFPNKT IEFKQHSGGD LEVTQHSFNC RGEFFYCNTT HLFENTTYTN
361 SSNITLPCRI KQIINMWQGV GRCMYAPPIA GNITCISNIT GILLTRDGGN NGTNETFRPG
421 GGDMRDNWRS ELYKYKVVEI KPLGIAPTKC KRRVVERRRR RRAVGMGALS LGFLGAAGST
481 MGAASMTLTV QARQLLSGIV QQQSNLLRAP EPQEHMHQDT HWGIKQLQAR VLALEHYLQD
541 QQLLGIWGCS GKLICCTAVP WNSSWSNKTY NDIWDNMTWM QWEREISNYT NTIYTLLEVS
601 QNQQEQNEKD LLALD
```

FIG. 2B

327c MD39 (SEQ ID NO:11)

```
  1 MGNLWVTVYY GVPVWKEAKT TLFCASDAKA YEQEVHNVWA THACVPTDPN PQEMRMENVT
 61 ENFNMWKNDM VDQMHEDIIS LWDQSLKPCV KLTPLCVTLD CQNVNATQNT NDTISTMKNC
121 TFNTTADLGD KKQKGRALFY NLDIVQLNPN SNSSEYRLIS CNTSTITQAC PKVSFEPIPI
181 HYCAPAGYAI LKCNNKTFNG LGPCTNVSTV QCTHGIKPVV STQLLLNGSL AEGEIIIRSE
241 NLTDNGKTII VHLNESVKIV CIRPNNNTVK SIRIGPGQTF FYTDIIGDIR QAYCNISRED
301 WNKTLDRVRK KLEEHFPNKT IEFKQHSGGD LEVTQHSFNC RGEFFYCNTT HLFENTTYTN
361 SSNITLPCRI KQIINMWQGV GRAMYAPPIA GNITCISNIT GILLTRDGGN NGTNETFRPG
421 GGDMRDNWRS ELYKYKVVEI KPLGIAPTKC KRRVVERRRR RRAVGMGALS LGFLGAAGST
481 MGAASMTLTV QARQLLSGIV QQQSNLLRAP EPQQHMLQDT HWGIKQLQAR VLALEHYLQD
541 QQLLGIWGCS GKLICCTAVP WNSSWSNKTY NDIWDNMTWM QWEREISNYT NTIYTLLEVS
601 QNQQEQNEKD LLALD
```

FIG. 2C

AD8 SOSIP (SEQ ID NO:12)

```
  1 VENLWVTVYY GVPVWKEATT TLFCASDAKA YDTEVHNVWA THACVPTDPN PQEVVLENVT
 61 ENFNMWKNNM VEQMHEDIIS LWDQSLKPCV KLTPLCVTLN CTDLRNVTNI NNSSEGMRGE
121 IKNCSFNITT SIRDKVKKDY ALFYRLDVVP IDNDNTSYRL INCNTSTITQ ACPKVSFEPI
181 PIHYCTPAGF AILKCKDKKF NGTGPCKNVS TVQCTHGIRP VVSTQLLLNG SLAEEEVVIR
241 SSNFTDNAKN IIVQLKESVE INCTRPNNNT RKSIHIGPGR AFYTTGDIIG DIRQAHCNIS
301 RTKWNNTLNQ IATKLKEQFG NNKTIVFNQS SGGDPEIVMH SFNCGGEFFY CNSTQLFNST
361 WNFNGTWNLT QSNGTEGNDT ITLPCRIKQI INMWQEVGKA MYAPPIRGQI RCSSNITGLI
421 LTRDGGNNHN NDTETFRPGG GDMRDNWRSE LYKYKVVKIE PLGVAPTKCK RRVVQRRRRR
481 RAVGTIGAMF LGFLGAAGST MGAASITLTV QARLLLSGIV QQQNNLLRAP EAQQHLLQLT
541 VWGIKQLQAR VLAVERYLRD QQLLGIWGCS GKLICCTAVP WNASWSNKTL DMIWNNMTWM
601 EWEREIDNYT GLIYTLIEES QNQQEKNEQE LLELD
```

FIG. 2D

AD8 MD64 (SEQ ID NO:13)

1 VENLWVTVYY GVPVWKEATT TLFCASDAKA YDTEVHNVWA THECVPTDPN PQEVVLENVT
61 ENFNMWKNNM VEQMHEDIIE LWDQSLKPCV KLTPLCVTLN CTDLRNVTNI NNSSEGMRGE
121 IKNCSFNITT SIRDKVKKDY ALFYRLDVVP IDNDNTSYRL INCNTSTITQ ACPKVSFEPI
181 PIHYCTPAGF AILKCKDKKF NGTGPCKNVS TVQCTHGIRP VVSTQLLLNG SLAEEEVIIR
241 SSNFTDNAKN IIVQLKESVE INCTRPNNNT VKSIHIGPGR AFYYTGDIIG DIRQAHCNIS
301 RTKWNNTLNQ IATKLKEQFG NNKTIVFNQS SGGDPEIVMH SFNCGGEFFY CNSTQLFNST
361 WNFNGTWNLT QSNGTEGNDT ITLPCRIKQI INMWQEVGKA MYAPPIRGQI RCSSNITGLI
421 LTRDGGNNHN NDTETFRPGG GDMRDNWRSE LYKYKVVKIE PLGVAPTKCK RRVVQRRRRR
481 RAVGTIGAMS LGFLGAAGST MGAASITLTV QARLLLSGIV QQQNNLLRAP EPQQHLLQLT
541 VWGIKQLQAR VLAVEHYLRD QQLLGIWGCS GKLICCTAVP WNASWSNKTL DMIWNNMTWM
601 EWEREIDNYT GLIYTLIEES QNQQEKNEQE LLELD

FIG. 2E

BG505 SOSIP (SEQ ID NO:14)

1 AENLWVTVYY GVPVWKDAET TLFCASDAKA YETEKHNVWA THACVPTDPN PQEIHLENVT
61 EEFNMWKNNM VEQMHTDIIS LWDQSLKPCV KLTPLCVTLQ CTNVTNNITD DMRGELKNCS
121 FNMTTELRDK KQKVYSLFYR LDVVQINENQ GNRSNNSNKE YRLINCNTSA ITQACPKVSF
181 EPIPIHYCAP AGFAILKCKD KKFNGTGPCP SVSTVQCTHG IKPVVSTQLL LNGSLAEEEV
241 MIRSENITNN AKNILVQFNT PVQINCTRPN NNTRKSIRIG PGQAFYATGD IIGDIRQAHC
301 NVSKATWNET LGKVVKQLRK HFGNNTIIRF ANSSGGDLEV TTHSFNCGGE FFYCNTSGLF
361 NSTWISNTSV QGSNSTGSND SITLPCRIKQ IINMWQRIGQ AMYAPPIQGV IRCVSNITGL
421 ILTRDGGSTN STTETFRPGG GDMRDNWRSE LYKYKVVKIE PLGVAPTRCK RRVVGRRRRR
481 RAVGIGAVFL GFLGAAGSTM GAASMTLTVQ ARNLLSGIVQ QQSNLLRAPE AQQHLLKLTV
541 WGIKQLQARV LAVERYLRDQ QLLGIWGCSG KLICCTNVPW NSSWSNRNLS EIWDNMTWLQ
601 WDKEISNYTQ IIYGLLEESQ NQQEKNEQDL LALD

FIG. 2F

BG505 MD39 (SEQ ID NO:15)

```
  1 AENLWVTVYY GVPVWKDAET TLFCASDAKA YETEKHNVWA THACVPTDPN PQEIHLENVT
 61 EEFNMWKNNM VEQMHEDIIS LWDQSLKPCV KLTPLCVTLQ CTNVTNNITD DMRGELKNCS
121 FNMTTELRDK KQKVYSLFYR LDVVQINENQ GNRSNNSNKE YRLINCNTSA ITQACPKVSF
181 EPIPIHYCAP AGFAILKCKD KKFNGTGPCP SVSTVQCTHG IKPVVSTQLL LNGSLAEEEV
241 IIRSENITNN AKNILVQLNT PVQINCTRPN NNTVKSIRIG PGQAFYYTGD IIGDIRQAHC
301 NVSKATWNET LGKVVKQLRK HFGNNTIIRF AQSSGGDLEV TTHSFNCGGE FFYCNTSGLF
361 NSTWISNTSV QGSNSTGSND SITLPCRIKQ IINMWQRIGQ AMYAPPIQGV IRCVSNITGL
421 ILTRDGGSTN STTETFRPGG GDMRDNWRSE LYKYKVVKIE PLGVAPTRCK RRVVGRRRRR
481 RAVGIGAVSL GFLGAAGSTM GAASMTLTVQ ARNLLSGIVQ QQSNLLRAPE PQQHLLKDTH
541 WGIKQLQARV LAVEHYLRDQ QLLGIWGCSG KLICCTNVPW NSSWSNRNLS EIWDNMTWLQ
601 WDKEISNYTQ IIYGLLEESQ NQQEKNEQDL LALD
```

FIG. 2G

BG505 MD39.GRSF6 (SEQ ID NO:16)

```
  1 AENLWVTVYY GVPVWKDAET TLFCASDAKA YETEKHNVWA THACVPTDPN SSEIHLENVT
 61 EEFNMWKNNM VEQMHEDIIS LWDQSLKPCV KLTPLCVTLQ CTNVTNNITD DMRGELKNCS
121 FNMTTELRDK KQKVYSLFYR LDVVQINENQ GNRSNNSNKE YRLINCNTSA ITQACPKVSF
181 EPIPIHYCAP AGFAILKCKD KKFNGTGPCQ NVSTVQCTHG IKPVVSTQLL LNGSLAEEEV
241 IIRSENITNN AKNILVQLNT SVQINCTRPN NNTVKSIRIG PGQAFYYTGD IIGDIRQAHC
301 NVSKATWNET LGKVVKQLRK HFGNNTIIRF AQSSGGDLEV TTHSFNCGGE FFYCNTSGLF
361 NSTWISNTSV QGSNSTGSND SITLPCRIKQ IINMWQRIGQ AMYAPPIQGV IRCVSNITGL
421 ILTRDGGSTN STTETFRPGG GDMRDNWRSE LYKYKVVKIE PLGVAPTRCK RRVVGRRRRR
481 RAVGIGAVSL GFLGAAGSTM GAASMTLTVQ ARNLLSGIVQ QQSNLLRAPE PQQHLLKDTH
541 WGIKQLQARV LAVEHYLRDQ QLLGIWGCSG KLICCTNVPW NSSWSNANLS EIWDNMTWLQ
601 WDKEISNYTQ IIYGLLEESQ NQNESNEQDL LALDNGS
```

FIG. 2H

BG505 MD39.GRSF8 (SEQ ID NO:17)

```
  1 AENLWVTVYY GVPVWKDAET TLFCASDAKA YETEKHNVWA THACVPTDPN SSEIHLENVT
 61 EEFNMWKNNM VEQMHEDIIS LWDQSLKPCV KLTPLCVTLQ CTNVTNNITD DMRGELKNCS
121 FNMTTELRDK KQKVYSLFYR LDVVQINENQ GNRSNNSNKE YRLINCNTSA ITQACPKVSF
181 EPIPIHYCAP AGFAILKCKD KKFNGTGPCQ NVSTVQCTHG IKPVVSTQLL LNGSLAEEEV
241 IIRSENITNN AKNILVQLNT SVQINCTRPN NNTVKSIRIG PGQAFYYTGD IIGDIRQAHC
301 NVSKATWNET LGKVVKQLRK HFGNNTIIRF AQSSGGDLEV TTHSFNCGGE FFYCNTSGLF
361 NSTWISNTSV QGSNSTGSND SITLPCRIKQ IINMWQRIGQ AMYAPPIQGV IRCVSNITGL
421 ILTRDGGSTN STTETFRPGG GDMRDNWRSE LYKYKVVKIE PLGVAPTRCK RRVVGRRRRR
481 RAVGIGAVSL GFLGAAGSTM GAASMTLTVQ ARNLLSGIVQ QQSNLLRAPE PQQHLLKDTH
541 WGIKQLQARV LAVEHYLRDQ QLLGIWGCSG KLICCTNVPW NSSWSNRNLS EIWDNMTWLN
601 WSKEISNYTQ IIYGLLEESQ NQQEKNNQSL LALDNGS
```

FIG. 2I

BG505 MD37 (SEQ ID NO:18)

```
  1 AENLWVTVYY GVPVWKDAET TLFCASDAKA YETEKHNVWA THACVPTDPN PQEIHLENVT
 61 EEFNMWKNNM VEQMHEDIIS LWDQSLKPCC KLTPLCVTLQ CTNVTNNITD DMRGELKNCS
121 FNMTTELRDK KQKVYSLFYR LDVVQINENQ GNRSNNSNKE YRLINCNTSA CTQACPKVSF
181 EPIPIHYCAP AGFAILKCKD KKFNGTGPCP SVSTVQCTHG IKPVVSTQLL LNGSLAEEEV
241 IIRSENITNN AKNILVQLNT PVQINCTRPN NNTRKSIRIG PGCAFYATGD IIGDIRQAHC
301 NVSKATWNET LGKVVKQLRK HFGNNTIIRF AQSSGGDLEV TTHSFNCGGE FFYCNTSGLF
361 NSTWISNTSV QGSNSTGSND SITLPCRIKQ IINMWQRIGQ CMYAPPIQGV IRCVSNITGL
421 ILTRDGGSTN STTETFRPGG GDMRDNWRSE LYKYKVVKIE PLGVAPTRCK RRVVGRRRRR
481 RAVGIGAVSL GFLGAAGSTM GAASMTLTVQ ARNLLSGIVQ QQSNLLRAPE PQEHLHKDTH
541 WGIKQLQARV LAVEHYLRDQ QLLGIWGCSG KLICCTNVPW NSSWSNRNLS EIWDNMTWLQ
601 WDKEISNYTQ IIYGLLEESQ NQQEKNEQDL LALD
```

FIG. 2J

BG505 MD64 (SEQ ID NO:19)

```
  1 AENLWVTVYY GVPVWKDAET TLFCASDAKA YETEKHNVWA THECVPTDPN PQEIHLENVT
 61 EEFNMWKNNM VEQMHTDIIE LWDQSLKPCV KLTPLCVTLQ CTNVTNNITD DMRGELKNCS
121 FNMTTELRDK KQKVYSLFYR LDVVQINENQ GNRSNNSNKE YRLINCNTSA ITQACPKVSF
181 EPIPIHYCAP AGFAILKCKD KKFNGTGPCP SVSTVQCTHG IKPVVSTQLL LNGSLAEEEV
241 IIRSENITNN AKNILVQLNT PVQINCTRPN NNTVKSIRIG PGQAFYYTGD IIGDIRQAHC
301 NVSKATWNET LGKVVKQLRK HFGNNTIIRF AQSSGGDLEV TTHSFNCGGE FFYCNTSGLF
361 NSTWISNTSV QGSNSTGSND SITLPCRIKQ IINMWQRIGQ AMYAPPIQGV IRCVSNITGL
421 ILTRDGGSTN STTETFRPGG GDMRDNWRSE LYKYKVVKIE PLGVAPTRCK RRVVGRRRRR
481 RAVGIGAVSL GFLGAAGSTM GAASMTLTVQ ARNLLSGIVQ QQSNLLRAPE PQQHLLKLTV
541 WGIKQLQARV LAVEHYLRDQ QLLGIWGCSG KLICCTNVPW NSSWSNRNLS EIWDNMTWLQ
601 WDKEISNYTQ IIYGLLEESQ NQQEKNEQDL LALD
```

FIG. 2K

BG505 Olio6 (SEQ ID NO:20)

```
  1 AENLWVTVYY GVPVWKDAET TLFCASDAKA YETEKHNVWA THACVPTDPN PQEIHLENVT
 61 EEFNMWKNNM VEQMHEDIIS LWDQSLKPCV KLTPLCVTLQ CTNVTNNITD DMRGELKNCS
121 FNMTTELRDK KQKVYSLFWR LDVVQINENQ GNRSNNSNKE YRLINCNTSA ITQACPKVSF
181 EPIPIHYCAP AGFAILKCKD KKFNGTGPCP SVSTVQCTHG IKPVVSTQLL LNGSLAEEEV
241 IIRSENITNN AKNILVQLNT PVQINCTAPN NFTVKSIRIG PGQAFYYMGD IIGDIRQAHC
301 NVSKATWNET LGKVVKQLRK HFGNNTIIRF AQSSGGDLEV TTHSFNCGGM FFYCNTSGLF
361 NSTWISNTSV QGSNSTGSND SITLPCRIKL IINMWQRIGQ AMYAPPIQGV IRCVSNITGL
421 ILTRDGGSTN STTETFRPGG GDMRDNWRSE LYKYKVVKIE PLGVAPTRCK RRVVGRRRRR
481 RAVGIGAVSL GFLGAAGSTM GAASMTLTVQ ARNLLSGIVQ QQSNLLRAPE PQQHLLKDTH
541 WGIKQLQARV LAVEHYLRDQ QLLGIWGCSG KLICCTNVPW NSSWSNRNLS EIWDNMTWLQ
601 WDKEISNYTQ IIYGLLEESQ NQQEKNEQDL LALD
```

FIG. 2L

BG505 Olio6.CD4KO (SEQ ID NO:21)

```
  1 AENLWVTVYY GVPVWKDAET TLFCASDAKA YETEKHNVWA THACVPTDPN PQEIHLENVT
 61 EEFNMWKNNM VEQMHEDIIS LWDQSLKPCV KLTPLCVTLQ CTNVTNNITD DMRGELKNCS
121 FNMTTELRDK KQKVYSLFWR LDVVQINENQ GNRSNNSNKE YRLINCNTSA ITQACPKVSF
181 EPIPIHYCAP AGFAILKCKD KKFNGTGPCP SVSTVQCTHG IKPVVSTQLL LNGSLAEEEV
241 IIRSENITNN AKNILVQLNT PVQINCTAPN NFTVKSIRIG PGQAFYYMGD IIGDIRQAHC
301 NVSKATWNET LGKVVKQLRK HFGNNTIIRF AQSSGGDLEV TTHSFNCGGM FFYCNTSGLF
361 NSTWISNTSV QGSNSTGSND SITLPCRIKL IINMWQRIGQ AMYAPPIQGV IRCVSNITGL
421 ILTRDGGSTN STTETFRPGG TDMRDNWRSE LYKYKVVKIE PLGVAPTRCK RRVVGRRRRR
481 RAVGIGAVSL GFLGAAGSTM GAASMTLTVQ ARNLLSGIVQ QQSNLLRAPE PQQHLLKDTH
541 WGIKQLQARV LAVEHYLRDQ QLLGIWGCSG KLICCTNVPW NSSWSNRNLS EIWDNMTWLQ
601 WDKEISNYTQ IIYGLLEESQ NQQEKNEQDL LALD
```

FIG. 2M gH (SEQ ID NO:22)

```
  1 MQLLCVFCLV LLWEVGAASL SEVKLHLDIE GHASHYTIPW TELMAKVPGL SPEALWREAN
 61 VTEDLASMLN RYKLIYKTSG TLGIALAEPV DIPAVSEGSM QVDASKVHPG VISGLNSPAC
121 MLSAPLEKQL FYYIGTMLPN TRPHSYVFYQ LRCHLSYVAL SINGDKFQYT GAMTSKFLMG
181 TYKRVTEKGD EHVLSLVFGK TKDLPDLRGP FSYPSLTSAQ SGDYSLVIVT TFVHYANFHN
241 YFVPNLKDMF SRAVTMTAAS YARYVLQKLV LLEMKGGCRE PELDTETLTT MFEVSVAFFK
301 VGHAVGETGN GCVDLRWLAK SFFELTVLKD IIGICYGATV KGMQSYGLER LAAMLMATVK
361 MEELGHLTTE KQEYALRLAT VGYPKAGVYS GLIGGATSVL LSAYNRHPLF QPLHTVMRET
421 LFIGSHVVLR ELRLNVTTQG PNLALYQLLS TALCSALEIG EVLRGLALGT ESGLFSPCYL
481 SLRFDLTRDK LLSMAPQEAT LDQAAVSNAV DGFLGRLSLE REDRDAWHLP AYKCVDRLDK
541 VLMIIPLINV TFIISSDREV RGSALYEAST TYLSSSLFLS PVIMNKCSQG AVAGEPRQIP
601 KIQNFTRTQK SCIFCGFALL SYDEKEGLET TTYITSQEVQ NSILSSNYFD FDNLHVHYLL
661 LTTNGTVMEI AGLYEERAHV VLAIILYFIA FALGIFLVHK IVMFFL
```

FIG. 3A gL (SEQ ID NO:23)

```
  1 MRAVGVFLAI CLVTIFVLPT WGNWAYPCCH VTQLRAQHLL ALENISDIYL VSNQTCDGFS
 61 LASLNSPKNG SNQLVISRCA NGLNVVSFFI SILKRSSSAL TGHLRELLTT LETLYGSFSV
121 EDLFGANLNR YAWHRGG
```

FIG. 3B gp42 (SEQ ID NO:24)

```
  1 MVSFKQVRVP LFTAIALVIV LLLAYFLPPR VRGGGRVAAA AITWVPKPNV EVWPVDPPPP
 61 VNFNKTAEQE YGDKEVKLPH WTPTLHTFQV PQNYTKANCT YCNTREYTFS YKGCCFYFTK
121 KKHTWNGCFQ ACAELYPCTY FYGPTPDILP VVTRNLNAIE SLWVGVYRVG EGNWTSLDGG
181 TFKVYQIFGS HCTYVSKFST VPVSHHECSF LKPCLCVSQR SNS
```

FIG. 3C

Ds-Cav1 + Foldon (SEQ ID NO:25)

```
  1 MELLILKANA ITTILTAVTF CFASGQNITE EFYQSTCSAV SKGYLSALRT GWYTSVITIE
 61 LSNIKENKCN GTDAKVKLIK QELDKYKNAV TELQLLMQST PATNNRARRE LPRFMNYTLN
121 NAKKTNVTLS KKRKRRFLGF LLGVGSAIAS GVAVCKVLHL EGEVNKIKSA LLSTNKAVVS
181 LSNGVSVLTF KVLDLKNYID KQLLPILNKQ SCSISNIETV IEFQQKNNRL LEITREFSVN
241 AGVTTPVSTY MLTNSELLSL INDMPITNDQ KKLMSNNVQI VRQQSYSIMC IIKEEVLAYV
301 VQLPLYGVID TPCWKLHTSP LCTTNTKEGS NICLTRTDRG WYCDNAGSVS FFPQAETCKV
361 QSNRVFCDTM NSLTLPSEVN LCNVDIFNPK YDCKIMTSKT DVSSSVITSL GAIVSCYGKT
421 KCTASNKNRG IIKTFSNGCD YVSNKGVDTV SVGNTLYYVN KQEGKSLYVK GEPIINFYDP
481 LVFPSDEFDA SISQVNEKIN QSLAFIRKSD ELLSAIGGYI PEAPRDGQAY VRKDGEWVLL
541 STFLENLYFQ SSAWSHPQFE KGGGSGGGSG GSAWSHPQFE KGSGSGSGLN DIFEAQKIEW
601 HE
```

FIG. 4A

F + Foldon (SEQ ID NO:26)

```
  1 MELLILKANA ITTILTAVTF CFASGQNITE EFYQSTCSAV SKGYLSALRT GWYTSVITIE
 61 LSNIKKNKCN GTDAKIKLIK QELDKYKNAV TELQLLMQST PATNNRARRE LPRFMNYTLN
121 NAKKTNVTLS KKRKRRFLGF LLGVGSAIAS GVAVSKVLHL EGEVNKIKSA LLSTNKAVVS
181 LSNGVSVLTS KVLDLKNYID KQLLPIVNKQ SCSISNIETV IEFQQKNNRL LEITREFSVN
241 AGVTTPVSTY MLTNSELLSL INDMPITNDQ KKLMSNNVQI VRQQSYSIMS IIKEEVLAYV
301 VQLPLYGVID TPCWKLHTSP LCTTNTKEGS NICLTRTDRG WYCDNAGSVS FFPQAETCKV
361 QSNRVFCDTM NSLTLPSEVN LCNVDIFNPK YDCKIMTSKT DVSSSVITSL GAIVSCYGKT
421 KCTASNKNRG IIKTFSNGCD YVSNKGVDTV SVGNTLYYVN KQEGKSLYVK GEPIINFYDP
481 LVFPSDEFDA SISQVNEKIN QSLAFIRKSD ELLHNVNAVE NLYFQSSAWS HPQFEKGGGS
541 GGGSGGSAWS HPQFEKGSGS GSGLNDIFEA QKIEWHE
```

FIG. 4B fusion glycoprotein F0 (SEQ ID NO:27)

```
  1 MELLILKANA ITTILTAVTF CFASGQNITE EFYQSTCSAV SKGYLSALRT GWYTSVITIE
 61 LSNIKENKCN GTDAKVKLIK QELDKYKNAV TELQLLMQST PPTNNRARRE LPRFMNYTLN
121 NAKKTNVTLS KKRKRRFLGF LLGVGSAIAS GVAVSKVLHL EGEVNKIKSA LLSTNKAVVS
181 LSNGVSVLTS KVLDLKNYID KQLLPIVNKQ SCSISNIETV IEFQQKNNRL LEITREFSVN
241 AGVTTPVSTY MLTNSELLSL INDMPITNDQ KKLMSNNVQI VRQQSYSIMS IIKEEVLAYV
301 VQLPLYGVID TPCWKLHTSP LCTTNTKEGS NICLTRTDRG WYCDNAGSVS FFPQAETCKV
361 QSNRVFCDTM NSLTLPSEIN LCNVDIFNPK YDCKIMTSKT DVSSSVITSL GAIVSCYGKT
421 KCTASNKNRG IIKTFSNGCD YVSNKGMDTV SVGNTLYYVN KQEGKSLYVK GEPIINFYDP
481 LVFPSDEFDA SISQVNEKIN QSLAFIRKSD ELLHNVNAGK STTNIMITTI IIVIIVILLS
541 LIAVGLLLYC KARSTPVTLS KDQLSGINNI AFSN
```

FIG. 4C

SEQUENCE LISTING

<160> NUMBER OF SEQ ID NOS: 40

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Met Gly Trp Arg Ala Ala Gly Ala Leu Leu Leu Ala Leu Leu Leu His
1 5 10 15

Gly Arg Leu Leu Ala
20

<210> SEQ ID NO 2
<211> LENGTH: 1273
<212> TYPE: PRT
<213> ORGANISM: Severe acute respiratory syndrome coronavirus 2

<400> SEQUENCE: 2

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser
245 250 255

Gly Trp Thr Ala Gly Ala Ala Ala Tyr Tyr Val Gly Tyr Leu Gln Pro
260 265 270

Arg Thr Phe Leu Leu Lys Tyr Asn Glu Asn Gly Thr Ile Thr Asp Ala

-continued

```
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700
```

-continued

```
Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                 1015                1020

Leu Ala  Ala Thr Lys Met Ser  Glu Cys Val Leu Gly  Gln Ser Lys
    1025                 1030                1035

Arg Val  Asp Phe Cys Gly Lys  Gly Tyr His Leu Met  Ser Phe Pro
    1040                 1045                1050

Gln Ser  Ala Pro His Gly Val  Val Phe Leu His Val  Thr Tyr Val
    1055                 1060                1065

Pro Ala  Gln Glu Lys Asn Phe  Thr Thr Ala Pro Ala  Ile Cys His
    1070                 1075                1080

Asp Gly  Lys Ala His Phe Pro  Arg Glu Gly Val Phe  Val Ser Asn
    1085                 1090                1095

Gly Thr  His Trp Phe Val Thr  Gln Arg Asn Phe Tyr  Glu Pro Gln
    1100                 1105                1110
```

-continued

```
Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270


<210> SEQ ID NO 3
<211> LENGTH: 1945
<212> TYPE: PRT
<213> ORGANISM: Severe acute respiratory syndrome coronavirus 2

<400> SEQUENCE: 3

Ala Pro Thr Lys Val Thr Phe Gly Asp Asp Thr Val Ile Glu Val Gln
1               5                   10                  15

Gly Tyr Lys Ser Val Asn Ile Thr Phe Glu Leu Asp Glu Arg Ile Asp
            20                  25                  30

Lys Val Leu Asn Glu Lys Cys Ser Ala Tyr Thr Val Glu Leu Gly Thr
        35                  40                  45

Glu Val Asn Glu Phe Ala Cys Val Val Ala Asp Ala Val Ile Lys Thr
    50                  55                  60

Leu Gln Pro Val Ser Glu Leu Leu Thr Pro Leu Gly Ile Asp Leu Asp
65                  70                  75                  80

Glu Trp Ser Met Ala Thr Tyr Tyr Leu Phe Asp Glu Ser Gly Glu Phe
                85                  90                  95

Lys Leu Ala Ser His Met Tyr Cys Ser Phe Tyr Pro Pro Asp Glu Asp
            100                 105                 110

Glu Glu Glu Gly Asp Cys Glu Glu Glu Glu Phe Glu Pro Ser Thr Gln
        115                 120                 125

Tyr Glu Tyr Gly Thr Glu Asp Asp Tyr Gln Gly Lys Pro Leu Glu Phe
    130                 135                 140

Gly Ala Thr Ser Ala Ala Leu Gln Pro Glu Glu Glu Gln Glu Glu Asp
145                 150                 155                 160

Trp Leu Asp Asp Asp Ser Gln Gln Thr Val Gly Gln Gln Asp Gly Ser
                165                 170                 175

Glu Asp Asn Gln Thr Thr Thr Ile Gln Thr Ile Val Glu Val Gln Pro
            180                 185                 190

Gln Leu Glu Met Glu Leu Thr Pro Val Val Gln Thr Ile Glu Val Asn
        195                 200                 205
```

-continued

```
Ser Phe Ser Gly Tyr Leu Lys Leu Thr Asp Asn Val Tyr Ile Lys Asn
    210                 215                 220

Ala Asp Ile Val Glu Glu Ala Lys Lys Val Lys Pro Thr Val Val Val
225                 230                 235                 240

Asn Ala Ala Asn Val Tyr Leu Lys His Gly Gly Gly Val Ala Gly Ala
                245                 250                 255

Leu Asn Lys Ala Thr Asn Asn Ala Met Gln Val Glu Ser Asp Asp Tyr
            260                 265                 270

Ile Ala Thr Asn Gly Pro Leu Lys Val Gly Gly Ser Cys Val Leu Ser
        275                 280                 285

Gly His Asn Leu Ala Lys His Cys Leu His Val Val Gly Pro Asn Val
    290                 295                 300

Asn Lys Gly Glu Asp Ile Gln Leu Leu Lys Ser Ala Tyr Glu Asn Phe
305                 310                 315                 320

Asn Gln His Glu Val Leu Leu Ala Pro Leu Leu Ser Ala Gly Ile Phe
                325                 330                 335

Gly Ala Asp Pro Ile His Ser Leu Arg Val Cys Val Asp Thr Val Arg
            340                 345                 350

Thr Asn Val Tyr Leu Ala Val Phe Asp Lys Asn Leu Tyr Asp Lys Leu
        355                 360                 365

Val Ser Ser Phe Leu Glu Met Lys Ser Glu Lys Gln Val Glu Gln Lys
    370                 375                 380

Ile Ala Glu Ile Pro Lys Glu Glu Val Lys Pro Phe Ile Thr Glu Ser
385                 390                 395                 400

Lys Pro Ser Val Glu Gln Arg Lys Gln Asp Asp Lys Lys Ile Lys Ala
                405                 410                 415

Cys Val Glu Glu Val Thr Thr Thr Leu Glu Glu Thr Lys Phe Leu Thr
            420                 425                 430

Glu Asn Leu Leu Leu Tyr Ile Asp Ile Asn Gly Asn Leu His Pro Asp
        435                 440                 445

Ser Ala Thr Leu Val Ser Asp Ile Asp Ile Thr Phe Leu Lys Lys Asp
    450                 455                 460

Ala Pro Tyr Ile Val Gly Asp Val Val Gln Glu Gly Val Leu Thr Ala
465                 470                 475                 480

Val Val Ile Pro Thr Lys Lys Ala Gly Gly Thr Thr Glu Met Leu Ala
                485                 490                 495

Lys Ala Leu Arg Lys Val Pro Thr Asp Asn Tyr Ile Thr Thr Tyr Pro
            500                 505                 510

Gly Gln Gly Leu Asn Gly Tyr Thr Val Glu Glu Ala Lys Thr Val Leu
        515                 520                 525

Lys Lys Cys Lys Ser Ala Phe Tyr Ile Leu Pro Ser Ile Ile Ser Asn
    530                 535                 540

Glu Lys Gln Glu Ile Leu Gly Thr Val Ser Trp Asn Leu Arg Glu Met
545                 550                 555                 560

Leu Ala His Ala Glu Glu Thr Arg Lys Leu Met Pro Val Cys Val Glu
                565                 570                 575

Thr Lys Ala Ile Val Ser Thr Ile Gln Arg Lys Tyr Lys Gly Ile Lys
            580                 585                 590

Ile Gln Glu Gly Val Val Asp Tyr Gly Ala Arg Phe Tyr Phe Tyr Thr
        595                 600                 605

Ser Lys Thr Thr Val Ala Ser Leu Ile Asn Thr Leu Asn Asp Leu Asn
    610                 615                 620
```

-continued

```
Glu Thr Leu Val Thr Met Pro Leu Gly Tyr Val Thr His Gly Leu Asn
625                 630                 635                 640

Leu Glu Glu Ala Ala Arg Tyr Met Arg Ser Leu Lys Val Pro Ala Thr
                645                 650                 655

Val Ser Val Ser Ser Pro Asp Ala Val Thr Ala Tyr Asn Gly Tyr Leu
            660                 665                 670

Thr Ser Ser Ser Lys Thr Pro Glu Glu His Phe Ile Glu Thr Ile Ser
        675                 680                 685

Leu Ala Gly Ser Tyr Lys Asp Trp Ser Tyr Ser Gly Gln Ser Thr Gln
    690                 695                 700

Leu Gly Ile Glu Phe Leu Lys Arg Gly Asp Lys Ser Val Tyr Tyr Thr
705                 710                 715                 720

Ser Asn Pro Thr Thr Phe His Leu Asp Gly Glu Val Ile Thr Phe Asp
                725                 730                 735

Asn Leu Lys Thr Leu Leu Ser Leu Arg Glu Val Arg Thr Ile Lys Val
            740                 745                 750

Phe Thr Thr Val Asp Asn Ile Asn Leu His Thr Gln Val Val Asp Met
        755                 760                 765

Ser Met Thr Tyr Gly Gln Gln Phe Gly Pro Thr Tyr Leu Asp Gly Ala
    770                 775                 780

Asp Val Thr Lys Ile Lys Pro His Asn Ser His Glu Gly Lys Thr Phe
785                 790                 795                 800

Tyr Val Leu Pro Asn Asp Asp Thr Leu Arg Val Glu Ala Phe Glu Tyr
                805                 810                 815

Tyr His Thr Thr Asp Pro Ser Phe Leu Gly Arg Tyr Met Ser Ala Leu
            820                 825                 830

Asn His Thr Lys Lys Trp Lys Tyr Pro Gln Val Asn Gly Leu Thr Ser
        835                 840                 845

Ile Lys Trp Ala Asp Asn Asn Cys Tyr Leu Ala Thr Ala Leu Leu Thr
    850                 855                 860

Leu Gln Gln Ile Glu Leu Lys Phe Asn Pro Pro Ala Leu Gln Asp Ala
865                 870                 875                 880

Tyr Tyr Arg Ala Arg Ala Gly Glu Ala Ala Asn Phe Cys Ala Leu Ile
                885                 890                 895

Leu Ala Tyr Cys Asn Lys Thr Val Gly Glu Leu Gly Asp Val Arg Glu
            900                 905                 910

Thr Met Ser Tyr Leu Phe Gln His Ala Asn Leu Asp Ser Cys Lys Arg
        915                 920                 925

Val Leu Asn Val Val Cys Lys Thr Cys Gly Gln Gln Gln Thr Thr Leu
    930                 935                 940

Lys Gly Val Glu Ala Val Met Tyr Met Gly Thr Leu Ser Tyr Glu Gln
945                 950                 955                 960

Phe Lys Lys Gly Val Gln Ile Pro Cys Thr Cys Gly Lys Gln Ala Thr
                965                 970                 975

Lys Tyr Leu Val Gln Gln Glu Ser Pro Phe Val Met Met Ser Ala Pro
            980                 985                 990

Pro Ala Gln Tyr Glu Leu Lys His  Gly Thr Phe Thr Cys  Ala Ser Glu
        995                 1000                 1005

Tyr Thr  Gly Asn Tyr Gln Cys  Gly His Tyr Lys His  Ile Thr Ser
    1010                 1015                 1020

Lys Glu  Thr Leu Tyr Cys Ile  Asp Gly Ala Leu Leu  Thr Lys Ser
    1025                 1030                 1035

Ser Glu  Tyr Lys Gly Pro Ile  Thr Asp Val Phe Tyr  Lys Glu Asn
```

-continued

```
    1040                1045                1050

Ser Tyr  Thr Thr Thr Ile Lys  Pro Val Thr Tyr Lys  Leu Asp Gly
    1055                1060                1065

Val Val  Cys Thr Glu Ile Asp  Pro Lys Leu Asp Asn  Tyr Tyr Lys
    1070                1075                1080

Lys Asp  Asn Ser Tyr Phe Thr  Glu Gln Pro Ile Asp  Leu Val Pro
    1085                1090                1095

Asn Gln  Pro Tyr Pro Asn Ala  Ser Phe Asp Asn Phe  Lys Phe Val
    1100                1105                1110

Cys Asp  Asn Ile Lys Phe Ala  Asp Asp Leu Asn Gln  Leu Thr Gly
    1115                1120                1125

Tyr Lys  Lys Pro Ala Ser Arg  Glu Leu Lys Val Thr  Phe Phe Pro
    1130                1135                1140

Asp Leu  Asn Gly Asp Val Val  Ala Ile Asp Tyr Lys  His Tyr Thr
    1145                1150                1155

Pro Ser  Phe Lys Lys Gly Ala  Lys Leu Leu His Lys  Pro Ile Val
    1160                1165                1170

Trp His  Val Asn Asn Ala Thr  Asn Lys Ala Thr Tyr  Lys Pro Asn
    1175                1180                1185

Thr Trp  Cys Ile Arg Cys Leu  Trp Ser Thr Lys Pro  Val Glu Thr
    1190                1195                1200

Ser Asn  Ser Phe Asp Val Leu  Lys Ser Glu Asp Ala  Gln Gly Met
    1205                1210                1215

Asp Asn  Leu Ala Cys Glu Asp  Leu Lys Pro Val Ser  Glu Glu Val
    1220                1225                1230

Val Glu  Asn Pro Thr Ile Gln  Lys Asp Val Leu Glu  Cys Asn Val
    1235                1240                1245

Lys Thr  Thr Glu Val Val Gly  Asp Ile Ile Leu Lys  Pro Ala Asn
    1250                1255                1260

Asn Ser  Leu Lys Ile Thr Glu  Glu Val Gly His Thr  Asp Leu Met
    1265                1270                1275

Ala Ala  Tyr Val Asp Asn Ser  Ser Leu Thr Ile Lys  Lys Pro Asn
    1280                1285                1290

Glu Leu  Ser Arg Val Leu Gly  Leu Lys Thr Leu Ala  Thr His Gly
    1295                1300                1305

Leu Ala  Ala Val Asn Ser Val  Pro Trp Asp Thr Ile  Ala Asn Tyr
    1310                1315                1320

Ala Lys  Pro Phe Leu Asn Lys  Val Val Ser Thr Thr  Thr Asn Ile
    1325                1330                1335

Val Thr  Arg Cys Leu Asn Arg  Val Cys Thr Asn Tyr  Met Pro Tyr
    1340                1345                1350

Phe Phe  Thr Leu Leu Leu Gln  Leu Cys Thr Phe Thr  Arg Ser Thr
    1355                1360                1365

Asn Ser  Arg Ile Lys Ala Ser  Met Pro Thr Thr Ile  Ala Lys Asn
    1370                1375                1380

Thr Val  Lys Ser Val Gly Lys  Phe Cys Leu Glu Ala  Ser Phe Asn
    1385                1390                1395

Tyr Leu  Lys Ser Pro Asn Phe  Ser Lys Leu Ile Asn  Ile Ile Ile
    1400                1405                1410

Trp Phe  Leu Leu Leu Ser Val  Cys Leu Gly Ser Leu  Ile Tyr Ser
    1415                1420                1425

Thr Ala  Ala Leu Gly Val Leu  Met Ser Asn Leu Gly  Met Pro Ser
    1430                1435                1440
```

```
Tyr Cys  Thr Gly Tyr Arg Glu  Gly Tyr Leu Asn Ser  Thr Asn Val
    1445                 1450                 1455

Thr Ile  Ala Thr Tyr Cys Thr  Gly Ser Ile Pro Cys  Ser Val Cys
    1460                 1465                 1470

Leu Ser  Gly Leu Asp Ser Leu  Asp Thr Tyr Pro Ser  Leu Glu Thr
    1475                 1480                 1485

Ile Gln  Ile Thr Ile Ser Ser  Phe Lys Trp Asp Leu  Thr Ala Phe
    1490                 1495                 1500

Gly Leu  Val Ala Glu Trp Phe  Leu Ala Tyr Ile Leu  Phe Thr Arg
    1505                 1510                 1515

Phe Phe  Tyr Val Leu Gly Leu  Ala Ala Ile Met Gln  Leu Phe Phe
    1520                 1525                 1530

Ser Tyr  Phe Ala Val His Phe  Ile Ser Asn Ser Trp  Leu Met Trp
    1535                 1540                 1545

Leu Ile  Ile Asn Leu Val Gln  Met Ala Pro Ile Ser  Ala Met Val
    1550                 1555                 1560

Arg Met  Tyr Ile Phe Phe Ala  Ser Phe Tyr Tyr Val  Trp Lys Ser
    1565                 1570                 1575

Tyr Val  His Val Val Asp Gly  Cys Asn Ser Ser Thr  Cys Met Met
    1580                 1585                 1590

Cys Tyr  Lys Arg Asn Arg Ala  Thr Arg Val Glu Cys  Thr Thr Ile
    1595                 1600                 1605

Val Asn  Gly Val Arg Arg Ser  Phe Tyr Val Tyr Ala  Asn Gly Gly
    1610                 1615                 1620

Lys Gly  Phe Cys Lys Leu His  Asn Trp Asn Cys Val  Asn Cys Asp
    1625                 1630                 1635

Thr Phe  Cys Ala Gly Ser Thr  Phe Ile Ser Asp Glu  Val Ala Arg
    1640                 1645                 1650

Asp Leu  Ser Leu Gln Phe Lys  Arg Pro Ile Asn Pro  Thr Asp Gln
    1655                 1660                 1665

Ser Ser  Tyr Ile Val Asp Ser  Val Thr Val Lys Asn  Gly Ser Ile
    1670                 1675                 1680

His Leu  Tyr Phe Asp Lys Ala  Gly Gln Lys Thr Tyr  Glu Arg His
    1685                 1690                 1695

Ser Leu  Ser His Phe Val Asn  Leu Asp Asn Leu Arg  Ala Asn Asn
    1700                 1705                 1710

Thr Lys  Gly Ser Leu Pro Ile  Asn Val Ile Val Phe  Asp Gly Lys
    1715                 1720                 1725

Ser Lys  Cys Glu Glu Ser Ser  Ala Lys Ser Ala Ser  Val Tyr Tyr
    1730                 1735                 1740

Ser Gln  Leu Met Cys Gln Pro  Ile Leu Leu Leu Asp  Gln Ala Leu
    1745                 1750                 1755

Val Ser  Asp Val Gly Asp Ser  Ala Glu Val Ala Val  Lys Met Phe
    1760                 1765                 1770

Asp Ala  Tyr Val Asn Thr Phe  Ser Ser Thr Phe Asn  Val Pro Met
    1775                 1780                 1785

Glu Lys  Leu Lys Thr Leu Val  Ala Thr Ala Glu Ala  Glu Leu Ala
    1790                 1795                 1800

Lys Asn  Val Ser Leu Asp Asn  Val Leu Ser Thr Phe  Ile Ser Ala
    1805                 1810                 1815

Ala Arg  Gln Gly Phe Val Asp  Ser Asp Val Glu Thr  Lys Asp Val
    1820                 1825                 1830
```

-continued

```
Val Glu  Cys Leu Lys Leu Ser  His Gln Ser Asp Ile  Glu Val Thr
    1835                1840                1845

Gly Asp  Ser Cys Asn Asn Tyr  Met Leu Thr Tyr Asn  Lys Val Glu
    1850                1855                1860

Asn Met  Thr Pro Arg Asp Leu  Gly Ala Cys Ile Asp  Cys Ser Ala
    1865                1870                1875

Arg His  Ile Asn Ala Gln Val  Ala Lys Ser His Asn  Ile Ala Leu
    1880                1885                1890

Ile Trp  Asn Val Lys Asp Phe  Met Ser Leu Ser Glu  Gln Leu Arg
    1895                1900                1905

Lys Gln  Ile Arg Ser Ala Ala  Lys Lys Asn Asn Leu  Pro Phe Lys
    1910                1915                1920

Leu Thr  Cys Ala Thr Thr Arg  Gln Val Val Asn Val  Val Thr Thr
    1925                1930                1935

Lys Ile  Ala Leu Lys Gly Gly
    1940                1945


<210> SEQ ID NO 4
<211> LENGTH: 198
<212> TYPE: PRT
<213> ORGANISM: Severe acute respiratory syndrome coronavirus 2

<400> SEQUENCE: 4

Ala Ile Ala Ser Glu Phe Ser Ser Leu Pro Ser Tyr Ala Ala Phe Ala
1               5                   10                  15

Thr Ala Gln Glu Ala Tyr Glu Gln Ala Val Ala Asn Gly Asp Ser Glu
            20                  25                  30

Val Val Leu Lys Lys Leu Lys Lys Ser Leu Asn Val Ala Lys Ser Glu
        35                  40                  45

Phe Asp Arg Asp Ala Ala Met Gln Arg Lys Leu Glu Lys Met Ala Asp
    50                  55                  60

Gln Ala Met Thr Gln Met Tyr Lys Gln Ala Arg Ser Glu Asp Lys Arg
65                  70                  75                  80

Ala Lys Val Thr Ser Ala Met Gln Thr Met Leu Phe Thr Met Leu Arg
                85                  90                  95

Lys Leu Asp Asn Asp Ala Leu Asn Asn Ile Ile Asn Asn Ala Arg Asp
            100                 105                 110

Gly Cys Val Pro Leu Asn Ile Ile Pro Leu Thr Thr Ala Ala Lys Leu
        115                 120                 125

Met Val Val Ile Pro Asp Tyr Asn Thr Tyr Lys Asn Thr Cys Asp Gly
    130                 135                 140

Thr Thr Phe Thr Tyr Ala Ser Ala Leu Trp Glu Ile Gln Gln Val Val
145                 150                 155                 160

Asp Ala Asp Ser Lys Ile Val Gln Leu Ser Glu Ile Ser Met Asp Asn
                165                 170                 175

Ser Pro Asn Leu Ala Trp Pro Leu Ile Val Thr Ala Leu Arg Ala Asn
            180                 185                 190

Ser Ala Val Lys Leu Gln
        195


<210> SEQ ID NO 5
<211> LENGTH: 113
<212> TYPE: PRT
<213> ORGANISM: Severe acute respiratory syndrome coronavirus 2

<400> SEQUENCE: 5
```

```
Asn Asn Glu Leu Ser Pro Val Ala Leu Arg Gln Met Ser Cys Ala Ala
1               5                   10                  15

Gly Thr Thr Gln Thr Ala Cys Thr Asp Asp Asn Ala Leu Ala Tyr Tyr
            20                  25                  30

Asn Thr Thr Lys Gly Gly Arg Phe Val Leu Ala Leu Leu Ser Asp Leu
        35                  40                  45

Gln Asp Leu Lys Trp Ala Arg Phe Pro Lys Ser Asp Gly Thr Gly Thr
    50                  55                  60

Ile Tyr Thr Glu Leu Glu Pro Pro Cys Arg Phe Val Thr Asp Thr Pro
65                  70                  75                  80

Lys Gly Pro Lys Val Lys Tyr Leu Tyr Phe Ile Lys Gly Leu Asn Asn
                85                  90                  95

Leu Asn Arg Gly Met Val Leu Gly Ser Leu Ala Ala Thr Val Arg Leu
            100                 105                 110

Gln


<210> SEQ ID NO 6
<211> LENGTH: 139
<212> TYPE: PRT
<213> ORGANISM: Severe acute respiratory syndrome coronavirus 2

<400> SEQUENCE: 6

Ala Gly Asn Ala Thr Glu Val Pro Ala Asn Ser Thr Val Leu Ser Phe
1               5                   10                  15

Cys Ala Phe Ala Val Asp Ala Ala Lys Ala Tyr Lys Asp Tyr Leu Ala
            20                  25                  30

Ser Gly Gly Gln Pro Ile Thr Asn Cys Val Lys Met Leu Cys Thr His
        35                  40                  45

Thr Gly Thr Gly Gln Ala Ile Thr Val Thr Pro Glu Ala Asn Met Asp
    50                  55                  60

Gln Glu Ser Phe Gly Gly Ala Ser Cys Cys Leu Tyr Cys Arg Cys His
65                  70                  75                  80

Ile Asp His Pro Asn Pro Lys Gly Phe Cys Asp Leu Lys Gly Lys Tyr
                85                  90                  95

Val Gln Ile Pro Thr Thr Cys Ala Asn Asp Pro Val Gly Phe Thr Leu
            100                 105                 110

Lys Asn Thr Val Cys Thr Val Cys Gly Met Trp Lys Gly Tyr Gly Cys
        115                 120                 125

Ser Cys Asp Gln Leu Arg Glu Pro Met Leu Gln
    130                 135


<210> SEQ ID NO 7
<211> LENGTH: 306
<212> TYPE: PRT
<213> ORGANISM: Severe acute respiratory syndrome coronavirus 2

<400> SEQUENCE: 7

Ser Gly Phe Arg Lys Met Ala Phe Pro Ser Gly Lys Val Glu Gly Cys
1               5                   10                  15

Met Val Gln Val Thr Cys Gly Thr Thr Thr Leu Asn Gly Leu Trp Leu
            20                  25                  30

Asp Asp Val Val Tyr Cys Pro Arg His Val Ile Cys Thr Ser Glu Asp
        35                  40                  45

Met Leu Asn Pro Asn Tyr Glu Asp Leu Leu Ile Arg Lys Ser Asn His
    50                  55                  60

Asn Phe Leu Val Gln Ala Gly Asn Val Gln Leu Arg Val Ile Gly His
```

```
65                  70                  75                  80

Ser Met Gln Asn Cys Val Leu Lys Leu Lys Val Asp Thr Ala Asn Pro
                85                  90                  95

Lys Thr Pro Lys Tyr Lys Phe Val Arg Ile Gln Pro Gly Gln Thr Phe
            100                 105                 110

Ser Val Leu Ala Cys Tyr Asn Gly Ser Pro Ser Gly Val Tyr Gln Cys
        115                 120                 125

Ala Met Arg Pro Asn Phe Thr Ile Lys Gly Ser Phe Leu Asn Gly Ser
    130                 135                 140

Cys Gly Ser Val Gly Phe Asn Ile Asp Tyr Asp Cys Val Ser Phe Cys
145                 150                 155                 160

Tyr Met His His Met Glu Leu Pro Thr Gly Val His Ala Gly Thr Asp
                165                 170                 175

Leu Glu Gly Asn Phe Tyr Gly Pro Phe Val Asp Arg Gln Thr Ala Gln
            180                 185                 190

Ala Ala Gly Thr Asp Thr Thr Ile Thr Val Asn Val Leu Ala Trp Leu
        195                 200                 205

Tyr Ala Ala Val Ile Asn Gly Asp Arg Trp Phe Leu Asn Arg Phe Thr
    210                 215                 220

Thr Thr Leu Asn Asp Phe Asn Leu Val Ala Met Lys Tyr Asn Tyr Glu
225                 230                 235                 240

Pro Leu Thr Gln Asp His Val Asp Ile Leu Gly Pro Leu Ser Ala Gln
                245                 250                 255

Thr Gly Ile Ala Val Leu Asp Met Cys Ala Ser Leu Lys Glu Leu Leu
            260                 265                 270

Gln Asn Gly Met Asn Gly Arg Thr Ile Leu Gly Ser Ala Leu Leu Glu
        275                 280                 285

Asp Glu Phe Thr Pro Phe Asp Val Val Arg Gln Cys Ser Gly Val Thr
    290                 295                 300

Phe Gln
305


<210> SEQ ID NO 8
<211> LENGTH: 419
<212> TYPE: PRT
<213> ORGANISM: Severe acute respiratory syndrome coronavirus 2

<400> SEQUENCE: 8

Met Ser Asp Asn Gly Pro Gln Asn Gln Arg Asn Ala Pro Arg Ile Thr
1               5                   10                  15

Phe Gly Gly Pro Ser Asp Ser Thr Gly Ser Asn Gln Asn Gly Glu Arg
            20                  25                  30

Ser Gly Ala Arg Ser Lys Gln Arg Arg Pro Gln Gly Leu Pro Asn Asn
        35                  40                  45

Thr Ala Ser Trp Phe Thr Ala Leu Thr Gln His Gly Lys Glu Asp Leu
    50                  55                  60

Lys Phe Pro Arg Gly Gln Gly Val Pro Ile Asn Thr Asn Ser Ser Pro
65                  70                  75                  80

Asp Asp Gln Ile Gly Tyr Tyr Arg Arg Ala Thr Arg Arg Ile Arg Gly
                85                  90                  95

Gly Asp Gly Lys Met Lys Asp Leu Ser Pro Arg Trp Tyr Phe Tyr Tyr
            100                 105                 110

Leu Gly Thr Gly Pro Glu Ala Gly Leu Pro Tyr Gly Ala Asn Lys Asp
        115                 120                 125
```

```
Gly Ile Ile Trp Val Ala Thr Glu Gly Ala Leu Asn Thr Pro Lys Asp
    130                 135                 140

His Ile Gly Thr Arg Asn Pro Ala Asn Asn Ala Ala Ile Val Leu Gln
145                 150                 155                 160

Leu Pro Gln Gly Thr Thr Leu Pro Lys Gly Phe Tyr Ala Glu Gly Ser
                165                 170                 175

Arg Gly Gly Ser Gln Ala Ser Ser Arg Ser Ser Ser Arg Ser Arg Asn
            180                 185                 190

Ser Ser Arg Asn Ser Thr Pro Gly Ser Ser Arg Gly Thr Ser Pro Ala
        195                 200                 205

Arg Met Ala Gly Asn Gly Gly Asp Ala Ala Leu Ala Leu Leu Leu Leu
    210                 215                 220

Asp Arg Leu Asn Gln Leu Glu Ser Lys Met Ser Gly Lys Gly Gln Gln
225                 230                 235                 240

Gln Gln Gly Gln Thr Val Thr Lys Lys Ser Ala Ala Glu Ala Ser Lys
                245                 250                 255

Lys Pro Arg Gln Lys Arg Thr Ala Thr Lys Ala Tyr Asn Val Thr Gln
            260                 265                 270

Ala Phe Gly Arg Arg Gly Pro Glu Gln Thr Gln Gly Asn Phe Gly Asp
        275                 280                 285

Gln Glu Leu Ile Arg Gln Gly Thr Asp Tyr Lys His Trp Pro Gln Ile
    290                 295                 300

Ala Gln Phe Ala Pro Ser Ala Ser Ala Phe Phe Gly Met Ser Arg Ile
305                 310                 315                 320

Gly Met Glu Val Thr Pro Ser Gly Thr Trp Leu Thr Tyr Thr Gly Ala
                325                 330                 335

Ile Lys Leu Asp Asp Lys Asp Pro Asn Phe Lys Asp Gln Val Ile Leu
            340                 345                 350

Leu Asn Lys His Ile Asp Ala Tyr Lys Thr Phe Pro Pro Thr Glu Pro
        355                 360                 365

Lys Lys Asp Lys Lys Lys Lys Ala Asp Glu Thr Gln Ala Leu Pro Gln
    370                 375                 380

Arg Gln Lys Lys Gln Gln Thr Val Thr Leu Leu Pro Ala Ala Asp Leu
385                 390                 395                 400

Asp Asp Phe Ser Lys Gln Leu Gln Gln Ser Met Ser Ser Ala Asp Ser
                405                 410                 415

Thr Gln Ala


<210> SEQ ID NO 9
<211> LENGTH: 941
<212> TYPE: PRT
<213> ORGANISM: Human immunodeficiency virus 1

<400> SEQUENCE: 9

Met Gly Asn Leu Trp Val Thr Val Tyr Tyr Gly Val Pro Val Trp Lys
1               5                   10                  15

Glu Ala Lys Thr Thr Leu Phe Cys Ala Ser Asp Ala Lys Ala Tyr Glu
            20                  25                  30

Gln Glu Val His Asn Val Trp Ala Thr His Ala Cys Val Pro Thr Asp
        35                  40                  45

Pro Asn Pro Gln Glu Met Arg Met Glu Asn Val Thr Glu Asn Phe Asn
    50                  55                  60

Met Trp Lys Asn Asp Met Val Asp Gln Met His Glu Asp Ile Ile Ser
65                  70                  75                  80
```

-continued

```
Leu Trp Asp Gln Ser Leu Lys Pro Cys Val Lys Leu Thr Pro Leu Cys
                85                  90                  95

Val Thr Leu Asp Cys Gln Asn Val Asn Ala Thr Gln Asn Thr Asn Asp
            100                 105                 110

Thr Ile Ser Thr Met Lys Asn Cys Thr Phe Asn Thr Thr Ala Asp Leu
        115                 120                 125

Gly Asp Lys Lys Gln Lys Gly Arg Ala Leu Phe Tyr Asn Leu Asp Ile
    130                 135                 140

Val Gln Leu Asn Pro Asn Ser Asn Ser Ser Glu Tyr Arg Leu Ile Ser
145                 150                 155                 160

Cys Asn Thr Ser Thr Ile Thr Gln Ala Cys Pro Lys Val Ser Phe Glu
                165                 170                 175

Pro Ile Pro Ile His Tyr Cys Ala Pro Ala Gly Tyr Ala Ile Leu Lys
            180                 185                 190

Cys Asn Asn Lys Thr Phe Asn Gly Leu Gly Pro Cys Thr Asn Val Ser
        195                 200                 205

Thr Val Gln Cys Thr His Gly Ile Lys Pro Val Val Ser Thr Gln Leu
    210                 215                 220

Leu Leu Asn Gly Ser Leu Ala Glu Gly Glu Ile Ile Ile Arg Ser Glu
225                 230                 235                 240

Asn Leu Thr Asp Asn Gly Lys Thr Ile Ile Val His Leu Asn Glu Ser
                245                 250                 255

Val Lys Ile Val Cys Ile Arg Pro Asn Asn Asn Thr Arg Lys Ser Ile
            260                 265                 270

Arg Ile Gly Pro Gly Gln Thr Phe Phe Ala Thr Asp Ile Ile Gly Asp
        275                 280                 285

Ile Arg Gln Ala Tyr Cys Asn Ile Ser Arg Glu Asp Trp Asn Lys Thr
    290                 295                 300

Leu Asp Arg Val Arg Lys Lys Leu Glu Glu His Phe Pro Asn Lys Thr
305                 310                 315                 320

Ile Glu Phe Lys Arg His Ser Gly Gly Asp Leu Glu Val Thr Gln His
                325                 330                 335

Ser Phe Asn Cys Arg Gly Glu Phe Phe Tyr Cys Asn Thr Thr His Leu
            340                 345                 350

Phe Glu Asn Thr Thr Tyr Thr Asn Ser Ser Asn Ile Thr Leu Pro Cys
        355                 360                 365

Arg Ile Lys Gln Ile Ile Asn Met Trp Gln Gly Val Gly Arg Ala Met
    370                 375                 380

Tyr Ala Pro Pro Ile Ala Gly Asn Ile Thr Cys Ile Ser Asn Ile Thr
385                 390                 395                 400

Gly Ile Leu Leu Thr Arg Asp Gly Gly Asn Asn Gly Thr Asn Glu Thr
                405                 410                 415

Phe Arg Pro Gly Gly Gly Asp Met Arg Asp Asn Trp Arg Ser Glu Leu
            420                 425                 430

Tyr Lys Tyr Lys Val Val Glu Ile Lys Pro Leu Gly Ile Ala Pro Thr
        435                 440                 445

Lys Cys Lys Arg Arg Val Val Glu Arg Arg Arg Arg Arg Arg Ala Val
    450                 455                 460

Gly Met Gly Ala Leu Phe Leu Gly Phe Leu Gly Ala Ala Gly Ser Thr
465                 470                 475                 480

Met Gly Ala Ala Ser Met Thr Leu Thr Val Gln Ala Arg Gln Leu Leu
                485                 490                 495

Ser Gly Ile Val Gln Gln Gln Ser Asn Leu Leu Arg Ala Pro Glu Ala
```

-continued

```
            500                 505                 510

Gln Gln His Met Leu Gln Leu Thr Val Trp Gly Ile Lys Gln Leu Gln
        515                 520                 525

Ala Arg Val Leu Ala Leu Glu Arg Tyr Leu Gln Asp Gln Gln Leu Leu
    530                 535                 540

Gly Ile Trp Gly Cys Ser Gly Lys Leu Ile Cys Cys Thr Ala Val Pro
545                 550                 555                 560

Trp Asn Ser Ser Trp Ser Asn Lys Thr Tyr Asn Asp Ile Trp Asp Asn
                565                 570                 575

Met Thr Trp Met Gln Trp Glu Arg Glu Ile Ser Asn Tyr Thr Asn Thr
            580                 585                 590

Ile Tyr Thr Leu Leu Glu Val Ser Gln Asn Gln Gln Glu Gln Asn Glu
        595                 600                 605

Lys Asp Leu Leu Ala Leu Asp Arg Gln Ala Tyr Cys Asn Ile Ser Arg
    610                 615                 620

Glu Asp Trp Asn Lys Thr Leu Asp Arg Val Arg Lys Lys Leu Glu Glu
625                 630                 635                 640

His Phe Pro Asn Lys Thr Ile Glu Phe Lys Arg His Ser Gly Gly Asp
                645                 650                 655

Leu Glu Val Thr Gln His Ser Phe Asn Cys Arg Gly Glu Phe Phe Tyr
            660                 665                 670

Cys Asn Thr Thr His Leu Phe Glu Asn Thr Thr Tyr Thr Asn Ser Ser
        675                 680                 685

Asn Ile Thr Leu Pro Cys Arg Ile Lys Gln Ile Ile Asn Met Trp Gln
    690                 695                 700

Gly Val Gly Arg Ala Met Tyr Ala Pro Pro Ile Ala Gly Asn Ile Thr
705                 710                 715                 720

Cys Ile Ser Asn Ile Thr Gly Ile Leu Leu Thr Arg Asp Gly Gly Asn
                725                 730                 735

Asn Gly Thr Asn Glu Thr Phe Arg Pro Gly Gly Gly Asp Met Arg Asp
            740                 745                 750

Asn Trp Arg Ser Glu Leu Tyr Lys Tyr Lys Val Val Glu Ile Lys Pro
        755                 760                 765

Leu Gly Ile Ala Pro Thr Lys Cys Lys Arg Arg Val Val Glu Arg Arg
    770                 775                 780

Arg Arg Arg Arg Ala Val Gly Met Gly Ala Leu Phe Leu Gly Phe Leu
785                 790                 795                 800

Gly Ala Ala Gly Ser Thr Met Gly Ala Ala Ser Met Thr Leu Thr Val
                805                 810                 815

Gln Ala Arg Gln Leu Leu Ser Gly Ile Val Gln Gln Gln Ser Asn Leu
            820                 825                 830

Leu Arg Ala Pro Glu Ala Gln Gln His Met Leu Gln Leu Thr Val Trp
        835                 840                 845

Gly Ile Lys Gln Leu Gln Ala Arg Val Leu Ala Leu Glu Arg Tyr Leu
    850                 855                 860

Gln Asp Gln Gln Leu Leu Gly Ile Trp Gly Cys Ser Gly Lys Leu Ile
865                 870                 875                 880

Cys Cys Thr Ala Val Pro Trp Asn Ser Ser Trp Ser Asn Lys Thr Tyr
                885                 890                 895

Asn Asp Ile Trp Asp Asn Met Thr Trp Met Gln Trp Glu Arg Glu Ile
            900                 905                 910

Ser Asn Tyr Thr Asn Thr Ile Tyr Thr Leu Leu Glu Val Ser Gln Asn
        915                 920                 925
```

```
Gln Gln Glu Gln Asn Glu Lys Asp Leu Leu Ala Leu Asp
    930                 935                 940


<210> SEQ ID NO 10
<211> LENGTH: 615
<212> TYPE: PRT
<213> ORGANISM: Human immunodeficiency virus 1

<400> SEQUENCE: 10

Met Gly Asn Leu Trp Val Thr Val Tyr Tyr Gly Val Pro Val Trp Lys
1               5                   10                  15

Glu Ala Lys Thr Thr Leu Phe Cys Ala Ser Asp Ala Lys Ala Tyr Glu
            20                  25                  30

Gln Glu Val His Asn Val Trp Ala Thr His Ala Cys Val Pro Thr Asp
        35                  40                  45

Pro Asn Pro Gln Glu Met Arg Met Glu Asn Val Thr Glu Asn Phe Asn
    50                  55                  60

Met Trp Lys Asn Asp Met Val Asp Gln Met His Glu Asp Ile Ile Ser
65                  70                  75                  80

Leu Trp Asp Gln Ser Leu Lys Pro Cys Cys Lys Leu Thr Pro Leu Cys
                85                  90                  95

Val Thr Leu Asp Cys Gln Asn Val Asn Ala Thr Gln Asn Thr Asn Asp
            100                 105                 110

Thr Ile Ser Thr Met Lys Asn Cys Thr Phe Asn Thr Thr Ala Asp Leu
        115                 120                 125

Gly Asp Lys Lys Gln Lys Gly Arg Ala Leu Phe Tyr Asn Leu Asp Ile
    130                 135                 140

Val Gln Leu Asn Pro Asn Ser Asn Ser Ser Glu Tyr Arg Leu Ile Ser
145                 150                 155                 160

Cys Asn Thr Ser Thr Cys Thr Gln Ala Cys Pro Lys Val Ser Phe Glu
                165                 170                 175

Pro Ile Pro Ile His Tyr Cys Ala Pro Ala Gly Tyr Ala Ile Leu Lys
            180                 185                 190

Cys Asn Asn Lys Thr Phe Asn Gly Leu Gly Pro Cys Thr Asn Val Ser
        195                 200                 205

Thr Val Gln Cys Thr His Gly Ile Lys Pro Val Val Ser Thr Gln Leu
    210                 215                 220

Leu Leu Asn Gly Ser Leu Ala Glu Gly Glu Ile Ile Ile Arg Ser Glu
225                 230                 235                 240

Asn Leu Thr Asp Asn Gly Lys Thr Ile Ile Val His Leu Asn Glu Ser
                245                 250                 255

Val Lys Ile Val Cys Ile Arg Pro Asn Asn Asn Thr Arg Lys Ser Ile
            260                 265                 270

Arg Ile Gly Pro Gly Cys Thr Phe Phe Ala Thr Asp Ile Ile Gly Asp
        275                 280                 285

Ile Arg Gln Ala Tyr Cys Asn Ile Ser Arg Glu Asp Trp Asn Lys Thr
    290                 295                 300

Leu Asp Arg Val Arg Lys Lys Leu Glu Glu His Phe Pro Asn Lys Thr
305                 310                 315                 320

Ile Glu Phe Lys Gln His Ser Gly Gly Asp Leu Glu Val Thr Gln His
                325                 330                 335

Ser Phe Asn Cys Arg Gly Glu Phe Phe Tyr Cys Asn Thr Thr His Leu
            340                 345                 350

Phe Glu Asn Thr Thr Tyr Thr Asn Ser Ser Asn Ile Thr Leu Pro Cys
```

```
        355                 360                 365

Arg Ile Lys Gln Ile Ile Asn Met Trp Gln Gly Val Gly Arg Cys Met
    370                 375                 380

Tyr Ala Pro Pro Ile Ala Gly Asn Ile Thr Cys Ile Ser Asn Ile Thr
385                 390                 395                 400

Gly Ile Leu Leu Thr Arg Asp Gly Gly Asn Asn Gly Thr Asn Glu Thr
                405                 410                 415

Phe Arg Pro Gly Gly Gly Asp Met Arg Asp Asn Trp Arg Ser Glu Leu
            420                 425                 430

Tyr Lys Tyr Lys Val Val Glu Ile Lys Pro Leu Gly Ile Ala Pro Thr
        435                 440                 445

Lys Cys Lys Arg Arg Val Val Glu Arg Arg Arg Arg Arg Arg Ala Val
    450                 455                 460

Gly Met Gly Ala Leu Ser Leu Gly Phe Leu Gly Ala Ala Gly Ser Thr
465                 470                 475                 480

Met Gly Ala Ala Ser Met Thr Leu Thr Val Gln Ala Arg Gln Leu Leu
                485                 490                 495

Ser Gly Ile Val Gln Gln Gln Ser Asn Leu Leu Arg Ala Pro Glu Pro
            500                 505                 510

Gln Glu His Met His Gln Asp Thr His Trp Gly Ile Lys Gln Leu Gln
        515                 520                 525

Ala Arg Val Leu Ala Leu Glu His Tyr Leu Gln Asp Gln Gln Leu Leu
    530                 535                 540

Gly Ile Trp Gly Cys Ser Gly Lys Leu Ile Cys Cys Thr Ala Val Pro
545                 550                 555                 560

Trp Asn Ser Ser Trp Ser Asn Lys Thr Tyr Asn Asp Ile Trp Asp Asn
                565                 570                 575

Met Thr Trp Met Gln Trp Glu Arg Glu Ile Ser Asn Tyr Thr Asn Thr
            580                 585                 590

Ile Tyr Thr Leu Leu Glu Val Ser Gln Asn Gln Gln Glu Gln Asn Glu
        595                 600                 605

Lys Asp Leu Leu Ala Leu Asp
    610                 615


<210> SEQ ID NO 11
<211> LENGTH: 615
<212> TYPE: PRT
<213> ORGANISM: Human immunodeficiency virus 1

<400> SEQUENCE: 11

Met Gly Asn Leu Trp Val Thr Val Tyr Tyr Gly Val Pro Val Trp Lys
1               5                   10                  15

Glu Ala Lys Thr Thr Leu Phe Cys Ala Ser Asp Ala Lys Ala Tyr Glu
            20                  25                  30

Gln Glu Val His Asn Val Trp Ala Thr His Ala Cys Val Pro Thr Asp
        35                  40                  45

Pro Asn Pro Gln Glu Met Arg Met Glu Asn Val Thr Glu Asn Phe Asn
    50                  55                  60

Met Trp Lys Asn Asp Met Val Asp Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Asp Cys Gln Asn Val Asn Ala Thr Gln Asn Thr Asn Asp
            100                 105                 110
```

-continued

```
Thr Ile Ser Thr Met Lys Asn Cys Thr Phe Asn Thr Thr Ala Asp Leu
        115                 120                 125

Gly Asp Lys Lys Gln Lys Gly Arg Ala Leu Phe Tyr Asn Leu Asp Ile
    130                 135                 140

Val Gln Leu Asn Pro Asn Ser Asn Ser Ser Glu Tyr Arg Leu Ile Ser
145                 150                 155                 160

Cys Asn Thr Ser Thr Ile Thr Gln Ala Cys Pro Lys Val Ser Phe Glu
                165                 170                 175

Pro Ile Pro Ile His Tyr Cys Ala Pro Ala Gly Tyr Ala Ile Leu Lys
            180                 185                 190

Cys Asn Asn Lys Thr Phe Asn Gly Leu Gly Pro Cys Thr Asn Val Ser
        195                 200                 205

Thr Val Gln Cys Thr His Gly Ile Lys Pro Val Val Ser Thr Gln Leu
    210                 215                 220

Leu Leu Asn Gly Ser Leu Ala Glu Gly Glu Ile Ile Ile Arg Ser Glu
225                 230                 235                 240

Asn Leu Thr Asp Asn Gly Lys Thr Ile Ile Val His Leu Asn Glu Ser
                245                 250                 255

Val Lys Ile Val Cys Ile Arg Pro Asn Asn Asn Thr Val Lys Ser Ile
            260                 265                 270

Arg Ile Gly Pro Gly Gln Thr Phe Phe Tyr Thr Asp Ile Ile Gly Asp
        275                 280                 285

Ile Arg Gln Ala Tyr Cys Asn Ile Ser Arg Glu Asp Trp Asn Lys Thr
    290                 295                 300

Leu Asp Arg Val Arg Lys Lys Leu Glu Glu His Phe Pro Asn Lys Thr
305                 310                 315                 320

Ile Glu Phe Lys Gln His Ser Gly Gly Asp Leu Glu Val Thr Gln His
                325                 330                 335

Ser Phe Asn Cys Arg Gly Glu Phe Phe Tyr Cys Asn Thr Thr His Leu
            340                 345                 350

Phe Glu Asn Thr Thr Tyr Thr Asn Ser Ser Asn Ile Thr Leu Pro Cys
        355                 360                 365

Arg Ile Lys Gln Ile Ile Asn Met Trp Gln Gly Val Gly Arg Ala Met
    370                 375                 380

Tyr Ala Pro Pro Ile Ala Gly Asn Ile Thr Cys Ile Ser Asn Ile Thr
385                 390                 395                 400

Gly Ile Leu Leu Thr Arg Asp Gly Gly Asn Asn Gly Thr Asn Glu Thr
                405                 410                 415

Phe Arg Pro Gly Gly Gly Asp Met Arg Asp Asn Trp Arg Ser Glu Leu
            420                 425                 430

Tyr Lys Tyr Lys Val Val Glu Ile Lys Pro Leu Gly Ile Ala Pro Thr
        435                 440                 445

Lys Cys Lys Arg Arg Val Val Glu Arg Arg Arg Arg Arg Arg Ala Val
    450                 455                 460

Gly Met Gly Ala Leu Ser Leu Gly Phe Leu Gly Ala Ala Gly Ser Thr
465                 470                 475                 480

Met Gly Ala Ala Ser Met Thr Leu Thr Val Gln Ala Arg Gln Leu Leu
                485                 490                 495

Ser Gly Ile Val Gln Gln Gln Ser Asn Leu Leu Arg Ala Pro Glu Pro
            500                 505                 510

Gln Gln His Met Leu Gln Asp Thr His Trp Gly Ile Lys Gln Leu Gln
        515                 520                 525

Ala Arg Val Leu Ala Leu Glu His Tyr Leu Gln Asp Gln Gln Leu Leu
```

```
    530                 535                 540

Gly Ile Trp Gly Cys Ser Gly Lys Leu Ile Cys Cys Thr Ala Val Pro
545                 550                 555                 560

Trp Asn Ser Ser Trp Ser Asn Lys Thr Tyr Asn Asp Ile Trp Asp Asn
                565                 570                 575

Met Thr Trp Met Gln Trp Glu Arg Glu Ile Ser Asn Tyr Thr Asn Thr
            580                 585                 590

Ile Tyr Thr Leu Leu Glu Val Ser Gln Asn Gln Gln Glu Gln Asn Glu
        595                 600                 605

Lys Asp Leu Leu Ala Leu Asp
    610                 615


<210> SEQ ID NO 12
<211> LENGTH: 635
<212> TYPE: PRT
<213> ORGANISM: Human immunodeficiency virus 1

<400> SEQUENCE: 12

Val Glu Asn Leu Trp Val Thr Val Tyr Tyr Gly Val Pro Val Trp Lys
1               5                   10                  15

Glu Ala Thr Thr Thr Leu Phe Cys Ala Ser Asp Ala Lys Ala Tyr Asp
            20                  25                  30

Thr Glu Val His Asn Val Trp Ala Thr His Ala Cys Val Pro Thr Asp
        35                  40                  45

Pro Asn Pro Gln Glu Val Val Leu Glu Asn Val Thr Glu Asn Phe Asn
    50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Asn Cys Thr Asp Leu Arg Asn Val Thr Asn Ile Asn Asn
            100                 105                 110

Ser Ser Glu Gly Met Arg Gly Glu Ile Lys Asn Cys Ser Phe Asn Ile
        115                 120                 125

Thr Thr Ser Ile Arg Asp Lys Val Lys Lys Asp Tyr Ala Leu Phe Tyr
    130                 135                 140

Arg Leu Asp Val Val Pro Ile Asp Asn Asp Asn Thr Ser Tyr Arg Leu
145                 150                 155                 160

Ile Asn Cys Asn Thr Ser Thr Ile Thr Gln Ala Cys Pro Lys Val Ser
                165                 170                 175

Phe Glu Pro Ile Pro Ile His Tyr Cys Thr Pro Ala Gly Phe Ala Ile
            180                 185                 190

Leu Lys Cys Lys Asp Lys Lys Phe Asn Gly Thr Gly Pro Cys Lys Asn
        195                 200                 205

Val Ser Thr Val Gln Cys Thr His Gly Ile Arg Pro Val Val Ser Thr
    210                 215                 220

Gln Leu Leu Leu Asn Gly Ser Leu Ala Glu Glu Glu Val Val Ile Arg
225                 230                 235                 240

Ser Ser Asn Phe Thr Asp Asn Ala Lys Asn Ile Ile Val Gln Leu Lys
                245                 250                 255

Glu Ser Val Glu Ile Asn Cys Thr Arg Pro Asn Asn Asn Thr Arg Lys
            260                 265                 270

Ser Ile His Ile Gly Pro Gly Arg Ala Phe Tyr Thr Thr Gly Asp Ile
        275                 280                 285
```

```
Ile Gly Asp Ile Arg Gln Ala His Cys Asn Ile Ser Arg Thr Lys Trp
    290                 295                 300

Asn Asn Thr Leu Asn Gln Ile Ala Thr Lys Leu Lys Glu Gln Phe Gly
305                 310                 315                 320

Asn Asn Lys Thr Ile Val Phe Asn Gln Ser Ser Gly Gly Asp Pro Glu
                325                 330                 335

Ile Val Met His Ser Phe Asn Cys Gly Gly Glu Phe Phe Tyr Cys Asn
            340                 345                 350

Ser Thr Gln Leu Phe Asn Ser Thr Trp Asn Phe Asn Gly Thr Trp Asn
        355                 360                 365

Leu Thr Gln Ser Asn Gly Thr Glu Gly Asn Asp Thr Ile Thr Leu Pro
    370                 375                 380

Cys Arg Ile Lys Gln Ile Ile Asn Met Trp Gln Glu Val Gly Lys Ala
385                 390                 395                 400

Met Tyr Ala Pro Pro Ile Arg Gly Gln Ile Arg Cys Ser Ser Asn Ile
                405                 410                 415

Thr Gly Leu Ile Leu Thr Arg Asp Gly Gly Asn Asn His Asn Asn Asp
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Lys Cys Lys Arg Arg Val Val Gln Arg Arg Arg Arg Arg
465                 470                 475                 480

Arg Ala Val Gly Thr Ile Gly Ala Met Phe Leu Gly Phe Leu Gly Ala
                485                 490                 495

Ala Gly Ser Thr Met Gly Ala Ala Ser Ile Thr Leu Thr Val Gln Ala
            500                 505                 510

Arg Leu Leu Leu Ser Gly Ile Val Gln Gln Gln Asn Asn Leu Leu Arg
        515                 520                 525

Ala Pro Glu Ala Gln Gln His Leu Leu Gln Leu Thr Val Trp Gly Ile
    530                 535                 540

Lys Gln Leu Gln Ala Arg Val Leu Ala Val Glu Arg Tyr Leu Arg Asp
545                 550                 555                 560

Gln Gln Leu Leu Gly Ile Trp Gly Cys Ser Gly Lys Leu Ile Cys Cys
                565                 570                 575

Thr Ala Val Pro Trp Asn Ala Ser Trp Ser Asn Lys Thr Leu Asp Met
            580                 585                 590

Ile Trp Asn Asn Met Thr Trp Met Glu Trp Glu Arg Glu Ile Asp Asn
        595                 600                 605

Tyr Thr Gly Leu Ile Tyr Thr Leu Ile Glu Glu Ser Gln Asn Gln Gln
    610                 615                 620

Glu Lys Asn Glu Gln Glu Leu Leu Glu Leu Asp
625                 630                 635


<210> SEQ ID NO 13
<211> LENGTH: 635
<212> TYPE: PRT
<213> ORGANISM: Human immunodeficiency virus 1

<400> SEQUENCE: 13

Val Glu Asn Leu Trp Val Thr Val Tyr Tyr Gly Val Pro Val Trp Lys
1               5                   10                  15

Glu Ala Thr Thr Thr Leu Phe Cys Ala Ser Asp Ala Lys Ala Tyr Asp
            20                  25                  30
```

```
Thr Glu Val His Asn Val Trp Ala Thr His Glu Cys Val Pro Thr Asp
        35                  40                  45

Pro Asn Pro Gln Glu Val Val Leu Glu Asn Val Thr Glu Asn Phe Asn
    50                  55                  60

Met Trp Lys Asn Asn Met Val Glu Gln Met His Glu Asp Ile Ile Glu
65                  70                  75                  80

Leu Trp Asp Gln Ser Leu Lys Pro Cys Val Lys Leu Thr Pro Leu Cys
                85                  90                  95

Val Thr Leu Asn Cys Thr Asp Leu Arg Asn Val Thr Asn Ile Asn Asn
            100                 105                 110

Ser Ser Glu Gly Met Arg Gly Glu Ile Lys Asn Cys Ser Phe Asn Ile
        115                 120                 125

Thr Thr Ser Ile Arg Asp Lys Val Lys Lys Asp Tyr Ala Leu Phe Tyr
    130                 135                 140

Arg Leu Asp Val Val Pro Ile Asp Asn Asp Asn Thr Ser Tyr Arg Leu
145                 150                 155                 160

Ile Asn Cys Asn Thr Ser Thr Ile Thr Gln Ala Cys Pro Lys Val Ser
                165                 170                 175

Phe Glu Pro Ile Pro Ile His Tyr Cys Thr Pro Ala Gly Phe Ala Ile
            180                 185                 190

Leu Lys Cys Lys Asp Lys Lys Phe Asn Gly Thr Gly Pro Cys Lys Asn
        195                 200                 205

Val Ser Thr Val Gln Cys Thr His Gly Ile Arg Pro Val Val Ser Thr
    210                 215                 220

Gln Leu Leu Leu Asn Gly Ser Leu Ala Glu Glu Glu Val Ile Ile Arg
225                 230                 235                 240

Ser Ser Asn Phe Thr Asp Asn Ala Lys Asn Ile Ile Val Gln Leu Lys
                245                 250                 255

Glu Ser Val Glu Ile Asn Cys Thr Arg Pro Asn Asn Asn Thr Val Lys
            260                 265                 270

Ser Ile His Ile Gly Pro Gly Arg Ala Phe Tyr Tyr Thr Gly Asp Ile
        275                 280                 285

Ile Gly Asp Ile Arg Gln Ala His Cys Asn Ile Ser Arg Thr Lys Trp
    290                 295                 300

Asn Asn Thr Leu Asn Gln Ile Ala Thr Lys Leu Lys Glu Gln Phe Gly
305                 310                 315                 320

Asn Asn Lys Thr Ile Val Phe Asn Gln Ser Ser Gly Gly Asp Pro Glu
                325                 330                 335

Ile Val Met His Ser Phe Asn Cys Gly Gly Glu Phe Phe Tyr Cys Asn
            340                 345                 350

Ser Thr Gln Leu Phe Asn Ser Thr Trp Asn Phe Asn Gly Thr Trp Asn
        355                 360                 365

Leu Thr Gln Ser Asn Gly Thr Glu Gly Asn Asp Thr Ile Thr Leu Pro
    370                 375                 380

Cys Arg Ile Lys Gln Ile Ile Asn Met Trp Gln Glu Val Gly Lys Ala
385                 390                 395                 400

Met Tyr Ala Pro Pro Ile Arg Gly Gln Ile Arg Cys Ser Ser Asn Ile
                405                 410                 415

Thr Gly Leu Ile Leu Thr Arg Asp Gly Gly Asn Asn His Asn Asn Asp
            420                 425                 430

Thr Glu Thr Phe Arg Pro Gly Gly Gly Asp Met Arg Asp Asn Trp Arg
        435                 440                 445
```

-continued

```
Ser Glu Leu Tyr Lys Tyr Lys Val Val Lys Ile Glu Pro Leu Gly Val
    450                 455                 460

Ala Pro Thr Lys Cys Lys Arg Arg Val Val Gln Arg Arg Arg Arg Arg
465                 470                 475                 480

Arg Ala Val Gly Thr Ile Gly Ala Met Ser Leu Gly Phe Leu Gly Ala
                485                 490                 495

Ala Gly Ser Thr Met Gly Ala Ala Ser Ile Thr Leu Thr Val Gln Ala
            500                 505                 510

Arg Leu Leu Leu Ser Gly Ile Val Gln Gln Gln Asn Asn Leu Leu Arg
        515                 520                 525

Ala Pro Glu Pro Gln Gln His Leu Leu Gln Leu Thr Val Trp Gly Ile
    530                 535                 540

Lys Gln Leu Gln Ala Arg Val Leu Ala Val Glu His Tyr Leu Arg Asp
545                 550                 555                 560

Gln Gln Leu Leu Gly Ile Trp Gly Cys Ser Gly Lys Leu Ile Cys Cys
                565                 570                 575

Thr Ala Val Pro Trp Asn Ala Ser Trp Ser Asn Lys Thr Leu Asp Met
            580                 585                 590

Ile Trp Asn Asn Met Thr Trp Met Glu Trp Glu Arg Glu Ile Asp Asn
        595                 600                 605

Tyr Thr Gly Leu Ile Tyr Thr Leu Ile Glu Glu Ser Gln Asn Gln Gln
    610                 615                 620

Glu Lys Asn Glu Gln Glu Leu Leu Glu Leu Asp
625                 630                 635


<210> SEQ ID NO 14
<211> LENGTH: 634
<212> TYPE: PRT
<213> ORGANISM: Human immunodeficiency virus 1

<400> SEQUENCE: 14

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Thr Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190
```

-continued

```
Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Met Ile Arg Ser Glu Asn Ile Thr Asn Asn Ala Lys Asn Ile Leu Val
                245                 250                 255

Gln Phe Asn Thr Pro Val Gln Ile Asn Cys Thr Arg Pro Asn Asn Asn
            260                 265                 270

Thr Arg Lys Ser Ile Arg Ile Gly Pro Gly Gln Ala Phe Tyr Ala Thr
        275                 280                 285

Gly Asp Ile Ile Gly Asp Ile Arg Gln Ala His Cys Asn Val Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Asn Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Phe Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Gln Ser Asn Leu Leu Arg Ala
        515                 520                 525

Pro Glu Ala Gln Gln His Leu Leu Lys Leu Thr Val Trp Gly Ile Lys
    530                 535                 540

Gln Leu Gln Ala Arg Val Leu Ala Val Glu Arg Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
            580                 585                 590

Trp Asp Asn Met Thr Trp Leu Gln Trp Asp Lys Glu Ile Ser Asn Tyr
        595                 600                 605
```

-continued

```
Thr Gln Ile Ile Tyr Gly Leu Leu Glu Glu Ser Gln Asn Gln Gln Glu
    610                 615                 620

Lys Asn Glu Gln Asp Leu Leu Ala Leu Asp
625                 630


<210> SEQ ID NO 15
<211> LENGTH: 634
<212> TYPE: PRT
<213> ORGANISM: Human immunodeficiency virus 1

<400> SEQUENCE: 15

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Ile Ile Arg Ser Glu Asn Ile Thr Asn Asn Ala Lys Asn Ile Leu Val
                245                 250                 255

Gln Leu Asn Thr Pro Val Gln Ile Asn Cys Thr Arg Pro Asn Asn Asn
            260                 265                 270

Thr Val Lys Ser Ile Arg Ile Gly Pro Gly Gln Ala Phe Tyr Tyr Thr
        275                 280                 285

Gly Asp Ile Ile Gly Asp Ile Arg Gln Ala His Cys Asn Val Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Glu Phe Phe
            340                 345                 350
```

-continued

```
Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Ser Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Gln Ser Asn Leu Leu Arg Ala
        515                 520                 525

Pro Glu Pro Gln Gln His Leu Leu Lys Asp Thr His Trp Gly Ile Lys
    530                 535                 540

Gln Leu Gln Ala Arg Val Leu Ala Val Glu His Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
            580                 585                 590

Trp Asp Asn Met Thr Trp Leu Gln Trp Asp Lys Glu Ile Ser Asn Tyr
        595                 600                 605

Thr Gln Ile Ile Tyr Gly Leu Leu Glu Glu Ser Gln Asn Gln Gln Glu
    610                 615                 620

Lys Asn Glu Gln Asp Leu Leu Ala Leu Asp
625                 630
```

<210> SEQ ID NO 16
<211> LENGTH: 637
<212> TYPE: PRT
<213> ORGANISM: Human immunodeficiency virus 1

<400> SEQUENCE: 16

```
Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Ser Ser Glu Ile His Leu Glu Asn Val Thr Glu Glu Phe Asn
    50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
```

```
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Gln Asn Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Ile Ile Arg Ser Glu Asn Ile Thr Asn Asn Ala Lys Asn Ile Leu Val
                245                 250                 255

Gln Leu Asn Thr Ser Val Gln Ile Asn Cys Thr Arg Pro Asn Asn Asn
            260                 265                 270

Thr Val Lys Ser Ile Arg Ile Gly Pro Gly Gln Ala Phe Tyr Tyr Thr
        275                 280                 285

Gly Asp Ile Ile Gly Asp Ile Arg Gln Ala His Cys Asn Val Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Ser Leu Gly Phe Leu Gly Ala Ala
                485                 490                 495

Gly Ser Thr Met Gly Ala Ala Ser Met Thr Leu Thr Val Gln Ala Arg
            500                 505                 510
```

```
Asn Leu Leu Ser Gly Ile Val Gln Gln Gln Ser Asn Leu Leu Arg Ala
        515                 520                 525

Pro Glu Pro Gln Gln His Leu Leu Lys Asp Thr His Trp Gly Ile Lys
    530                 535                 540

Gln Leu Gln Ala Arg Val Leu Ala Val Glu His Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Ala Asn Leu Ser Glu Ile
            580                 585                 590

Trp Asp Asn Met Thr Trp Leu Gln Trp Asp Lys Glu Ile Ser Asn Tyr
        595                 600                 605

Thr Gln Ile Ile Tyr Gly Leu Leu Glu Glu Ser Gln Asn Gln Asn Glu
    610                 615                 620

Ser Asn Glu Gln Asp Leu Leu Ala Leu Asp Asn Gly Ser
625                 630                 635


<210> SEQ ID NO 17
<211> LENGTH: 637
<212> TYPE: PRT
<213> ORGANISM: Human immunodeficiency virus 1

<400> SEQUENCE: 17

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Ser Ser Glu Ile His Leu Glu Asn Val Thr Glu Glu Phe Asn
    50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Gln Asn Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Ile Ile Arg Ser Glu Asn Ile Thr Asn Asn Ala Lys Asn Ile Leu Val
```

-continued

```
                245                 250                 255

Gln Leu Asn Thr Ser Val Gln Ile Asn Cys Thr Arg Pro Asn Asn Asn
            260                 265                 270

Thr Val Lys Ser Ile Arg Ile Gly Pro Gly Gln Ala Phe Tyr Tyr Thr
        275                 280                 285

Gly Asp Ile Ile Gly Asp Ile Arg Gln Ala His Cys Asn Val Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Ser Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Gln Ser Asn Leu Leu Arg Ala
        515                 520                 525

Pro Glu Pro Gln Gln His Leu Leu Lys Asp Thr His Trp Gly Ile Lys
    530                 535                 540

Gln Leu Gln Ala Arg Val Leu Ala Val Glu His Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
            580                 585                 590

Trp Asp Asn Met Thr Trp Leu Asn Trp Ser Lys Glu Ile Ser Asn Tyr
        595                 600                 605

Thr Gln Ile Ile Tyr Gly Leu Leu Glu Glu Ser Gln Asn Gln Gln Glu
    610                 615                 620

Lys Asn Asn Gln Ser Leu Leu Ala Leu Asp Asn Gly Ser
625                 630                 635


<210> SEQ ID NO 18
<211> LENGTH: 634
<212> TYPE: PRT
<213> ORGANISM: Human immunodeficiency virus 1
```

<400> SEQUENCE: 18

Ala Glu Asn Leu Trp Val Thr Val Tyr Tyr Gly Val Pro Val Trp Lys
1 5 10 15

Asp Ala Glu Thr Thr Leu Phe Cys Ala Ser Asp Ala Lys Ala Tyr Glu
20 25 30

Thr Glu Lys His Asn Val Trp Ala Thr His Ala Cys Val Pro Thr Asp
35 40 45

Pro Asn Pro Gln Glu Ile His Leu Glu Asn Val Thr Glu Glu Phe Asn
50 55 60

Met Trp Lys Asn Asn Met Val Glu Gln Met His Glu Asp Ile Ile Ser
65 70 75 80

Leu Trp Asp Gln Ser Leu Lys Pro Cys Cys Lys Leu Thr Pro Leu Cys
85 90 95

Val Thr Leu Gln Cys Thr Asn Val Thr Asn Asn Ile Thr Asp Asp Met
100 105 110

Arg Gly Glu Leu Lys Asn Cys Ser Phe Asn Met Thr Thr Glu Leu Arg
115 120 125

Asp Lys Lys Gln Lys Val Tyr Ser Leu Phe Tyr Arg Leu Asp Val Val
130 135 140

Gln Ile Asn Glu Asn Gln Gly Asn Arg Ser Asn Asn Ser Asn Lys Glu
145 150 155 160

Tyr Arg Leu Ile Asn Cys Asn Thr Ser Ala Cys Thr Gln Ala Cys Pro
165 170 175

Lys Val Ser Phe Glu Pro Ile Pro Ile His Tyr Cys Ala Pro Ala Gly
180 185 190

Phe Ala Ile Leu Lys Cys Lys Asp Lys Lys Phe Asn Gly Thr Gly Pro
195 200 205

Cys Pro Ser Val Ser Thr Val Gln Cys Thr His Gly Ile Lys Pro Val
210 215 220

Val Ser Thr Gln Leu Leu Leu Asn Gly Ser Leu Ala Glu Glu Glu Val
225 230 235 240

Ile Ile Arg Ser Glu Asn Ile Thr Asn Asn Ala Lys Asn Ile Leu Val
245 250 255

Gln Leu Asn Thr Pro Val Gln Ile Asn Cys Thr Arg Pro Asn Asn Asn
260 265 270

Thr Arg Lys Ser Ile Arg Ile Gly Pro Gly Cys Ala Phe Tyr Ala Thr
275 280 285

Gly Asp Ile Ile Gly Asp Ile Arg Gln Ala His Cys Asn Val Ser Lys
290 295 300

Ala Thr Trp Asn Glu Thr Leu Gly Lys Val Val Lys Gln Leu Arg Lys
305 310 315 320

His Phe Gly Asn Asn Thr Ile Ile Arg Phe Ala Gln Ser Ser Gly Gly
325 330 335

Asp Leu Glu Val Thr Thr His Ser Phe Asn Cys Gly Gly Glu Phe Phe
340 345 350

Tyr Cys Asn Thr Ser Gly Leu Phe Asn Ser Thr Trp Ile Ser Asn Thr
355 360 365

Ser Val Gln Gly Ser Asn Ser Thr Gly Ser Asn Asp Ser Ile Thr Leu
370 375 380

Pro Cys Arg Ile Lys Gln Ile Ile Asn Met Trp Gln Arg Ile Gly Gln
385 390 395 400

Cys Met Tyr Ala Pro Pro Ile Gln Gly Val Ile Arg Cys Val Ser Asn

```
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Ser Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Gln Ser Asn Leu Leu Arg Ala
        515                 520                 525

Pro Glu Pro Gln Glu His Leu His Lys Asp Thr His Trp Gly Ile Lys
    530                 535                 540

Gln Leu Gln Ala Arg Val Leu Ala Val Glu His Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
            580                 585                 590

Trp Asp Asn Met Thr Trp Leu Gln Trp Asp Lys Glu Ile Ser Asn Tyr
        595                 600                 605

Thr Gln Ile Ile Tyr Gly Leu Leu Glu Glu Ser Gln Asn Gln Gln Glu
    610                 615                 620

Lys Asn Glu Gln Asp Leu Leu Ala Leu Asp
625                 630
```

<210> SEQ ID NO 19
<211> LENGTH: 634
<212> TYPE: PRT
<213> ORGANISM: Human immunodeficiency virus 1

<400> SEQUENCE: 19

```
Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Glu Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Thr Asp Ile Ile Glu
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140
```

```
Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Ile Ile Arg Ser Glu Asn Ile Thr Asn Asn Ala Lys Asn Ile Leu Val
                245                 250                 255

Gln Leu Asn Thr Pro Val Gln Ile Asn Cys Thr Arg Pro Asn Asn Asn
            260                 265                 270

Thr Val Lys Ser Ile Arg Ile Gly Pro Gly Gln Ala Phe Tyr Tyr Thr
        275                 280                 285

Gly Asp Ile Ile Gly Asp Ile Arg Gln Ala His Cys Asn Val Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Ser Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Gln Ser Asn Leu Leu Arg Ala
        515                 520                 525

Pro Glu Pro Gln Gln His Leu Leu Lys Leu Thr Val Trp Gly Ile Lys
    530                 535                 540

Gln Leu Gln Ala Arg Val Leu Ala Val Glu His Tyr Leu Arg Asp Gln
545                 550                 555                 560

Gln Leu Leu Gly Ile Trp Gly Cys Ser Gly Lys Leu Ile Cys Cys Thr
```

```
                565                 570                 575

Asn Val Pro Trp Asn Ser Ser Trp Ser Asn Arg Asn Leu Ser Glu Ile
            580                 585                 590

Trp Asp Asn Met Thr Trp Leu Gln Trp Asp Lys Glu Ile Ser Asn Tyr
        595                 600                 605

Thr Gln Ile Ile Tyr Gly Leu Leu Glu Glu Ser Gln Asn Gln Gln Glu
    610                 615                 620

Lys Asn Glu Gln Asp Leu Leu Ala Leu Asp
625                 630


<210> SEQ ID NO 20
<211> LENGTH: 634
<212> TYPE: PRT
<213> ORGANISM: Human immunodeficiency virus 1

<400> SEQUENCE: 20

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Trp Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Ile Ile Arg Ser Glu Asn Ile Thr Asn Asn Ala Lys Asn Ile Leu Val
                245                 250                 255

Gln Leu Asn Thr Pro Val Gln Ile Asn Cys Thr Ala Pro Asn Asn Phe
            260                 265                 270

Thr Val Lys Ser Ile Arg Ile Gly Pro Gly Gln Ala Phe Tyr Tyr Met
        275                 280                 285

Gly Asp Ile Ile Gly Asp Ile Arg Gln Ala His Cys Asn Val Ser Lys
    290                 295                 300
```

```
Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Met Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
    370                 375                 380

Pro Cys Arg Ile Lys Leu Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Ser Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Gln Ser Asn Leu Leu Arg Ala
        515                 520                 525

Pro Glu Pro Gln Gln His Leu Leu Lys Asp Thr His Trp Gly Ile Lys
    530                 535                 540

Gln Leu Gln Ala Arg Val Leu Ala Val Glu His Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
            580                 585                 590

Trp Asp Asn Met Thr Trp Leu Gln Trp Asp Lys Glu Ile Ser Asn Tyr
        595                 600                 605

Thr Gln Ile Ile Tyr Gly Leu Leu Glu Glu Ser Gln Asn Gln Gln Glu
    610                 615                 620

Lys Asn Glu Gln Asp Leu Leu Ala Leu Asp
625                 630
```

<210> SEQ ID NO 21
<211> LENGTH: 634
<212> TYPE: PRT
<213> ORGANISM: Human immunodeficiency virus 1

<400> SEQUENCE: 21

```
Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45
```

-continued

```
Pro Asn Pro Gln Glu Ile His Leu Glu Asn Val Thr Glu Glu Phe Asn
    50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Trp Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Ile Ile Arg Ser Glu Asn Ile Thr Asn Asn Ala Lys Asn Ile Leu Val
                245                 250                 255

Gln Leu Asn Thr Pro Val Gln Ile Asn Cys Thr Ala Pro Asn Asn Phe
            260                 265                 270

Thr Val Lys Ser Ile Arg Ile Gly Pro Gly Gln Ala Phe Tyr Tyr Met
        275                 280                 285

Gly Asp Ile Ile Gly Asp Ile Arg Gln Ala His Cys Asn Val Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Met Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
    370                 375                 380

Pro Cys Arg Ile Lys Leu Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Thr Asp Met Arg Asp Asn Trp Arg
        435                 440                 445

Ser Glu Leu Tyr Lys Tyr Lys Val Val Lys Ile Glu Pro Leu Gly Val
    450                 455                 460
```

-continued

Ala Pro Thr Arg Cys Lys Arg Arg Val Val Gly Arg Arg Arg Arg Arg
465 470 475 480

Arg Ala Val Gly Ile Gly Ala Val Ser Leu Gly Phe Leu Gly Ala Ala
485 490 495

Gly Ser Thr Met Gly Ala Ala Ser Met Thr Leu Thr Val Gln Ala Arg
500 505 510

Asn Leu Leu Ser Gly Ile Val Gln Gln Gln Ser Asn Leu Leu Arg Ala
515 520 525

Pro Glu Pro Gln Gln His Leu Leu Lys Asp Thr His Trp Gly Ile Lys
530 535 540

Gln Leu Gln Ala Arg Val Leu Ala Val Glu His Tyr Leu Arg Asp Gln
545 550 555 560

Gln Leu Leu Gly Ile Trp Gly Cys Ser Gly Lys Leu Ile Cys Cys Thr
565 570 575

Asn Val Pro Trp Asn Ser Ser Trp Ser Asn Arg Asn Leu Ser Glu Ile
580 585 590

Trp Asp Asn Met Thr Trp Leu Gln Trp Asp Lys Glu Ile Ser Asn Tyr
595 600 605

Thr Gln Ile Ile Tyr Gly Leu Leu Glu Glu Ser Gln Asn Gln Gln Glu
610 615 620

Lys Asn Glu Gln Asp Leu Leu Ala Leu Asp
625 630

<210> SEQ ID NO 22
<211> LENGTH: 706
<212> TYPE: PRT
<213> ORGANISM: Human gammaherpesvirus 4

<400> SEQUENCE: 22

Met Gln Leu Leu Cys Val Phe Cys Leu Val Leu Leu Trp Glu Val Gly
1 5 10 15

Ala Ala Ser Leu Ser Glu Val Lys Leu His Leu Asp Ile Glu Gly His
20 25 30

Ala Ser His Tyr Thr Ile Pro Trp Thr Glu Leu Met Ala Lys Val Pro
35 40 45

Gly Leu Ser Pro Glu Ala Leu Trp Arg Glu Ala Asn Val Thr Glu Asp
50 55 60

Leu Ala Ser Met Leu Asn Arg Tyr Lys Leu Ile Tyr Lys Thr Ser Gly
65 70 75 80

Thr Leu Gly Ile Ala Leu Ala Glu Pro Val Asp Ile Pro Ala Val Ser
85 90 95

Glu Gly Ser Met Gln Val Asp Ala Ser Lys Val His Pro Gly Val Ile
100 105 110

Ser Gly Leu Asn Ser Pro Ala Cys Met Leu Ser Ala Pro Leu Glu Lys
115 120 125

Gln Leu Phe Tyr Tyr Ile Gly Thr Met Leu Pro Asn Thr Arg Pro His
130 135 140

Ser Tyr Val Phe Tyr Gln Leu Arg Cys His Leu Ser Tyr Val Ala Leu
145 150 155 160

Ser Ile Asn Gly Asp Lys Phe Gln Tyr Thr Gly Ala Met Thr Ser Lys
165 170 175

Phe Leu Met Gly Thr Tyr Lys Arg Val Thr Glu Lys Gly Asp Glu His
180 185 190

Val Leu Ser Leu Val Phe Gly Lys Thr Lys Asp Leu Pro Asp Leu Arg
195 200 205

-continued

```
Gly Pro Phe Ser Tyr Pro Ser Leu Thr Ser Ala Gln Ser Gly Asp Tyr
    210                 215                 220

Ser Leu Val Ile Val Thr Thr Phe Val His Tyr Ala Asn Phe His Asn
225                 230                 235                 240

Tyr Phe Val Pro Asn Leu Lys Asp Met Phe Ser Arg Ala Val Thr Met
                245                 250                 255

Thr Ala Ala Ser Tyr Ala Arg Tyr Val Leu Gln Lys Leu Val Leu Leu
            260                 265                 270

Glu Met Lys Gly Gly Cys Arg Glu Pro Glu Leu Asp Thr Glu Thr Leu
        275                 280                 285

Thr Thr Met Phe Glu Val Ser Val Ala Phe Phe Lys Val Gly His Ala
    290                 295                 300

Val Gly Glu Thr Gly Asn Gly Cys Val Asp Leu Arg Trp Leu Ala Lys
305                 310                 315                 320

Ser Phe Phe Glu Leu Thr Val Leu Lys Asp Ile Ile Gly Ile Cys Tyr
                325                 330                 335

Gly Ala Thr Val Lys Gly Met Gln Ser Tyr Gly Leu Glu Arg Leu Ala
            340                 345                 350

Ala Met Leu Met Ala Thr Val Lys Met Glu Glu Leu Gly His Leu Thr
        355                 360                 365

Thr Glu Lys Gln Glu Tyr Ala Leu Arg Leu Ala Thr Val Gly Tyr Pro
    370                 375                 380

Lys Ala Gly Val Tyr Ser Gly Leu Ile Gly Gly Ala Thr Ser Val Leu
385                 390                 395                 400

Leu Ser Ala Tyr Asn Arg His Pro Leu Phe Gln Pro Leu His Thr Val
                405                 410                 415

Met Arg Glu Thr Leu Phe Ile Gly Ser His Val Val Leu Arg Glu Leu
            420                 425                 430

Arg Leu Asn Val Thr Thr Gln Gly Pro Asn Leu Ala Leu Tyr Gln Leu
        435                 440                 445

Leu Ser Thr Ala Leu Cys Ser Ala Leu Glu Ile Gly Glu Val Leu Arg
    450                 455                 460

Gly Leu Ala Leu Gly Thr Glu Ser Gly Leu Phe Ser Pro Cys Tyr Leu
465                 470                 475                 480

Ser Leu Arg Phe Asp Leu Thr Arg Asp Lys Leu Leu Ser Met Ala Pro
                485                 490                 495

Gln Glu Ala Thr Leu Asp Gln Ala Ala Val Ser Asn Ala Val Asp Gly
            500                 505                 510

Phe Leu Gly Arg Leu Ser Leu Glu Arg Glu Asp Arg Asp Ala Trp His
        515                 520                 525

Leu Pro Ala Tyr Lys Cys Val Asp Arg Leu Asp Lys Val Leu Met Ile
    530                 535                 540

Ile Pro Leu Ile Asn Val Thr Phe Ile Ile Ser Ser Asp Arg Glu Val
545                 550                 555                 560

Arg Gly Ser Ala Leu Tyr Glu Ala Ser Thr Thr Tyr Leu Ser Ser Ser
                565                 570                 575

Leu Phe Leu Ser Pro Val Ile Met Asn Lys Cys Ser Gln Gly Ala Val
            580                 585                 590

Ala Gly Glu Pro Arg Gln Ile Pro Lys Ile Gln Asn Phe Thr Arg Thr
        595                 600                 605

Gln Lys Ser Cys Ile Phe Cys Gly Phe Ala Leu Leu Ser Tyr Asp Glu
    610                 615                 620
```

```
Lys Glu Gly Leu Glu Thr Thr Thr Tyr Ile Thr Ser Gln Glu Val Gln
625                 630                 635                 640

Asn Ser Ile Leu Ser Ser Asn Tyr Phe Asp Phe Asp Asn Leu His Val
                645                 650                 655

His Tyr Leu Leu Leu Thr Thr Asn Gly Thr Val Met Glu Ile Ala Gly
            660                 665                 670

Leu Tyr Glu Glu Arg Ala His Val Val Leu Ala Ile Ile Leu Tyr Phe
        675                 680                 685

Ile Ala Phe Ala Leu Gly Ile Phe Leu Val His Lys Ile Val Met Phe
    690                 695                 700

Phe Leu
705


<210> SEQ ID NO 23
<211> LENGTH: 137
<212> TYPE: PRT
<213> ORGANISM: Human gammaherpesvirus 4

<400> SEQUENCE: 23

Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Leu Ala Leu Glu Asn Ile Ser Asp Ile
        35                  40                  45

Tyr Leu Val Ser Asn Gln Thr Cys Asp Gly Phe Ser Leu Ala Ser Leu
    50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
                85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Tyr Ala Trp His Arg Gly Gly
    130                 135


<210> SEQ ID NO 24
<211> LENGTH: 223
<212> TYPE: PRT
<213> ORGANISM: Human gammaherpesvirus 4

<400> SEQUENCE: 24

Met Val Ser Phe Lys Gln Val Arg Val Pro Leu Phe Thr Ala Ile Ala
1               5                   10                  15

Leu Val Ile Val Leu Leu Leu Ala Tyr Phe Leu Pro Pro Arg Val Arg
            20                  25                  30

Gly Gly Gly Arg Val Ala Ala Ala Ala Ile Thr Trp Val Pro Lys Pro
        35                  40                  45

Asn Val Glu Val Trp Pro Val Asp Pro Pro Pro Pro Val Asn Phe Asn
    50                  55                  60

Lys Thr Ala Glu Gln Glu Tyr Gly Asp Lys Glu Val Lys Leu Pro His
65                  70                  75                  80

Trp Thr Pro Thr Leu His Thr Phe Gln Val Pro Gln Asn Tyr Thr Lys
                85                  90                  95
```

```
Ala Asn Cys Thr Tyr Cys Asn Thr Arg Glu Tyr Thr Phe Ser Tyr Lys
            100                 105                 110

Gly Cys Cys Phe Tyr Phe Thr Lys Lys Lys His Thr Trp Asn Gly Cys
        115                 120                 125

Phe Gln Ala Cys Ala Glu Leu Tyr Pro Cys Thr Tyr Phe Tyr Gly Pro
    130                 135                 140

Thr Pro Asp Ile Leu Pro Val Val Thr Arg Asn Leu Asn Ala Ile Glu
145                 150                 155                 160

Ser Leu Trp Val Gly Val Tyr Arg Val Gly Glu Gly Asn Trp Thr Ser
                165                 170                 175

Leu Asp Gly Gly Thr Phe Lys Val Tyr Gln Ile Phe Gly Ser His Cys
            180                 185                 190

Thr Tyr Val Ser Lys Phe Ser Thr Val Pro Val Ser His His Glu Cys
        195                 200                 205

Ser Phe Leu Lys Pro Cys Leu Cys Val Ser Gln Arg Ser Asn Ser
    210                 215                 220


<210> SEQ ID NO 25
<211> LENGTH: 602
<212> TYPE: PRT
<213> ORGANISM: Unknown
<220> FEATURE:
<223> OTHER INFORMATION: Description of Unknown:
      RSV sequence

<400> SEQUENCE: 25

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240
```

-continued

```
Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Glu Asn Leu Tyr Phe Gln Ser Ser Ala Trp Ser His Pro Gln Phe Glu
545                 550                 555                 560

Lys Gly Gly Gly Ser Gly Gly Gly Ser Gly Gly Ser Ala Trp Ser His
                565                 570                 575

Pro Gln Phe Glu Lys Gly Ser Gly Ser Gly Ser Gly Leu Asn Asp Ile
            580                 585                 590

Phe Glu Ala Gln Lys Ile Glu Trp His Glu
        595                 600
```

<210> SEQ ID NO 26
<211> LENGTH: 576
<212> TYPE: PRT
<213> ORGANISM: Unknown
<220> FEATURE:
<223> OTHER INFORMATION: Description of Unknown:
RSV sequence

<400> SEQUENCE: 26

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415
```

```
Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Leu Tyr Val Lys Gly Glu Pro Ile Ile Asn Phe Tyr Asp Pro Leu
465                 470                 475                 480

Val Phe Pro Ser Asp Glu Phe Asp Ala Ser Ile Ser Gln Val Asn Glu
                485                 490                 495

Lys Ile Asn Gln Ser Leu Ala Phe Ile Arg Lys Ser Asp Glu Leu Leu
            500                 505                 510

His Asn Val Asn Ala Val Glu Asn Leu Tyr Phe Gln Ser Ser Ala Trp
        515                 520                 525

Ser His Pro Gln Phe Glu Lys Gly Gly Gly Ser Gly Gly Gly Ser Gly
    530                 535                 540

Gly Ser Ala Trp Ser His Pro Gln Phe Glu Lys Gly Ser Gly Ser Gly
545                 550                 555                 560

Ser Gly Leu Asn Asp Ile Phe Glu Ala Gln Lys Ile Glu Trp His Glu
                565                 570                 575


<210> SEQ ID NO 27
<211> LENGTH: 574
<212> TYPE: PRT
<213> ORGANISM: Unknown
<220> FEATURE:
<223> OTHER INFORMATION: Description of Unknown:
      RSV sequence

<400> SEQUENCE: 27

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Pro Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
```

```
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Ile Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Met Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Met Lys Trp Val Thr Phe Ile Ser Leu Leu Phe Leu Phe Ser Ser Ala
1 5 10 15

Tyr Ser

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 29

Met Val Leu Gln Thr Gln Val Phe Ile Ser Leu Leu Leu Trp Ile Ser
1 5 10 15

Gly Ala Tyr Gly
20

<210> SEQ ID NO 30
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Met Gln Met Ser Pro Ala Leu Thr Cys Leu Val Leu Gly Leu Ala Leu
1 5 10 15

Val Phe Gly Glu Gly Ser Ala
20

<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

Met Gly Leu Ala Trp Gly Leu Gly Val Leu Phe Leu Met His Val Cys
1 5 10 15

Gly Thr

<210> SEQ ID NO 32
<211> LENGTH: 31
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

Met Leu Arg Gly Pro Gly Pro Gly Leu Leu Leu Leu Ala Val Gln Cys
1 5 10 15

Leu Gly Thr Ala Val Pro Ser Thr Gly Ala Ser Lys Ser Lys Arg
20 25 30

<210> SEQ ID NO 33
<211> LENGTH: 29
<212> TYPE: PRT

<213> ORGANISM: Artificial Sequence
<220> FEATURE:
<223> OTHER INFORMATION: Description of Artificial Sequence: Synthetic peptide

<400> SEQUENCE: 33

Met Ala Gly Arg Ser His Pro Gly Pro Leu Arg Pro Leu Leu Pro Leu
1 5 10 15

Leu Val Val Ala Ala Cys Val Leu Pro Gly Ala Gly Gly
20 25

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Met Glu Phe Gly Leu Ser Trp Val Phe Leu Val Ala Leu Phe Arg Gly
1 5 10 15

Val Gln Cys

<210> SEQ ID NO 35
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Met Lys Tyr Leu Leu Pro Thr Ala Ala Ala Gly Leu Leu Leu Leu Ala
1 5 10 15

Ala Gln Pro Ala Met Ala
20

<210> SEQ ID NO 36
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Met Arg Pro Thr Trp Ala Trp Trp Leu Phe Leu Val Leu Leu Leu Ala
1 5 10 15

Leu Trp Ala Pro Ala Arg Gly
20

<210> SEQ ID NO 37
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Met Trp Trp Arg Leu Trp Trp Leu Leu Leu Leu Leu Leu Leu Leu Trp
1 5 10 15

Pro Met Val Trp Ala
20

-continued

```
<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Met Gly Val Lys Val Leu Phe Ala Leu Ile Cys Ile Ala Val Ala Glu
1               5                   10                  15

Ala


<210> SEQ ID NO 39
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Met Pro Ser Ser Val Ser Trp Gly Ile Leu Leu Leu Ala Gly Leu Cys
1               5                   10                  15

Cys Leu Val Pro Val Ser Leu Ala
            20


<210> SEQ ID NO 40
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Met His Ser Ser Ala Leu Leu Cys Cys Leu Val Leu Leu Thr Gly Val
1               5                   10                  15

Arg Ala
```

COMPOSITIONS, DEVICES AND METHODS FOR INDUCING IMMUNE RESPONSES TO INFECTIOUS AGENTS

CLAIM OF PRIORITY

This application is a U.S. national phase application and claims the benefit of priority under 35 U.S.C § 371 of International Application No. PCT/US2021/030725, filed on May 4, 2021, which claims priority to U.S. Provisional Application No. 63/019,825, filed May 4, 2020. The disclosure of each of the foregoing applications is incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 15, 2021, is named S2225-7036WO (SG-WO-003)_SL.txt and is 141,723 bytes in size.

BACKGROUND

Infectious agents such as viruses & bacteria pose a significant threat to the individual. Natural immunity to these organisms relies on the development of a robust adaptive immune response which includes the production of neutralizing antibodies produced by B cells. The development of such neutralizing antibodies is a stochastic process which is determined not only by the nature of proteins produced by the infectious agent but also genetic variations in the individuals and the pre-existing repertoire of B cell and T cell receptors.

Many vaccines in clinical use consist of an inactivated or live attenuated organism that cannot cause disease. While such whole-organism vaccines can elicit immune responses, they don't provide protective immunity for every infectious organism.

Another vaccination approach employs subunit vaccines, which contain antigenic components of the infectious agent that best stimulate the immune system. While this approach can make a vaccine safer and easier to produce, it typically requires inclusion of adjuvants because the antigens alone are not sufficient to induce adequate long-term immunity.

An investigational approach to vaccination involves administering nucleic acid molecules (DNA or RNA) encoding the antigen or antigens against which an immune response is sought. The nucleic acid enters the recipient's cells which produce and secrete the antigens. One risk involved in this approach is that the modification of the recipient's own cells may be difficult to reverse in the event of unforeseen side effects.

SUMMARY

Described herein is an implantable device that contains cells (e.g., allogenic to the recipient) engineered to express and secrete one or more antigens of an infectious agent, or multiple infectious agents, when the device is implanted into a recipient. The device is configured to prevent immune cells from contacting the antigen-expressing cells and prevent the antigen-expressing cells from exiting the device while allowing continuous delivery (e.g., exit) of the secreted antigen(s) from the device in an amount and for a time period that is sufficient to induce a protective immune response to the infectious agent(s). The continuous antigen delivery that is achieved by the device has the potential to result in the expansion and development of a polyclonal B cell response leading to the production of a broad spectrum of neutralizing antibodies specific for the targeted infectious agent(s). In an embodiment, the cells in the device are engineered to express and secrete one or more antigens for a coronavirus (e.g., a coronavirus that infects humans, e.g., respiratory syndrome coronavirus 2 (SARS-COV-2), SARS-associated coronavirus (SARS-COV), MERS-associated coronavirus), a Human Immunodeficiency Virus (e.g., HIV-1), an Epstein Barr Virus (EBV), or a Respiratory Syncytial Virus (RSV).

In an embodiment, the device also comprises cells engineered to express and secrete one or more immunomodulatory agents that enhance the protective immune response. For example, the immunomodulatory agent is selected to promote one of more of the following immune responses: generation of follicular helper T ($T_{FH}$) cells specific for the antigen, generation of memory B cells, and differentiation of antibody secreting cells into long-lived plasma cells. In an embodiment, the antigen-expressing cells in the device are derived from ARPE-19 cells, which endogenously express interleukin 6 (IL-6) and monocyte chemoattractant protein (MCP-1), two proteins known to augment B cell responses.

In an embodiment, the surface of the device comprises a compound or polymer that mitigates the foreign body response (FBR) to the device (e.g., a compound or polymer with an afibrotic property as defined herein, e.g., an afibrotic compound or afibrotic polymer). In an embodiment, an afibrotic polymer comprises a biocompatible, zwitterionic polymer, e.g., as described in WO 2017/218507, WO 2018/140834, or Liu et al., Zwitterionically modified alginates mitigate cellular overgrowth for cell encapsulation, Nature Communications (2019)10:5262. In an embodiment, the compound is a compound of Formula (I):

(I)

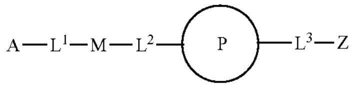

or a pharmaceutically acceptable salt thereof, wherein the variables A, $L^1$, M, $L^2$, P, $L^3$, and Z, as well as related subvariables, are defined herein.

In an embodiment, the device is configured as a two-compartment hydrogel capsule in which an inner compartment comprising the cells expressing antigen(s) and any immunomodulatory agent(s) is completely surrounded by a barrier compartment. In some embodiments, the barrier compartment comprises a polymer covalently modified with a compound that mitigates the foreign body response (FBR) to the device.

In an embodiment, a device described herein is combined with a pharmaceutically acceptable excipient to prepare a device preparation or a composition, e.g., a vaccine composition, which may be implanted into a subject to induce a neutralizing antibody response to an infectious agent.

BRIEF DESCRIPTION OF THE DRAWINGS

FIGS. 1A to 1G show amino acid sequences of exemplary SARS-COV-2 antigens.

FIGS. 2A to 2M show amino acid sequences of exemplary HIV-1 antigens.

FIGS. 3A to 3C show amino acid sequences of exemplary EBV antigens.

FIGS. 4A to 4C show amino acid sequences of exemplary RSV antigens.

DETAILED DESCRIPTION

Figure 5A:
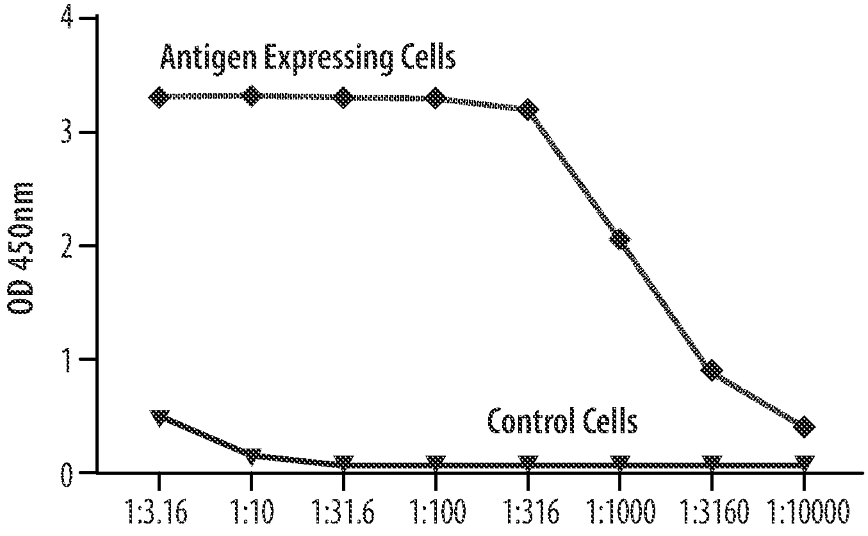
FIGS. 5A and 5B illustrate the production of antigen-specific antibodies in mice implanted with an exemplary device described herein, at both 3 weeks (FIG. 5A) and 7 weeks (FIG. 5B) post-implantation.

The present disclosure features an implantable device capable of continuous delivery of antigens of an infectious agent to a subject in an amount and for a time period sufficient to induce a protective immune response to the infectious agent. The antigens are expressed and secreted by living cells contained in the device. A variety of device configurations and their use for inducing immune response against a variety of infectious agents are contemplated by the present disclosure. Various embodiments will be described below.

Abbreviations and Definitions

Throughout the detailed description and examples of the disclosure the following abbreviations will be used.

CM-Alg chemically modified alginate

CM-LMW-Alg chemically modified, low molecular weight alginate

CM-LMW-Alg-101 low molecular weight alginate, chemically modified with Compound 101 shown in Table 4

CM-HMW-Alg chemically modified, high molecular weight alginate

CM-HMW-Alg-101 high molecular weight alginate, chemically modified with Compound 101 shown in Table 4

CM-MMW-Alg chemically modified, medium molecular weight alginate

CM-MMW-Alg-101 medium molecular weight alginate, chemically modified with Compound 101 shown in Table 4

HMW-Alg high molecular weight alginate

MMW-Alg medium molecular weight alginate

U-Alg unmodified alginate

U-HMW-Alg unmodified high molecular weight alginate

U-LMW-Alg unmodified low molecular weight alginate

U-MMW-Alg unmodified medium molecular weight alginate

70:30 CM-Alg: U-Alg 70:30 mixture (V: V) of a chemically modified alginate and an unmodified alginate, e.g., as described in WO2020069429.

Definitions

So that the disclosure may be more readily understood, certain technical and scientific terms used herein are specifically defined below. Unless specifically defined elsewhere in this document, all other technical and scientific terms used herein have the meaning commonly understood by one of ordinary skill in the art to which this disclosure belongs.

As used herein, including the appended claims, the singular forms of words such as "a," "an," and "the," include their corresponding plural references unless the context clearly dictates otherwise.

"About" or "approximately" means when used herein to modify a numerically defined parameter (e.g., a physical description of a hydrogel capsule such as diameter, sphericity, number of cells encapsulated therein, the number of capsules in a preparation), means that the recited numerical value is within an acceptable functional range for the defined parameter as determined by one of ordinary skill in the art, which will depend in part on how the numerical value is measured or determined, e.g., the limitations of the measurement system, including the acceptable error range for that measurement system. For example, "about" can mean a range of 20% above and below the recited numerical value. As a non-limiting example, a hydrogel capsule defined as having a diameter of about 1.5 millimeters (mm) and encapsulating about 5 million (M) cells may have a diameter of 1.2 to 1.8 mm and may encapsulate 4 M to 6 M cells. As another non-limiting example, a preparation of about 100 devices (e.g., hydrogel capsules) includes preparations having 80 to 120 devices. In some embodiments, the term "about" means that the modified parameter may vary by as much as 15%, 10% or 5% above and below the stated numerical value for that parameter.

"Acquire" or "acquiring", as used herein, refer to obtaining possession of a value, e.g., a numerical value, or image, or a physical entity (e.g., a sample), by "directly acquiring" or "indirectly acquiring" the value or physical entity. "Directly acquiring" means performing a process (e.g., performing an analytical method or protocol) to obtain the value or physical entity. "Indirectly acquiring" refers to receiving the value or physical entity from another party or source (e.g., a third-party laboratory that directly acquired the physical entity or value). Directly acquiring a value or physical entity includes performing a process that includes a physical change in a physical substance or the use of a machine or device. Examples of directly acquiring a value include obtaining a sample from a human subject. Directly acquiring a value includes performing a process that uses a machine or device, e.g., using a fluorescence microscope to acquire fluorescence microscopy data.

"Administer", "administering", or "administration", as used herein, refer to implanting, absorbing, ingesting, injecting or otherwise introducing into a subject, an entity described herein (e.g., a device or a preparation of devices), or providing such an entity to a subject for administration.

"Afibrotic", as used herein, means a compound or material that mitigates the foreign body response (FBR). For example, the amount of FBR in a biological tissue that is induced by implant into that tissue of a device (e.g., hydrogel capsule) comprising an afibrotic compound (e.g., a hydrogel capsule comprising a polymer covalently modified with a compound listed in Table 4) is lower than the FBR induced by implantation of an afibrotic-null reference device, i.e., a device that lacks any afibrotic compound, but is of substantially the same composition (e.g., same cell type(s)) and structure (e.g., size, shape, no. of compartments). In an embodiment, the degree of the FBR is assessed by the immunological response in the tissue containing the implanted device (e.g., hydrogel capsule), which may include, for example, protein adsorption, macrophages, multinucleated foreign body giant cells, fibroblasts, and angiogenesis, using assays known in the art, e.g., as described in WO 2017/075630, or using one or more of the assays/methods described Vegas, A., et al., Nature Biotechnol (supra), (e.g., subcutaneous cathepsin measurement of implanted capsules, Masson's trichrome (MT), hematoxylin or eosin staining of tissue sections, quantification of collagen density, cellular staining and confocal microscopy for macrophages (CD68 or F4/80), myofibroblasts (alpha-muscle actin, SMA) or general cellular deposition, quantification of 79 RNA sequences of known inflammation factors and immune cell markers, or FACS analysis for macrophage and neutrophil cells on retrieved devices (e.g., capsules) after 14 days in the intraperitoneal space of a suitable test subject, e.g., an immunocompetent mouse. In an embodiment, the FBR is assessed by measuring the levels in the tissue containing the implant of one or more biomarkers of immune response, e.g., cathepsin, TNF-α, IL-13, IL-6, G-CSF, GM-CSF, IL-4, CCL2, or CCL4. In some embodiments, the FBR induced by a device of the invention (e.g., a hydrogel capsule comprising an afibrotic compound disposed on its outer surface), is at least about 80%, about 85%, about 90%, about 95%, about 99%, or about 100% lower than the FBR induced by an FBR-null reference device, e.g., a device that is substantially identical to the test or claimed device except for lacking the means for mitigating the FBR (e.g., a hydrogel capsule that does not comprise an afibrotic compound but is otherwise substantially identical to the claimed capsule. In some embodiments, the FBR (e.g., level of a biomarker(s)) is measured after about 30 minutes, about 1 hour, about 6 hours, about 12 hours, about 1 day, about 2 days, about 3 days, about 4 days, about 1 week, about 2 weeks, about 1 month, about 2 months, about 3 months, about 6 months, or longer.

"Cell," as used herein, refers to an engineered cell or a cell that is not engineered. In an embodiment, a cell is an immortalized cell or an engineered cell derived from an immortalized cell. In an embodiment, the cell is a live cell, e.g., is viable as measured by any technique described herein or known in the art.

"Conservatively modified variants" or conservative substitution", as used herein, refers to a variant of a reference peptide or polypeptide that is identical to the reference molecule, except for having one or more conservative amino acid substitutions in its amino acid sequence. In an embodiment, a conservatively modified variant consists of an amino acid sequence that is at least 70%, 80%, 85%, 90%, 95%, 97%, 98% or 99% identical to the reference amino acid sequence. A conservative amino acid substitution refers to substitution of an amino acid with an amino acid having similar characteristics (e.g., charge, side-chain size, hydrophobicity/hydrophilicity, backbone conformation and rigidity, etc.) and which has minimal impact on the biological activity of the resulting substituted peptide or polypeptide. Conservative substitution tables of functionally similar amino acids are well known in the art, and exemplary substitutions grouped by functional features are set forth in Table 1 below.

TABLE 1

Exemplary conservative amino acid substitution groups.

| Feature | Conservative Amino Group |
|---|---|
| Charge/Polarity | His, Arg, Lys |
| | Asp, Glu |
| | Cys, Thr, Ser, Gly, Asn, Gln, Tyr |
| | Ala, Pro, Met, Leu, Ile, Val, Phe, Trp |
| Hydrophobicity | Asp, Glu, Asn, Gln, Arg, Lys |
| | Cys, Ser, Thr, Pro, Gly, His, Tyr |
| | Ala, Met, Ile, Leu, Val, Phe, Trp |
| Structural/Surface Exposure | Asp, Glu, Asn, Aln, His, Arg, Lys |
| | Cys, Ser, Tyr, Pro, Ala, Gly, Trp, Tyr |
| | Met, Ile, Leu, Val, Phe |
| Secondary Structure Propensity | Ala, Glu, Aln, His, Lys, Met, Leu, Arg |
| | Cys, Thr, Ile, Val, Phe, Tyr, Trp |
| | Ser, Gly, Pro, Asp, Asn |

TABLE 1-continued

Exemplary conservative amino acid substitution groups.

| Feature | Conservative Amino Group |
|---|---|
| Evolutionary Conservation | Asp, Glu |
| | His, Lys, Arg |
| | Asn, Gln |
| | Ser, Thr |
| | Leu, Ile, Val |
| | Phe, Tyr, Trp |
| | Ala, Gly |
| | Met, Cys |

"Consists essentially of", and variations such as "consist essentially of" or "consisting essentially of" as used throughout the specification and claims, indicate the inclusion of any recited elements or group of elements, and the optional inclusion of other elements, of similar or different nature than the recited elements, that do not materially change the basic or novel properties of the specified molecule, composition, device, or method. As a non-limiting example, an antigen that consists essentially of a recited amino acid sequence may also include one or more amino acids, including substitutions in the recited amino acid sequence, of one or more amino acid residues, which do not materially affect the relevant biological activity (e.g., immunogenicity) of the antigen.

"Derived from", as used herein with respect to cells, refers to cells obtained from tissue, cell lines, or cells, which optionally are then cultured, passaged, differentiated, induced, etc. to produce the derived cells. For example, mesenchymal stem cells can be derived from mesenchymal tissue and then differentiated into a variety of cell types.

"Device", as used herein, refers to any implantable object (e.g., a particle, a hydrogel capsule, an implant, a medical device), which contains a cell or cells (e.g., live cells) capable of expressing and secreting an antigen or antigens following implant of the device, and has a configuration that supports the viability of the cells by allowing cell nutrients to enter the device.

"Differential volume," as used herein, refers to a volume of one compartment within a device described herein that excludes the space occupied by another compartment(s). For example, the differential volume of the second (e.g., outer) compartment in a 2-compartment device with inner and outer compartments, refers to a volume within the second compartment that excludes space occupied by the first (inner) compartment.

An "endogenous nucleic acid" as used herein, is a nucleic acid that occurs naturally in a subject cell.

An "endogenous polypeptide," as used herein, is a polypeptide that occurs naturally in a subject cell.

"Engineered cell," as used herein, is a cell (e.g., an RPE cell) having a non-naturally occurring alteration, and typically comprises a nucleic acid sequence (e.g., DNA or RNA) or a polypeptide not present (or present at a different level than) in an otherwise similar cell under similar conditions that is not engineered (an exogenous nucleic acid sequence). In an embodiment, an engineered cell comprises an exogenous nucleic acid (e.g., a vector or an altered chromosomal sequence). In an embodiment, an engineered cell comprises an exogenous polypeptide. In an embodiment, an engineered cell comprises an exogenous nucleic acid sequence, e.g., a sequence, e.g., DNA or RNA, not present in a similar cell that is not engineered. In an embodiment, the exogenous nucleic acid sequence is chromosomal, e.g., the exogenous nucleic acid sequence is an exogenous sequence disposed in endogenous chromosomal sequence. In an embodiment, the exogenous nucleic acid sequence is chromosomal or extra chromosomal, e.g., a non-integrated vector. In an embodiment, the exogenous nucleic acid sequence comprises an RNA sequence, e.g., an mRNA. In an embodiment, the exogenous nucleic acid sequence comprises a chromosomal or extra-chromosomal exogenous nucleic acid sequence that comprises a sequence which is expressed as RNA, e.g., mRNA or a regulatory RNA. In an embodiment, the exogenous nucleic acid sequence comprises a chromosomal or extra-chromosomal nucleic acid sequence, which comprises a sequence that encodes a polypeptide, or which is expressed as a polypeptide. In an embodiment, the exogenous nucleic acid sequence comprises a first chromosomal or extra-chromosomal exogenous nucleic acid sequence that modulates the conformation or expression of a second nucleic acid sequence, wherein the second amino acid sequence can be exogenous or endogenous. For example, an engineered cell can comprise an exogenous nucleic acid that controls the expression of an endogenous sequence. In an embodiment, an engineered cell comprises a polypeptide present at a level or distribution which differs from the level found in a similar cell that has not been engineered. In an embodiment, an engineered cell comprises an RPE engineered to produce an RNA or a polypeptide. For example, an engineered cell may comprise an exogenous nucleic acid sequence comprising a chromosomal or extra-chromosomal exogenous nucleic acid sequence that comprises a sequence which is expressed as RNA, e.g., mRNA or a regulatory RNA. In an embodiment, an engineered cell (e.g., an RPE cell) comprises an exogenous nucleic acid sequence that comprises a chromosomal or extra-chromosomal nucleic acid sequence comprising a sequence that encodes a polypeptide, or which is expressed as a polypeptide. In an embodiment, the polypeptide is encoded by a codon optimized sequence to achieve higher expression of the polypeptide than a naturally-occurring coding sequence. The codon optimized sequence may be generated using a commercially available algorithm, e.g., GeneOptimizer (ThermoFisher Scientific), OptimumGene™ (GenScript, Piscataway, NJ USA), GeneGPS® (ATUM, Newark, CA USA), or Java Codon Adaptation Tool (JCat, www.jcat.de, Grote, A. et al., Nucleic Acids Research, Vol 33, Issue suppl_2, pp. W526-W531 (2005)). In an embodiment, an engineered cell (e.g., an RPE cell) comprises an exogenous nucleic acid sequence that modulates the conformation or expression of an endogenous sequence. In an embodiment, an engineered cell (e.g., RPE cell) is cultured from a population of stably-transfected cells, or from a monoclonal cell line.

An "exogenous nucleic acid," as used herein, is a nucleic acid that does not occur naturally in a subject cell.

An "exogenous polypeptide," as used herein, is a polypeptide that does not occur naturally in a subject cell, e.g., engineered cell. Reference to an amino acid position of a specific sequence means the position of said amino acid in a reference amino acid sequence, e.g., sequence of a full-length mature (after signal peptide cleavage) wild-type protein (unless otherwise stated), and does not exclude the presence of variations, e.g., deletions, insertions and/or substitutions at other positions in the reference amino acid sequence.

"Polymer composition", as used herein, is a composition (e.g., a solution, mixture) comprising one or more polymers. As a class, "polymers' includes homopolymers, heteropolymers, co-polymers, block polymers, block co-polymers and can be both natural and synthetic. Homopolymers contain one type of building block, or monomer, whereas co-polymers contain more than one type of monomer.

"Polypeptide", as used herein, refers to a polymer comprising amino acid residues linked through peptide bonds and having at least two, and in some embodiments, at least 10, 50, 75, 100, 150 or 200 amino acid residues.

"Prevention," "prevent," and "preventing" as used herein refers to a treatment that comprises administering or applying a therapy, e.g., administering a composition of devices encapsulating cells (e.g., as described herein), prior to the onset of a disease, disorder, or condition to preclude the physical manifestation of said disease, disorder, or condition. In some embodiments, "prevention," "prevent," and "preventing" require that signs or symptoms of the disease, disorder, or condition have not yet developed or have not yet been observed. In some embodiments, treatment comprises prevention and in other embodiments it does not.

"RPE cell" as used herein refers to a cell having one or more of the following characteristics: a) it comprises a retinal pigment epithelial cell (RPE) (e.g., cultured using the ARPE-19 cell line (ATCC® CRL-2302™)) or a cell derived therefrom, e.g., by stably transfecting cells cultured from the ARPE-19 cell line with an exogenous sequence that encodes an antigen or otherwise engineering such cultured ARPE-19 cells to express an exogenous protein or other exogenous substance, a cell derived from a primary cell culture of RPE cells, a cell isolated directly (without long term culturing, e.g., less than 5 or 10 passages or rounds of cell division since isolation) from naturally occurring RPE cells, e.g., from a human or other mammal, a cell derived from a transformed, an immortalized, or a long term (e.g., more than 5 or 10 passages or rounds of cell division) RPE cell culture; b) a cell that has been obtained from a less differentiated cell, e.g., a cell developed, programmed, or reprogramed (e.g., in vitro) into an RPE cell or a cell that is, except for any genetic engineering, substantially similar to one or more of a naturally occurring RPE cell or a cell from a primary or long term culture of RPE cells (e.g., the cell can be derived from an IPS cell); or c) a cell that has one or more of the following properties: i) it expresses one or more of the biomarkers CRALBP, RPE-65, RLBP, BESTI, or αβ-crystallin; ii) it does not express one or more of the biomarkers CRALBP, RPE-65, RLBP, BESTI, or αβ-crystallin; iii) it is naturally found in the retina and forms a monolayer above the choroidal blood vessels in the Bruch's membrane; iv) it is responsible for epithelial transport, light absorption, secretion, and immune modulation in the retina; or v) it has been created synthetically, or modified from a naturally occurring cell, to have the same or substantially the same genetic content, and optionally the same or substantially the same epigenetic content, as an immortalized RPE cell line (e.g., the ARPE-19 cell line (ATCC® CRL-2302™)). In an embodiment, an RPE cell described herein is engineered, e.g., to have a new property, e.g., the cell is engineered to express and secrete one or more antigens or an immunomodulatory agent. In other embodiments, an RPE cell is not engineered.

"Sequence identity" or "percent identical", when used herein to refer to two nucleotide sequences or two amino acid sequences, means the two sequences are the same within a specified region, or have the same nucleotides or amino acids at a specified percentage of nucleotide or amino acid positions within the specified when the two sequences are compared and aligned for maximum correspondence over a comparison window or designated region. Sequence identity may be determined using standard techniques known in the art including, but not limited to, any of the algorithms described in US Patent Application Publication No. 2017/02334455. In an embodiment, the specified percentage of identical nucleotide or amino acid positions is at least about 80%, 85%, 90%, 91%, 92%, 93%, 94%, 95%, 96%, 97%, 98%, 99% or higher.

"Spherical" as used herein, means a device (e.g., a hydrogel capsule or other particle) having a curved surface that forms a sphere (e.g., a completely round ball) or sphere-like shape, which may have waves and undulations, e.g., on the surface. Spheres and sphere-like objects can be mathematically defined by rotation of circles, ellipses, or a combination around each of the three perpendicular axes, a, b, and c. For a sphere, the three axes are the same length. Generally, a sphere-like shape is an ellipsoid (for its averaged surface) with semi-principal axes within 10%, or 5%, or 2.5% of each other. The diameter of a sphere or sphere-like shape is the average diameter, such as the average of the semi-principal axes.

"Spheroid", as that term is used herein to refer to a device (e.g., a hydrogel capsule or other particle), means the device has (i) a perfect or classical oblate spheroid or prolate spheroid shape or (ii) has a surface that roughly forms a spheroid, e.g., may have waves and undulations and/or may be an ellipsoid (for its averaged surface) with semi-principal axes within 100% of each other.

"Subject" as used herein refers to a human or non-human animal. In an embodiment, the subject is a human (i.e., a male or female), e.g., of any age group, a pediatric subject (e.g., infant, child, adolescent) or adult subject (e.g., young adult, middle-aged adult, or senior adult). In an embodiment, the subject is a non-human animal, for example, a mammal (e.g., a mouse, a dog, a primate (e.g., a cynomolgus monkey or a rhesus monkey)). In an embodiment, the subject is a commercially relevant mammal (e.g., a cattle, pig, horse, sheep, goat, cat, or dog) or a bird (e.g., a commercially relevant bird such as a chicken, duck, goose, or turkey). In certain embodiments, the animal is a mammal. The animal may be a male or female and at any stage of development. A non-human animal may be a transgenic animal.

"Treatment," "treat," and "treating" as used herein refers to one or more of reducing, reversing, alleviating, delaying the onset of, or inhibiting the progress of one or more of a symptom, manifestation, or underlying cause, of a disease, disorder, or condition. In an embodiment, treating comprises reducing, reversing, alleviating, delaying the onset of, or inhibiting the progress of a symptom of a disease, disorder, or condition. In an embodiment, treating comprises reducing, reversing, alleviating, delaying the onset of, or inhibiting the progress of a manifestation of a disease, disorder, or condition. In an embodiment, treating comprises reducing, reversing, alleviating, reducing, or delaying the onset of, an underlying cause of a disease, disorder, or condition. In some embodiments, "treatment," "treat," and "treating" require that signs or symptoms of the disease, disorder, or condition have developed or have been observed. In other embodiments, treatment may be administered in the absence of signs or symptoms of the disease or condition, e.g., in preventive treatment. For example, treatment (e.g., a vaccine composition) may be administered to a susceptible individual prior to the onset of symptoms (e.g., considering a history of symptoms and/or in light of genetic or other susceptibility factors). Treatment may also be continued after symptoms have resolved, for example, to delay or prevent recurrence. In some embodiments, treatment comprises prevention and in other embodiments it does not.

Selected Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

The abbreviations used herein have their conventional meaning within the chemical and biological arts. The chemical structures and formulae set forth herein are constructed according to the standard rules of chemical valency known in the chemical arts.

When a range of values is listed, it is intended to encompass each value and sub-range within the range. For example, "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

As used herein, "alkyl" refers to a radical of a straight-chain or branched saturated hydrocarbon group having from 1 to 24 carbon atoms ("$C_1$-$C_{24}$ alkyl"). In some embodiments, an alkyl group has 1 to 12 carbon atoms ("$C_1$-$C_{12}$ alkyl"), 1 to 10 carbon atoms ("$C_1$-$C_{12}$ alkyl"), 1 to 8 carbon atoms ("$C_1$-$C_8$ alkyl"), 1 to 6 carbon atoms ("$C_1$-$C_6$ alkyl"), 1 to 5 carbon atoms ("$C_1$-$C_5$ alkyl"), 1 to 4 carbon atoms ("$C_1$-$C_4$alkyl"), 1 to 3 carbon atoms ("$C_1$-$C_3$ alkyl"), 1 to 2 carbon atoms ("$C_1$-$C_2$ alkyl"), or 1 carbon atom ("$C_1$ alkyl"). In some embodiments, an alkyl group has 2 to 6 carbon atoms ("$C_2$-$C_6$alkyl"). Examples of $C_1$-$C_6$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Each instance of an alkyl group may be independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent.

As used herein, "alkenyl" refers to a radical of a straight-chain or branched hydrocarbon group having from 2 to 24 carbon atoms, one or more carbon-carbon double bonds, and no triple bonds ("$C_2$-$C_{24}$ alkenyl"). In some embodiments, an alkenyl group has 2 to 10 carbon atoms ("$C_2$-$C_{10}$ alkenyl"), 2 to 8 carbon atoms ("$C_2$-$C_8$ alkenyl"), 2 to 6 carbon atoms ("$C_2$-$C_6$ alkenyl"), 2 to 5 carbon atoms ("$C_2$-$C_5$ alkenyl"), 2 to 4 carbon atoms ("$C_2$-$C_4$ alkenyl"), 2 to 3 carbon atoms ("$C_2$-$C_3$ alkenyl"), or 2 carbon atoms ("$C_2$ alkenyl"). The one or more carbon-carbon double bonds can be internal (such as in 2-butenyl) or terminal (such as in 1-butenyl). Examples of $C_2$-$C_4$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-$C_6$ alkenyl groups include the aforementioned $C_{2-4}$ alkenyl groups as well as pentenyl ($C_5$), pentadienyl ($C_5$), hexenyl ($C_6$), and the like. Each instance of an alkenyl group may be independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent.

As used herein, the term "alkynyl" refers to a radical of a straight-chain or branched hydrocarbon group having from 2 to 24 carbon atoms, one or more carbon-carbon triple bonds ("$C_2$-$C_{24}$ alkenyl"). In some embodiments, an alkynyl group has 2 to 10 carbon atoms ("$C_2$-$C_{10}$ alkynyl"), 2 to 8 carbon atoms ("$C_2$-$C_8$ alkynyl"), 2 to 6 carbon atoms ("$C_2$-$C_6$ alkynyl"), 2 to 5 carbon atoms ("$C_2$-$C_5$ alkynyl"), 2 to 4 carbon atoms ("$C_2$-$C_4$ alkynyl"), 2 to 3 carbon atoms ("$C_2$-$C_3$ alkynyl"), or 2 carbon atoms ("$C_2$ alkynyl"). The one or more carbon-carbon triple bonds can be internal (such as in 2-butynyl) or terminal (such as in 1-butynyl). Examples of $C_2$-$C_4$ alkynyl groups include ethynyl ($C_2$), 1-propynyl ($C_3$), 2-propynyl ($C_3$), 1-butynyl ($C_4$), 2-butynyl ($C_4$), and the like. Each instance of an alkynyl group may be independently optionally substituted, i.e., unsubstituted (an "unsubstituted alkynyl") or substituted (a "substituted alkynyl") with one or more substituents e.g., for instance from 1 to 5 substituents, 1 to 3 substituents, or 1 substituent.

As used herein, the term "heteroalkyl," refers to a non-cyclic stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any position of the heteroalkyl group. Exemplary heteroalkyl groups include, but are not limited to: $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2$, $-S(O)-CH_3$, $-CH_2-CH_2-S(O)_2-CH_3$, $-CH=CH-O-CH_3$, $-Si(CH_3)_3$, $-CH_2-CH=N-OCH_3$, $-CH=CH-N(CH_3)-CH_3$, $-O-CH_3$, and $-O-CH_2-CH_3$. Up to two or three heteroatoms may be consecutive, such as, for example, $-CH_2-NH-OCH_3$ and $-CH_2-O-Si(CH_3)_3$. Where "heteroalkyl" is recited, followed by recitations of specific heteroalkyl groups, such as $-CH_2O$, $-NR^CR^D$, or the like, it will be understood that the terms heteroalkyl and $-CH_2O$ or $-NR^CR^D$ are not redundant or mutually exclusive. Rather, the specific heteroalkyl groups are recited to add clarity. Thus, the term "heteroalkyl" should not be interpreted herein as excluding specific heteroalkyl groups, such as $-CH_2O$, $-NR^CR^D$, or the like. Each instance of a heteroalkyl group may be independently optionally substituted, i.e., unsubstituted (an "unsubstituted heteroalkyl") or substituted (a "substituted heteroalkyl") with one or more substituents e.g., for instance from 1 to 5 substituents, 1 to 3 substituents, or 1 substituent.

The terms "alkylene," "alkenylene," "alkynylene," or "heteroalkylene," alone or as part of another substituent, mean, unless otherwise stated, a divalent radical derived from an alkyl, alkenyl, alkynyl, or heteroalkyl, respectively. An alkylene, alkenylene, alkynylene, or heteroalkylene group may be described as, e.g., a $C_1$-$C_6$-membered alkylene, $C_2$-$C_6$-membered alkenylene, $C_2$-$C_6$-membered alkynylene, or $C_1$-$C_6$-membered heteroalkylene, wherein the term "membered" refers to the non-hydrogen atoms within the moiety. In the case of heteroalkylene groups, heteroatoms can also occupy either or both chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $-C(O)_2R'-$ may represent both $-C(O)_2R'-$ and $-R'C(O)_2-$.

As used herein, "aryl" refers to a radical of a monocyclic or polycyclic (e.g., bicyclic or tricyclic) 4n+2 aromatic ring system (e.g., having 6, 10, or 14 $\pi$ electrons shared in a cyclic array) having 6-14 ring carbon atoms and zero heteroatoms provided in the aromatic ring system ("$C_6$-$C_{14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). An aryl group may be described as, e.g., a $C_6$-$C_{10}$-membered aryl, wherein the term "membered" refers to the non-hydrogen ring atoms within the moiety. Aryl groups include phenyl, naphthyl, indenyl, and tetrahydronaphthyl. Each instance of an aryl group may be independently optionally substituted, i.e., unsubstituted (an "unsubstituted aryl") or substituted (a "substituted aryl") with one or more substituents.

As used herein, "heteroaryl" refers to a radical of a 5-10 membered monocyclic or bicyclic 4n+2 aromatic ring system (e.g., having 6 or 10 $\pi$ electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group may be described as, e.g., a 6-10-membered heteroaryl, wherein the term "membered" refers to the non-hydrogen ring atoms within the moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Each instance of a heteroaryl group may be independently optionally substituted, i.e., unsubstituted (an "unsubstituted heteroaryl") or substituted (a "substituted heteroaryl") with one or more substituents.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Other exemplary heteroaryl groups include heme and heme derivatives.

As used herein, the terms "arylene" and "heteroarylene," alone or as part of another substituent, mean a divalent radical derived from an aryl and heteroaryl, respectively.

As used herein, "cycloalkyl" refers to a radical of a non-aromatic cyclic hydrocarbon group having from 3 to 10 ring carbon atoms ("$C_3$-$C_{10}$ cycloalkyl") and zero heteroatoms in the non-aromatic ring system. In some embodiments, a cycloalkyl group has 3 to 8 ring carbon atoms ("$C_3$-$C_8$cycloalkyl"), 3 to 6 ring carbon atoms ("$C_3$-$C_6$ cycloalkyl"), or 5 to 10 ring carbon atoms ("$C_5$-$C_{10}$ cycloalkyl"). A cycloalkyl group may be described as, e.g., a $C_4$-$C_7$-membered cycloalkyl, wherein the term "membered" refers to the non-hydrogen ring atoms within the moiety. Exemplary $C_3$-$C_6$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_3$-$C_8$ cycloalkyl groups include, without limitation, the aforementioned $C_3$-$C_6$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), cubanyl ($C_8$), bicyclo[1.1.1]pentanyl ($C_5$), bicyclo[2.2.2]octanyl ($C_8$), bicyclo[2.1.1]hexanyl ($C_6$), bicyclo[3.1.1]heptanyl ($C_7$), and the like. Exemplary $C_3$-$C_{10}$ cycloalkyl groups include, without limitation, the aforementioned $C_3$-$C_8$ cycloalkyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the cycloalkyl group is either monocyclic ("monocyclic cycloalkyl") or contain a fused, bridged or spiro ring system such as a bicyclic system ("bicyclic cycloalkyl") and can be saturated or can be partially unsaturated. "Cycloalkyl" also includes ring systems wherein the cycloalkyl ring, as defined above, is fused with one or more aryl groups wherein the point of attachment is on the cycloalkyl ring, and in such instances, the number of carbons continue to designate the number of carbons in the cycloalkyl ring system. Each instance of a cycloalkyl group may be independently optionally substituted, i.e., unsubstituted (an "unsubstituted cycloalkyl") or substituted (a "substituted cycloalkyl") with one or more substituents.

"Heterocyclyl" as used herein refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more cycloalkyl groups wherein the point of attachment is either on the cycloalkyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. A heterocyclyl group may be described as, e.g., a 3-7-membered heterocyclyl, wherein the term "membered" refers to the non-hydrogen ring atoms, i.e., carbon, nitrogen, oxygen, sulfur, boron, phosphorus, and silicon, within the moiety. Each instance of heterocyclyl may be independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, piperazinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl or thiomorpholinyl-1,1-dioxide. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Amino" as used herein refers to the radical —$NR^{70}R^{71}$, wherein $R^{70}$ and $R^{71}$ are each independently hydrogen, $C_1$-$C_8$ alkyl, $C_3$-$C_{10}$ cycloalkyl, $C_4$-$C_{10}$ heterocyclyl, $C_6$-$C_{10}$ aryl, and $C_5$-$C_{10}$ heteroaryl. In some embodiments, amino refers to $NH_2$.

As used herein, "cyano" refers to the radical-CN.

As used herein, "halo" or "halogen," independently or as part of another substituent, mean, unless otherwise stated, a fluorine (F), chlorine (CL), bromine (Br), or iodine (I) atom.

As used herein, "hydroxy" refers to the radical-OH.

Alkyl, alkenyl, alkynyl, heteroalkyl, cycloalkyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" cycloalkyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, such as any of the substituents described herein that result in the formation of a stable compound. The present disclosure contemplates any and all such combinations to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Two or more substituents may optionally be joined to form aryl, heteroaryl, cycloalkyl, or heterocyclyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Compounds of Formula (I) described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high-pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, IN 1972). The disclosure additionally encompasses compounds described herein as individual isomers substantially free of other isomers, and alternatively, as mixtures of various isomers.

As used herein, a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 99% by weight, more than 99.5% by weight, or more than 99.9% by weight, of the enantiomer. In certain embodiments, the weights are based upon total weight of all enantiomers or stereoisomers of the compound.

Compounds of Formula (I) described herein may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like.

The term "pharmaceutically acceptable salt" is meant to include salts of the active compounds that are prepared with relatively nontoxic acids or bases, depending on the particular substituents found on the compounds described herein.

When compounds of Formula (I) used to prepare devices of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds used in the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, e.g., Berge et al, *Journal of Pharmaceutical Science* 66:1-19 (1977)). Certain specific compounds used in the devices of the present disclosure (e.g., a particle, a hydrogel capsule) contain both basic and acidic functionalities that allow the compounds to be converted into either base or acid addition salts. These salts may be prepared by methods known to those skilled in the art. Other pharmaceutically acceptable carriers known to those of skill in the art are suitable for use in the present disclosure.

Devices of the present disclosure may contain a compound of Formula (I) in a prodrug form. Prodrugs are those compounds that readily undergo chemical changes under physiological conditions to provide the compounds useful for preparing devices in the present disclosure. Additionally, prodrugs can be converted to useful compounds of Formula (I) by chemical or biochemical methods in an ex vivo environment.

Certain compounds of Formula (I) described herein can exist in unsolvated forms as well as solvated forms, including hydrated forms. In general, the solvated forms are equivalent to unsolvated forms and are encompassed within the scope of the present disclosure. Certain compounds of Formula (I) described herein may exist in multiple crystalline or amorphous forms. In general, all physical forms are equivalent for the uses contemplated by the present disclosure and are intended to be within the scope of the present disclosure.

The term "solvate" refers to forms of the compound that are associated with a solvent, usually by a solvolysis reaction. This physical association may include hydrogen bonding. Conventional solvents include water, methanol, ethanol, acetic acid, DMSO, THE, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound and wherein x is a number greater than 0.

The term "tautomer" as used herein refers to compounds that are interchangeable forms of a compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Tautomeric forms may be relevant to the attainment of the optimal chemical reactivity and biological activity of a compound of interest.

The symbol "∿∿" as used herein refers to a connection to an entity, e.g., a polymer (e.g., hydrogel-forming polymer such as alginate) or surface of an implantable device, e.g., a particle, a hydrogel capsule. The connection represented by "∿∿" may refer to direct attachment to the entity, e.g., a polymer or an implantable element, may refer to linkage to the entity through an attachment group. An "attachment group," as described herein, refers to a moiety for linkage of a compound of Formula (I) to an entity (e.g., a polymer or an implantable element (e.g., a device) as described herein), and may comprise any attachment chemistry known in the art. A listing of exemplary attachment groups is outlined in *Bioconjugate Techniques* ($3^{rd}$ ed, Greg T. Hermanson, Waltham, MA: Elsevier, Inc, 2013), which is incorporated herein by reference in its entirety. In some embodiments, an attachment group comprises alkyl, alkenyl, alkynyl, heteroalkyl, cycloalkyl, heterocyclyl, aryl, heteroaryl, —C(O)—, —OC(O)—, $—N(R^C)—$, $—N(R^C)C(O)$, $—C(O)N(R^C)—$, $—N(R^C)N(R^D)$, —NCN—, $—C(=N(R^C)(R^D))O—$, —S—, —S(O)—, $—OS(O)_x—$, $—N(R^C)S(O)_x—$, $—S(O)_xN(R^C)—$, $—P(R^F)_y—$, $—Si(OR^A)_2—$, $—Si(R^G)(OR^A)—$, $—B(OR^A)—$, or a metal, wherein each of $R^A$, $R^C$, $R^D$, $R^F$, $R^G$, x and y is independently as described herein. In some embodiments, an attachment group comprises an amine, ketone, ester, amide, alkyl, alkenyl, alkynyl, or thiol. In some embodiments, an attachment group is a cross-linker. In some embodiments, the attachment group is $—C(O)(C_1\text{-}C_6\text{-alkylene})\text{-}$, wherein alkylene is substituted with $R^1$, and $R^1$ is as described herein. In some embodiments, the attachment group is $—C(O)(C_1\text{-}C_6\text{-alkylene})\text{-}$, wherein alkylene is substituted with 1-2 alkyl groups (e.g., 1-2 methyl groups). In some embodiments, the attachment group is $—C(O)C(CH_3)_2—$. In some embodiments, the attachment group is —C(O)(methylene)-, wherein alkylene is substituted with 1-2 alkyl groups (e.g., 1-2 methyl groups). In some embodiments, the attachment group is $—C(O)CH(CH_3)—$. In some embodiments, the attachment group is $—C(O)C(CH_3)—$.

Infectious Agents and Antigens

Devices of the present disclosure may be configured to induce a protective immune response against a variety of infectious agents. Such agents include viruses, bacteria, fungi and parasites.

Non-limiting examples of infectious agents that could be immunized against include adenoviruses (e.g., serotypes 4 and 7), BK virus, coronaviruses (e.g., Middle East respiratory syndrome-related coronavirus (MERS-COV), severe acute respiratory syndrome coronavirus (SARS-COV), severe acute respiratory syndrome coronavirus 2 (SARS-COV-2)), cytomegalovirus, Dengue virus (e.g., serotypes 1-4), Epstein-Barr virus (EBV), human herpes virus 6 (HHV-6), human immunodeficiency viruses (e.g., HIV-1 and HIV-2), Japanese encephalitis virus, Yellow fever virus, West Nile virus, varicella zoster virus (VZV), tick-borne encephalitis virus, rubella virus, rotaviruses, rabies virus, poliovirus types 1 and 3, measles virus, mumps virus, rubella, pneumococcus, polio virus, rotavirus, herpes simplex viruses (HSV-1 and HSV-2), hepatitis A virus, hepatitis B virus, hepatitis C virus, hepatitis E virus (e.g., genotypes 1, 2, 3 and 4), human parainfluenza viruses (HPIV), influenza viruses of type A (e.g., subtype H1N1) and type B, human papillomavirus (HPV), respiratory syncytial virus (RSV), *Vibrio cholerae* bacteria of serogroups 01 and 0139, the bacterial species that cause Lyme disease (e.g, *Borrelia burgdorferi* and *Borrelia* mayonii), the typhoid *bacillus* S. *Typhi*, the tubercle *bacillus Mycobacterium tuberculosis*, multiple serotypes of the bacterium *Streptococcus pneumoniae, Neisseria meningitidis* bacteria (e.g., serogroups A, B, C, W, X and Y), the bacterium *Haemophilus influenzae* type b (Hib), the bacterium *Bordetella pertussis*, the bacterium *Clostridium tetani*, toxigenic ('orynebacterium *diphtheriae*, Methicillin-resistant *Staphylococcus aureus, Plasmodium* protozoan parasite (e.g., *P. falciparum, P. vivax, P. ovale, P. malariae* and *P. knowlesi*), *Schistosoma* trematodes (eg., *Schistosoma* haematobin and *S. mansoni*), soil-transmitted helminths (roundworms (e.g., *Ascaris* hunbricoides); whipworms (e.g., *Trichuris trichiura*) and hookworms (*Necator americanus* and *Ancylostoma duodenale*)), cestoid parasites (e.g., *Echinococcus* species), ectoparasites (e.g, lice), and parasitic mites (e.g, *Sarcoptes scabiei*).

A number of commercially available vaccines are combination vaccines, e.g., they include antigens against multiple infectious agents, e.g, quadrivalent flu vaccine (two influenza A viruses and two influenza B viruses), DTap (diphtheria-tetanus-pertussis), trivalent IPV (three strains of inactivated polio vaccine), MMR (measles-mumps-rubella), MMRV (measles, mumps, rubella and chickenpox), HepA-HepB.

An implantable device of the present disclosure may readily be configured to act as a "combination vaccine" · cells that express one or more antigens of each of the desired combination of two or more infectious agents are placed in the device. In an embodiment, a mixture of cells engineered to express and secrete antigen(s) of a first infectious agent are mixed with cells engineered to express and secrete antigen(s) of a second infectious agent would be placed into the device, e.g., by encapsulation, e.g., in a hydrogel capsule. In another embodiment, a combination vaccine composition may comprise a mixture of hydrogel capsules encapsulating cells that express and secrete antigen(s) for a first infectious agent and hydrogel capsule encapsulating cells that express and secrete antigen(s) for a second infectious agent. In yet another embodiment, cells engineered to express and secrete antigen(s) of a first infectious agent are placed in one cell-containing compartment, and cells engineered to express and secrete antigen(s) of a second infectious agent are placed in a second cell-containing compartment.

Patients undergoing certain medical procedures are frequently given multiple individual vaccines against multiple infectious agents. For example, patients undergoing a hematopoietic stem cell transplantation (HSCT) are at risk for infection by a number of common viruses, including HSV, VZV, CMV, EBV, adenoviruses, HHV6, BK virus and upper respiratory viruses such as influenza, parainfluenza, and RSV. The risks to HSCT patients could be reduced by implanting a device or vaccine composition described herein that is configured to deliver antigens for a combination of two, three, four or more of these viruses.

The antigen or antigen cocktail for continuous delivery by a device of the present disclosure may consist essentially of the same amino acid sequence (or a conservatively substituted variant) of the naturally-occurring antigen(s) or of the antigen(s) in any commercially available or investigational vaccine for the targeted infectious agent. In an embodiment, an antigen selected for delivery by a device may be an immunogenic fragment of a known antigen. In some embodiments, the antigen(s) specific for an infectious agent may be selected or designed using a computational vaccinology approach which employs computational tools to map epitopes, select antigens and design immunogens. For example, one commercially available integrated set of immunoinformatic tools is called iVAX, which is a web-based tool available from Epi Vax, Providence, Rhode Island.

In an embodiment, the infectious agent is SARS-COV-2 and cells contained in the device are engineered to express and secrete one or more of the antigens shown in FIGS. 1A-1G, or an immunogenic fragment of one or more of these antigens. Selection of these antigens is supported by the computational data described in Ong, E. et al., "COVID-19 coronavirus vaccine design using reverse vaccinology and machine learning," bioRxiv. In some embodiments, the antigen comprises the SARS-COV-2 surface glycoprotein. In some embodiments, the antigen has about 80%, 85%, 90%, 91%, 92%, 93%, 94%, 95%, 96%, 97%, 98%, 99% sequence identity to SEQ ID NO: 2. In some embodiments, the antigen comprises SEQ ID NO: 2.

In another embodiment, the infectious agent is HIV-1 and cells contained in the device are engineered to express and secrete one or more of the antigens shown in FIGS. 2A-2M, or an immunogenic fragment of one or more of these antigens. Selection of these antigens is supported in part by data described in the following references: Kulp, D. et al., Structure-based design of native-like HIV-1 envelope trimers to silence non-neutralizing epitopes and eliminate CD4 binding. Nature Communications, Vol. 8, Issue 1; Cirelli, K. M., et al., (2019). Slow Delivery Immunization Enhances HIV Neutralizing Antibody and Germinal Center Responses via Modulation of Immunodominance. Cell, 177 (5), 1153-1171.e28.; and Pauthner, M., et al., (2017) Elicitation of Robust Tier 2 Neutralizing Antibody Responses in Nonhuman Primates by HIV Envelope Trimer Immunization Using Optimized Approaches. Immunity, 46 (6), 1073-1088.e6. In some embodiments, the antigen comprises BG505 Olio6.CD4KO. In some embodiments, the antigen has about 80%, 85%, 90%, 91%, 92%, 93%, 94%, 95%, 96%, 97%, 98%, 99% sequence identity to SEQ ID NO: 21. In some embodiments, the antigen comprises SEQ ID NO: 21.

In yet another embodiment, the infectious agent is EBV and cells contained in the device are engineered to express and secrete one or more of the antigens shown in FIGS. 3A-3C, or an immunogenic fragment of one or more of these antigens. Selection of these antigens is supported by the data described in Boyle, M., A vaccine to kiss EBV goodbye, Science Translational Medicine, Vol. 11, Issue 489, eaax 1729.

In a still further embodiment, the infectious agent is RSV and cells contained in the device are engineered to express and secrete one or more of the antigens shown in FIGS. 4A-4C, or an immunogenic fragment of one or more of these antigens. In some embodiments, the antigen comprises the fusion glycoprotein F0. In some embodiments, the antigen has about 80%, 85%, 90%, 91%, 92%, 93%, 94%, 95%, 96%, 97%, 98%, 99% sequence identity to SEQ ID NO: 27. In some embodiments, the antigen comprises SEQ ID NO: 27. Selection of these antigens is supported by the data described in Crank, M. et al., A proof of concept for structure-based vaccine design targeting RSV in humans. Science, Vol. 365, Issue 6452, pp. 505-509 (2019).

Cells

The cell(s) contained in devices of the present disclosure may be a variety of different cell types (e.g., human cells), including epithelial cells, endothelial cells, fibroblast cells, mesenchymal stem cells, and keratinocyte cells. Exemplary cell types include the cell types recited in WO 2017/075631. In some embodiments, the cells are derived from a cell-line shown in Table 2 below.

TABLE 2

Exemplary cell lines

| Cell Line | Cell Type | Germ Layer | Commercial Source |
|---|---|---|---|
| ARPE-19 | Epithelial (Retinal) | Ectoderm | ATCC (CRL-2302) |
| BJ | Fibroblast (Foreskin) | Ectoderm | ATCC (CRL-2522) |
| CCD-841-CoN | Epithelial (Colon) | Endoderm | ATCC (CRL-1790) |
| HaCat | Keratinocyte | Ectoderm | Addexbio (T0020001) |
| HHSEC | Endothelial (Hepatic Sinusoidal) | Endoderm | Sciencellonline.com (#5000) |
| Huv-EC-C | Endothelial (Embryonic umbilical) | Mesoderm | ATCC (CRL-1730) |
| MCF-10A | Epithelial (Mammary Gland) | Ectoderm | ATCC (CRL-10317) |
| MRC-5 | Fibroblast (Lung) | Mesoderm | ATCC (CCL-171) |
| MSC, human | Mesenchyme (Bone Marrow) | Mesoderm | ATCC (PCS-500-012) |
| MSC, mouse | Mesenchyme (Bone Marrow) | Mesoderm | Cyagen (MU BMX-01001) |
| WS-1 | Fibroblast (Skin) | Ectoderm | ATCC (CRL-1502) |
| 293F | Epithelial (Embryonic Kidney) | Mesoderm | Thermo Fisher (R790007) |

Cells may be engineered to express and secrete antigens and immunomodulatory agents using any of a variety of genetic engineering techniques are known in the art. For example, a cell may be transfected with an expression vector comprising nucleotide sequence(s) encoding the desired antigen(s) operably linked to control elements necessary or useful for gene expression, promoters, ribosomal binding sites, enhancers, polyA signal. For antigen(s) that are not naturally secreted by the infectious agent, a nucleotide sequence encoding a secretory signal peptide from a naturally-occurring secreted protein is operably linked to the antigen-encoding nucleotide sequence. In an embodiment, the signal peptide consists essentially of an amino acid sequence shown in Table 3 below. In an embodiment, the signal peptide is MGWRAAGALLLALLLHGRLLA (SEQ ID NO:1).

TABLE 3

Exemplary secretory signal peptide sequences

| Protein | Amino Acid Sequence |
|---|---|
| Albumin | MKWVTFISLLFLFSSAYS |
| Kappa Leader | MVLQTQVFISLLLWISGAYG |
| Plasminogen activator inhibitor 1 | MQMSPALTCLVLGLALVFGEGSA |
| Thrombospondin-1 | MGLAWGLGVLFLMHVCGT |

TABLE 3-continued

Exemplary secretory signal peptide sequences

| Protein | Amino Acid Sequence |
|---|---|
| Fibronectin | MLRGPGPGLLLLAVQCLGTAVPSTGASKSKR |
| Basement membrane-specific heparan sulfate proteoglycan core protein (HSPG2) | MGWRAAGALLLALLLHGRLLA |
| Agrin | MAGRSHPGPLRPLLPLLVVAACVLPGAGG |
| H7 Leader | MEFGLSWVFLVALFRGVQC |
| L2 Leader | MKYLLPTAAAGLLLLAAQPAMA |
| HMM34 | MRPTWAWWLFLVLLLALWAPARG |
| HMM38 | MWWRLWWLLLLLLLLWPMVWA |
| Gaussia luciferase | MGVKVLFALICIAVAEA |
| Alpha-1-antitrypsin | MPSSVSWGILLLAGLCCLVPVSLA |
| Interleukin-10 | MHSSALLCCLVLLTGVRA |

When engineering cells to co-express two or more exogenous antigens and/or immunomodulatory agents, a multicistronic vector may be employed.

In some embodiments, the cells are engineered with a regulatable expression system, to allow controlled expression of the antigen(s) and/or any immunomodulatory agent. A variety of such systems are known in the art and include, for example: kill switches (see, e.g., Wu, C. et al., *Mol. Ther. Methods Clin Dev.* 2014; 1:14053); On/Off systems (see, e.g., Gossen, M and Gujar, H., *Proc. Natl. Acad. Sci. USA*, Vol 89, pp. 5547-5551 (1992); Liberles, S., et al., *Proc. Natl. Acad. Sci. USA, Vol.* 94, pp. 7825-7830 (1997); feed forward and negative feedback systems (Lillacci, G. et al., *Nuc. Acids Res*, Vol 46, Issue 18 (12 Oct. 2018) pp. 9855-9863); temperature inducible systems (Miller, I. et al., *ACS Synth Biol.* 2018; 7 (4): 1167-1173).

Features of Devices

A device of the present disclosure comprises at least one barrier that prevents immune cells from contacting cells contained inside the device. At least a portion of the barrier needs to be sufficiently porous to allow proteins (e.g., antigens) expressed and secreted by the cells to exit the device. A variety of device configurations known in the art are suitable.

The device (e.g., particle) can have any configuration and shape appropriate for supporting the viability and productivity of the contained cells after implant into the intended target location. As non-limiting examples, device shapes may be cylinders, rectangles, disks, ovoids, stellates, or spherical. The device can be comprised of a mesh-like or nested structure. In some embodiments, a device is capable of preventing materials over a certain size from passing through a pore or opening. In some embodiments, a device (e.g., particle) is capable of preventing materials greater than 50 kD, 75 kD, 100 kD, 125 kD, 150 kD, 175 kD, 200 kD, 250 kD, 300 kD, 400 kD, 500 kD, 750 kD, or 1,000 kD from passing through.

In an embodiment, the device is a macroencapsulation device. Nonlimiting examples of macroencapsulation devices (also referred to herein as a macrodevice) are described in: WO 2019/068059, WO 2019/169089, U.S. Pat. Nos. 9,526,880, 9,724,430 and 8,278,106; European Patent No. EP742818B1, and Sang, S. and Roy, S., *Biotechnol. Bioeng.* 113 (7): 1381-1402 (2016).

In an embodiment, the device is a macrodevice having one or more cell-containing compartments. A device with two or more cell-containing compartments may be configured to provide vaccination against two or more infectious agents using a single implant: cells expressing an antigen or antigen cocktail of each targeted infectious agent would be placed in separate compartments. WO 2018/232027 describes a device with multiple cell-containing compartments formed in a micro-fabricated body and covered by a porous membrane.

In an embodiment, the device is configured as a thin, flexible strand as described in U.S. Pat. No. 10,493,107. This strand comprises a substrate, an inner polymeric coating surrounding the substrate and an outer hydrogel coating surrounding the inner polymeric coating. The antigen-expressing cells and any other protein-expressing cells are positioned in the outer coating.

In some embodiments, a device (e.g., particle) has a largest linear dimension (LLD), e.g., mean diameter, or size that is at least about 0.5 millimeter (mm), preferably about 1.0 mm, about 1.5 mm or greater. In some embodiments, a device can be as large as 10 mm in diameter or size. For example, a device or particle described herein is in a size range of 0.5 mm to 10 mm, 1 mm to 10 mm, 1 mm to 8 mm, 1 mm to 6 mm, 1 mm to 5 mm, 1 mm to 4 mm, 1 mm to 3 mm, 1 mm to 2 mm, 1 mm to 1.5 mm, 1.5 mm to 8 mm, 1.5 mm to 6 mm, 1.5 mm to 5 mm, 1.5 mm to 4 mm, 1.5 mm to 3 mm, 1.5 mm to 2 mm, 2 mm to 8 mm, 2 mm to 7 mm, 2 mm to 6 mm, 2 mm to 5 mm, 2 mm to 4 mm, 2 mm to 3 mm, 2.5 mm to 8 mm, 2.5 mm to 7 mm, 2.5 mm to 6 mm, 2.5 mm to 5 mm, 2.5 mm to 4 mm, 2.5 mm to 3 mm, 3 mm to 8 mm, 3 mm to 7 mm, 3 mm to 6 mm, 3 mm to 5 mm, 3 mm to 4 mm, 3.5 mm to 8 mm, 3.5 mm to 7 mm, 3.5 mm to 6 mm, 3.5 mm to 5 mm, 3.5 mm to 4 mm, 4 mm to 8 mm, 4 mm to 7 mm, 4 mm to 6 mm, 4 mm to 5 mm, 4.5 mm to 8 mm, 4.5 mm to 7 mm, 4.5 mm to 6 mm, 4.5 mm to 5 mm, 5 mm to 8 mm, 5 mm to 7 mm, 5 mm to 6 mm, 5.5 mm to 8 mm, 5.5 mm to 7 mm, 5.5 mm to 6 mm, 6 mm to 8 mm, 6 mm to 7 mm, 6.5 mm to 8 mm, 6.5 mm to 7 mm, 7 mm to 8 mm, or 7.5 mm to 8 mm.

In some embodiments, a device of the disclosure (e.g., particle, capsule) comprises at least one pore or opening, e.g., to allow for the free flow of materials. In some embodiments, the mean pore size of a device is between about 0.1 μm to about 10 μm. For example, the mean pore size may be between 0.1 μm to 10 μm, 0.1 μm to 5 μm, 0.1 μm to 2 μm, 0.15 μm to 10 μm, 0.15 μm to 5 μm, 0.15 μm to 2 μm, 0.2 μm to 10 μm, 0.2 μm to 5 μm, 0.25 μm to 10 μm, 0.25 μm to 5 μm, 0.5 μm to 10 μm, 0.75 μm to 10 μm, 1 μm to 10 μm, 1 μm to 5 μm, 1 μm to 2 μm, 2 μm to 10 μm, 2 μm to 5 μm, or 5 μm to 10 μm. In some embodiments, the mean pore size of a device is between about 0.1 μm to 10 μm. In some embodiments, the mean pore size of a device is between about 0.1 μm to 5 μm. In some embodiments, the mean pore size of a device is between about 0.1 μm to 1 μm.

In some embodiments, the device comprises a semi-permeable, biocompatible membrane surrounding the antigen-expressing cells that are encapsulated in a polymer composition (e.g., an alginate hydrogel). The membrane pore size is selected to allow oxygen and other molecules important to cell survival and function to move through the semi-permeable membrane while preventing immune cells from traversing through the pores. In an embodiment, the semi-permeable membrane has a molecular weight cutoff of less than 1000 kD or between 50-700 kD, 70-300 kD, or between 70-150 kD, or between 70 and 130 kD.

In an embodiment, the device may contain a cell-containing compartment that is surrounded with a barrier compartment formed from a cell-free biocompatible material, such as the core-shell microcapsules described in Ma, M et al., *Adv. Healthc Mater.,* 2 (5): 667-672 (2012). Such a barrier compartment could be used with or without the semi-permeable membrane.

Cells in the cell-containing compartment(s) of a device of the disclosure may be encapsulated in a polymer composition. The polymer composition may comprise one or more hydrogel-forming polymers. In addition to the polymer composition in the cell-containing compartment(s), the device (e.g., macrodevice, particle, hydrogel capsule) may comprise or be formed from materials such as metals, metallic alloys, ceramics, polymers, fibers, inert materials, and combinations thereof. A device may be completely made up of one type of material, or may comprise other materials within the cell-containing compartment and any other compartments In some embodiments, the device comprises a metal or a metallic alloy. In an embodiment, one or more of the compartments in the device (e.g., the first compartment, the second compartment, or all compartments) comprises a metal or a metallic alloy. Exemplary metallic or metallic alloys include comprising titanium and titanium group alloys (e.g., nitinol, nickel titanium alloys, thermo-memory alloy materials), platinum, platinum group alloys, stainless steel, tantalum, palladium, zirconium, niobium, molybdenum, nickel-chrome, chromium molybdenum alloys, or certain cobalt alloys (e.g., cobalt-chromium and cobalt-chromium-nickel alloys, e.g., ELGILOY® and PHYNOX®). For example, a metallic material may be stainless steel grade 316 (SS 316L) (comprised of Fe, <0.3% C, 16-18.5% Cr, 10-14% Ni, 2-3% Mo, <2% Mn, <1% Si, <0.45% P, and <0.03% S). In metal-containing devices, the amount of metal (e.g., by % weight, actual weight) can be at least 5%, e.g., at least 5%, 10%, 20%, 30%, 40%, 50%, 60%, 70%, 80%, 90%, 95%, 99%, or more, e.g., w/w; less than 20%, e.g., less than 20%, 15%, 10%, 5%, 1%, 0.5%, 0.1%, or less.

In some embodiments, the device comprises a ceramic. In an embodiment, one or more of the compartments in the device (e.g., the first compartment, the second compartment, or all compartments) comprises a ceramic. Exemplary ceramic materials include oxides, carbides, or nitrides of the transition elements, such as titanium oxides, hafnium oxides, iridium oxides, chromium oxides, aluminum oxides, and zirconium oxides. Silicon based materials, such as silica, may also be used. In ceramic-containing devices, the amount of ceramic (e.g., by % weight, actual weight) can be at least 5%, e.g., at least 5%, 10%, 20%, 30%, 40%, 50%, 60%, 70%, 80%, 90%, 95%, 99%, or more, e.g., w/w; less than 20%, e.g., less than 20%, 15%, 10%, 5%, 1%, 0.5%, 0.1%, or less.

In some embodiments, the device has two hydrogel compartments, in which the inner, cell-containing compartment is completely surrounded by the second, outer (e.g., barrier) compartment. In an embodiment, the inner boundary of the second compartment forms an interface with the outer boundary of the first compartment. In such embodiments, the thickness of the second (outer) compartment means the average distance between the outer boundary of the second compartment and the interface between the two compartments, e.g., the average of the distances measured at each of the thinnest and thickest points visually observed in the outer compartment. In some embodiments (e.g., the device is about 1.5 mm in diameter), the thinnest and thickest distances for the outer compartment are between 25 and 110 micrometers (μm) and between 270 and 480 μm, respectively. In some embodiments, the thickness of the outer compartment is greater than about 10 nanometers (nm), preferably 100 nm or greater and can be as large as 1 millimeter (mm). For example, the thickness (e.g., average distance) of the outer compartment in a hydrogel capsule device described herein may be 10 nm to 1 mm, 100 nm to 1 mm, 500 nm to 1 millimeter, 1 micrometer (μm) to 1 mm, 1 μm to 1 mm, 1 μm to 500 μm, 1 μm to 250 μm, 1 μm to 1 mm, 5 μm to 500 μm, 5 μm to 250 μm, 10 μm to 1 mm, 10 μm to 500 μm, or 10 μm to 250 μm. In some embodiments, the thickness (e.g., average distance) of the outer compartment is 100 nm to 1 mm, between 1 μm and 1 mm, between 1 μm and 500 μm or between 5 μm and 1 mm. In some embodiments, the thickness (e.g., average distance) of the outer compartment is between about 50 μm and about 100 μm. In some embodiments (e.g., the device is about 1.5 mm in diameter), the thickness of the outer compartment (e.g., average distance) is between about 180 μm and 260 μm or between about 310 μm and 440 μm.

In some embodiments of a two-compartment hydrogel capsule device, the mean pore size of the cell-containing inner compartment and the outer compartment is substantially the same. In some embodiments, the mean pore size of the inner compartment and the second compartment differ by about 1.5%, 2%, 5%, 7.5%, 10%, 15%, 20%, 25%, 30%, 35%, 40%, 45%, 50%, 55%, 60%, 65%, 70%, 75%, or more. In some embodiments, the mean pore size of the device (e.g., mean pore size of the first compartment and/or mean pore size of the second compartment) is dependent on a number of factors, such as the material(s) within each compartment and the presence and density of a compound of Formula (I).

The device may form part of a plurality of substantially the same devices in a preparation (e.g., composition). In some embodiments, the devices (e.g., particles, hydrogel capsules) in the preparation have a mean diameter or size between about 0.5 mm to about 8 mm. In some embodiments, the mean diameter or size of devices in the preparation is between about 0.5 mm to about 4 mm or between about 0.5 mm to about 2 mm. In some embodiments, the devices in the preparation are two-compartment hydrogel capsules and have a mean diameter or size of about 0.7 mm to about 1.3 mm or about 1.2 mm to about 1.8 mm.

In some embodiments, the surface of the device comprises a compound capable of mitigating the FBR, an afibrotic compound as described herein below. For devices comprising a barrier compartment surrounding the cell-containing compartment, the afibrotic compound may covalently modify a polymer disposed throughout the barrier compartment and optionally throughout the cell-containing compartment.

In some embodiments, one or more compartments in a device comprises an afibrotic polymer, e.g., an afibrotic compound of Formula (I) covalently attached to a polymer. In an embodiment, some or all the monomers in the afibrotic polymer are modified with the same compound of Formula (I). In some embodiments, some or all the monomers in the afibrotic polymer are modified with different compounds of Formula (I). In some embodiments in which the device is a 2-compartment hydrogel capsule, the afibrotic polymer is present only in the outer, barrier compartment.

One or more compartments in a device may comprise an unmodified polymer that is the same or different than the polymer in any afibrotic polymer that is present in the device. In an embodiment, the first compartment, second compartment or all compartments in the device comprise the unmodified polymer.

Each of the modified and unmodified polymers in the device may be a linear, branched, or cross-linked polymer, or a polymer of selected molecular weight ranges, degree of polymerization, viscosity or melt flow rate. Branched polymers can include one or more of the following types: star polymers, comb polymers, brush polymers, dendronized polymers, ladders, and dendrimers. A polymer may be a thermoresponsive polymer, e.g., gel (e.g., becomes a solid or liquid upon exposure to heat or a certain temperature) or a photocrosslinkable polymer. Exemplary polymers include polystyrene, polyethylene, polypropylene, polyacetylene, poly(vinyl chloride) (PVC), polyolefin copolymers, poly (urethane) s, polyacrylates and polymethacrylates, polyacrylamides and polymethacrylamides, poly (methyl methacrylate), poly (2-hydroxyethyl methacrylate), polyesters, polysiloxanes, polydimethylsiloxane (PDMS), polyethers, poly (orthoester), poly (carbonates), poly(hydroxyalkanoate) s, polyfluorocarbons, PEEK®, Teflon® (polytetrafluoroethylene, PTFE), PEEK, silicones, epoxy resins, Kevlar®, Dacron® (a condensation polymer obtained from ethylene glycol and terephthalic acid), polyethylene glycol, nylon, polyalkenes, phenolic resins, natural and synthetic elastomers, adhesives and sealants, polyolefins, polysulfones, polyacrylonitrile, biopolymers such as polysaccharides and natural latex, collagen, cellulosic polymers (e.g., alkyl celluloses, etc.), polyethylene glycol and 2-hydroxyethyl methacrylate (HEMA), polysaccharides, poly (glycolic acid), poly (L-lactic acid) (PLLA), poly(lactic glycolic acid) (PLGA), a polydioxanone (PDA), or racemic poly(lactic acid), polycarbonates, (e.g., polyamides (e.g., nylon)), fluoroplastics, carbon fiber, agarose, alginate, chitosan, and blends or copolymers thereof. In polymer-containing devices, the amount of a polymer (e.g., by % weight of the device, actual weight of the polymer) can be at least 5%, e.g., at least 5%, 10%, 20%, 30%, 40%, 50%, 60%, 70%, 80%, 90%, 95%, 99%, or more, e.g., w/w; less than 20%, e.g., less than 20%, 15%, 10%, 5%, 1%, 0.5%, 0.1%, or less.

In some embodiments, one or more of the modified and unmodified polymers in the device comprises a polyethylene. Exemplary polyethylenes include ultra-low-density polyethylene (ULDPE) (e.g., with polymers with densities ranging from 0.890 to 0.905 g/cm$^3$, containing comonomer); very-low-density polyethylene (VLDPE) (e.g., with polymers with densities ranging from 0.905 to 0.915 g/cm$^3$, containing comonomer); linear low-density polyethylene (LLDPE) (e.g., with polymers with densities ranging from 0.915 to 0.935 g/cm$^3$, contains comonomer); low-density polyethylene (LDPE) (e.g., with polymers with densities ranging from about 0.915 to 0.935 g/m$^3$); medium density polyethylene (MDPE) (e.g., with polymers with densities ranging from 0.926 to 0.940 g/cm$^3$, may or may not contain comonomer); high-density polyethylene (HDPE) (e.g., with polymers with densities ranging from 0.940 to 0.970 g/cm$^3$, may or may not contain comonomer) and polyethylene glycol.

In some embodiments, one or more of the modified and unmodified polymers in the device comprises a polypropylene. Exemplary polypropylenes include homopolymers, random copolymers (homophasic copolymers), and impact copolymers (heterophasic copolymers), e.g., as described in McKeen, *Handbook of Polymer Applications in Medicine and Medical Devices,* 3-Plastics Used in Medical Devices, (2014): 21-53.

In some embodiments, one or more of the modified and unmodified polymers in the device comprises a polypropylene. Exemplary polystyrenes include general purpose or crystal (PS or GPPS), high impact (HIPS), and syndiotactic (SPS) polystyrene.

In some embodiments, one or more of the modified and unmodified polymers comprises a comprises a thermoplastic elastomer (TPE). Exemplary TPEs include (i) TPA-polyamide TPE, comprising a block copolymer of alternating hard and soft segments with amide chemical linkages in the hard blocks and ether and/or ester linkages in the soft blocks; (ii) TPC-co-polyester TPE, consisting of a block copolymer of alternating hard segments and soft segments, the chemical linkages in the main chain being ester and/or ether; (iii) TPO-olefinic TPE, consisting of a blend of a polyolefin and a conventional rubber, the rubber phase in the blend having little or no cross-linking; (iv) TPS-styrenic TPE, consisting of at least a triblock copolymer of styrene and a specific diene, where the two end blocks (hard blocks) are polystyrene and the internal block (soft block or blocks) is a polydiene or hydrogenated polydiene; (v) TPU-urethane TPE, consisting of a block copolymer of alternating hard and soft segments with urethane chemical linkages in the hard blocks and ether, ester or carbonate linkages or mixtures of them in the soft blocks; (vi) TPV-thermoplastic rubber vulcanizate consisting of a blend of a thermoplastic material and a conventional rubber in which the rubber has been cross-linked by the process of dynamic vulcanization during the blending and mixing step; and (vii) TPZ-unclassified TPE comprising any composition or structure other than those grouped in TPA, TPC, TPO, TPS, TPU, and TPV.

In some embodiments, the unmodified polymer is an unmodified alginate. In some embodiments, the alginate is a high guluronic acid (G) alginate, and comprises greater than about 50%, 55%, 60%, 65%, 70%, 75%, 80%, 85%, 90%, or more guluronic acid (G). In some embodiments, the alginate is a high mannuronic acid (M) alginate, and comprises greater than about 50%, 55%, 60%, 65%, 70%, 75%, 80%, 85%, 90%, or more mannuronic acid (M). In some embodiments, the ratio of M:G is about 1. In some embodiments, the ratio of M:G is less than 1. In some embodiments, the ratio of M:G is greater than 1. In an embodiment, the unmodified alginate has a molecular weight of 150 kDa-250 kDa and a G: M ratio of ≥1 S.

In some embodiments, the afibrotic polymer comprises an alginate chemically modified with a Compound of Formula (I). The alginate in the afibrotic polymer may be the same or different than any unmodified alginate that is present in the device. In an embodiment, the density of the Compound of Formula (I) in the afibrotic alginate (e.g., amount of conjugation) is between about 4.0% and about 8.0%, between about 5.0% and about 7.0%, or between about 6.0% and about 7.0% nitrogen (e.g., as determined by combustion analysis for percent nitrogen). In an embodiment, the amount of Compound 101 produces an increase in % N (as compared with the unmodified alginate) of about 0.5% to 2% 2% to 4% N, about 4% to 6% N, about 6% to 8%, or about 8% to 10% N), where % N is determined by combustion analysis and corresponds to the amount of Compound 101 in the modified alginate.

In other embodiments, the density (e.g., concentration) of the Compound of Formula (I) (e.g., Compound 101) in the afibrotic alginate is defined as the % w/w, e.g., % of weight of amine/weight of afibrotic alginate in solution (e.g., saline) as determined by a suitable quantitative amine conjugation assay (e.g. by an assay described in WO2020069429), and in certain embodiments, the density of a Compound of Formula (I) (e.g., Compound 101) is between about 1.0% w/w and about 3.0% w/w, between about 1.3% w/w and about 2.5% w/w or between about 1.5% w/w and 2.2% w/w.

In alginate-containing devices, the amount of modified and unmodified alginates (e.g., by % weight of the device, actual weight of the alginate) can be at least 5%, e.g., at least 5%, 10%, 20%, 30%, 40%, 50%, 60%, 70%, 80%, 90%, 95%, 99%, or more, e.g., w/w; less than 20%, e.g., less than 20%, 15%, 10%, 5%, 1%, 0.5%, 0.1%, or less.

The alginate in an afibrotic polymer can be chemically modified with a compound of Formula (I) using any suitable method known in the art. For example, the alginate carboxylic acid moiety can be activated for coupling to one or more amine-functionalized compounds to achieve an alginate modified with a compound of Formula (I). The alginate polymer may be dissolved in water (30 mL/gram polymer) and treated with 2-chloro-4,6-dimethoxy-1,3,5-triazine (0.5 eq) and N-methylmorpholine (1 eq). To this mixture may be added a solution of the compound of Formula (I) in acetonitrile (0.3M). The reaction may be warmed to 55° C. for 16 h, then cooled to room temperature and gently concentrated via rotary evaporation, then the residue may be dissolved, e.g., in water. The mixture may then be filtered, e.g., through a bed of cyano-modified silica gel (Silicycle) and the filter cake washed with water. The resulting solution may then be dialyzed (10,000 MWCO membrane) against water for 24 hours, e.g., replacing the water twice. The resulting solution can be concentrated, e.g., via lyophilization, to afford the desired chemically modified alginate.

In an embodiment, the device comprises at least one cell-containing compartment, and in some embodiments contains two, three, four or more cell-containing compartments. In an embodiment, each cell-containing compartment comprises a plurality of cells (e.g., live cells) and the cells in at least one of the compartments are capable of expressing and secreting at least one antigen when the device is implanted into a subject. In some embodiments, the cells in a single cell-containing compartment express two or more antigens of the same infectious agent, e.g., an antigen cocktail intended to induce a protective immune response to the agent. In some embodiments, the cells in a cell-containing compartment express one or more antigens of at least two infectious agents.

In an embodiment, all the cells in a cell-containing compartment are derived from a single parental cell-type or a mixture of at least two different parental cell types. In an embodiment, all of the cells in a cell-containing compartment are derived from the same parental cell type, but a first plurality of the derived cells are engineered to express a first antigen or antigen cocktail, and a second plurality of the derived cells are engineered to express a second antigen or antigen cocktail. In devices with two or more cell-containing compartments, the cells and the antigen(s) produced thereby may be the same or different in each cell-containing compartment. In some embodiments, all of the cell-containing compartments are surrounded by a single barrier compartment. In some embodiments, the barrier compartment is substantially cell-free.

In an embodiment, cells to be incorporated into a device described herein, e.g., a hydrogel capsule, are prepared in the form of a cell suspension prior to being encapsulated within the device. The cells in the suspension may take the form of single cells (e.g., from a monolayer cell culture), or provided in another form, e.g., disposed on a microcarrier (e.g., a bead or matrix) or as a three-dimensional aggregate of cells (e.g., a cell cluster or spheroid). The cell suspension can comprise multiple cell clusters (e.g., as spheroids) or microcarriers.

In addition to antigen(s) expressed by the encapsulated cells, a device (e.g., capsule, particle) may comprise one or more exogenous agents that are not expressed by the cells, and may include, e.g., a nucleic acid (e.g., an RNA or DNA molecule), a protein (e.g., a hormone, an enzyme (e.g., glucose oxidase, kinase, phosphatase, oxygenase, hydrogenase, reductase) antibody, antibody fragment, antigen, or epitope)), an active or inactive fragment of a protein or polypeptide, a small molecule, or drug. In an embodiment, the device is configured to release such an exogenous agent.

A device described herein may be provided as a preparation or composition for implantation or administration to a subject, i.e., a device preparation or device composition, e.g., a vaccine composition. In some embodiments, a device preparation or composition comprises at least 2, 4, 8, 16, 32, 64 or more devices, and at least 20%, 30%, 35%, 40%, 45%, 50%, 55%, 60%, 65%, 70%, 75%, 80%, 85%, 90%, 95% or 100% of the devices in the preparation or composition have a characteristic as described herein, e.g., mean diameter or mean pore size or cell density.

A device or vaccine composition may be configured for implantation, or implanted or disposed into or onto any site of the body. In some embodiments, a device, preparation or composition is configured for implantation, implanted or disposed into the subcutaneous fat of a subject, or into the muscle tissue of a subject. In some embodiments, the device, device preparation or device composition is configured for implantation or implanted or disposed into the peritoneal cavity (e.g., the omentum). In some embodiments, the device is configured for implantation or implanted or disposed into or onto the lesser sac, also known as the omental bursa or bursalis omentum. The lesser sac refers to a cavity located in the abdomen formed by the omentum, and is in close proximity to, for example, the greater omentum, lesser omentum, stomach, small intestine, large intestine, liver, spleen, gastrosplenic ligament, adrenal glands, and pancreas. Typically, the lesser sac is connected to the greater sac via the omental foramen (i.e., the Foramen of Winslow). In some embodiments, the lesser sac comprises a high concentration of adipose tissue. A device, device preparation or device composition may be implanted in the peritoneal cavity (e.g., the omentum, e.g., the lesser sac) or disposed on a surface within the peritoneal cavity (e.g., omentum, e.g., lesser sac) via injection or catheter. Additional considerations for implantation or disposition of a device, preparation or composition into the omentum (e.g., the lesser sac) are provided in M. Pellicciaro et al. (2017) CellR4 5(3): e2410.

In some embodiments, a device or preparation is easily retrievable from a subject, e.g., without causing injury to the subject or without causing significant disruption of the surrounding tissue. In an embodiment, the device or preparation can be retrieved with minimal or no surgical separation of the device(s) from surrounding tissue, e.g., via minimally invasive surgical approach, extraction, or resection.

A device, composition or preparation can be configured to provide continuous antigen delivery for a variety of time periods after implant into a mammalian recipient, including: a short continuous delivery (e.g., less than 2 days, e.g., less than 2 days, 1 day, 24 hours, 20 hours, 16 hours, 12 hours, 10 hours, 8 hours, 6 hours, 5 hours, 4 hours, 3 hours, 2 hours, 1 hour or less) or prolonged antigen delivery (e.g., at least 2 days, 3 days, 4 days, 5 days, 6 days, 7 days, 1 week, 2 weeks, 3 weeks, 4 weeks, 5 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months or longer).

In some embodiments, the device is not any capsule, device, implant or other object disclosed in any of WO2012/112982, WO2012/167223, WO2014/153126, WO2016/019391, WO2016/187225, WO 2018/232027, WO 2019/068059, WO 2019/169089, US2012-0213708, US 2016-0030359, and US 2016-0030360.

Small Molecule Compounds

In some embodiments, the devices described herein comprise at least one compound of Formula (I):

(I)

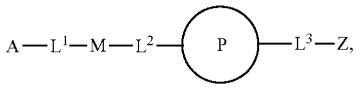

or a pharmaceutically acceptable salt thereof, wherein:

A is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)C(O)($C_1$-$C_6$-alkylene)-, —N($R^C$)C(O)($C_1$-$C_6$-alkenylene)-, —N($R^C$)N($R^D$)—, —NCN—, —C(=N($R^C$)($R^D$))O—, —S—, —S(O)$_x$—, —OS(O)$_x$—, —N($R^C$)S(O)$_x$—, —S(O)$_x$N($R^C$)—, —P($R^F$)$_y$—, —Si($OR^A$)$_2$—, —Si($R^G$)($OR^A$)—, —B($OR^A$), or a metal, each of which is optionally linked to an attachment group (e.g., an attachment group described herein) and is optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond;

M is absent, alkyl, heteroalkyl, cycloalkyl, heterocyclyl, aryl, or heteroaryl, each of which is optionally substituted by one or more $R^3$;

P is absent, cycloalkyl, heterocyclyl, or heteroaryl, each of which is optionally substituted by one or more $R^4$;

Z is hydrogen, alkyl, alkenyl, alkynyl, heteroalkyl, —$OR^A$, —C(O)$R^A$, —C(O)$OR^A$, —C(O)N($R^C$)($R^D$), —N($R^C$)C(O)$R^A$, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring (e.g., a 5-7 membered ring), optionally substituted with one or more $R^6$, each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), $SR^{E1}$, S(O)$_x$$R^{E1}$, —OS(O)$_x$$R^{E1}$, —N($R^{C1}$)S(O)$_x$$R^{E1}$, —S(O)$_x$N($R^{C1}$)($R^{D1}$), —P($R^{F1}$); cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

In some embodiments, the compound of Formula (I) is a compound of Formula (I-a):

(I-a)

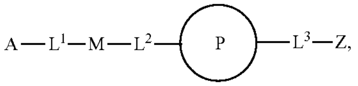

or a pharmaceutically acceptable salt thereof, wherein:

A is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)N($R^D$), N($R^C$)C(O)($C_1$-$C_6$-alkylene)-, —N($R^C$)C(O)($C_1$-$C_6$-alkenylene)-, —NCN—, —C(=N($R^C$)($R^D$))O—, —S—, —S(O)—, —OS(O)—, —N($R^C$)S(O)$_x$—, —S(O)$_x$N($R^C$)—, —P($R^F$)$_y$—, —Si($OR^A$)$_2$—, —Si($R^G$)($OR^A$)—, —B($OR^A$), or a metal, each of which is optionally linked to an attachment group (e.g., an attachment group described herein) and optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond;

M is absent, alkyl, heteroalkyl, cycloalkyl, heterocyclyl, aryl, or heteroaryl, each of which is optionally substituted by one or more $R^3$;

P is heteroaryl optionally substituted by one or more $R^4$;

Z is alkyl, alkenyl, alkynyl, heteroalkyl, cycloalkyl, heterocyclyl, aryl, or heteroaryl, each of which is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring (e.g., a 5-7 membered ring), optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), $SR^{E1}$, S(O)$_x$$R^{E1}$, —OS(O)$_x$$R^{E1}$, —N($R^{C1}$)S(O)$_x$$R^{E1}$, —S(O)$_x$N($R^{C1}$)($R^{D1}$), —P($R^{F1}$)$_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

In some embodiments, for Formulas (I) and (I-a), A is alkyl, alkenyl, alkynyl, heteroalkyl, cycloalkyl, heterocyclyl, aryl, heteroaryl, —O—, —C(O)O—, —C(O)—, —OC(O)—, —N($R^C$)C(O)—, —N($R^C$)C(O)($C_1$-$C_6$-alkylene)-, —N($R^C$)C(O)($C_1$-$C_6$-alkenylene)-, or —N($R^C$). In some embodiments, A is alkyl, alkenyl, alkynyl, heteroalkyl, cycloalkyl, heterocyclyl, aryl, heteroaryl, —O—, —C(O)O—, —C(O)—, —OC(O)—, or —N($R^C$)—. In some embodiments, A is alkyl, alkenyl, alkynyl, heteroalkyl, —O—, —C(O)O—, —C(O)—, —OC(O)—, or —N($R^C$)—. In some embodiments, A is alkyl, —O—, —C(O)O—, —C(O)—, —OC(O), or —N($R^C$)—. In some embodiments, A is —N($R^C$)C(O)—, —N($R^C$)C(O)($C_1$-$C_6$-alkylene)-, or —N($R^C$)C(O)($C_1$-$C_6$-alkenylene)-. In some embodiments, A is —N($R^C$)—. In some embodiments, A is —N($R^C$)—, and $R^C$ an $R^D$ is independently hydrogen or alkyl. In some embodiments, A is —NH—. In some embodiments, A is —N($R^C$)C(O)($C_1$-$C_6$-alkylene)-, wherein alkylene is substituted with $R^1$. In some embodiments, A is —N($R^C$)C(O)($C_1$-$C_6$-alkylene)-, and $R^1$ is alkyl (e.g., methyl). In some embodiments, A is —NHC(O)C($CH_3$)$_2$—. In some embodiments, A is —N($R^C$)C(O)(methylene)-, and $R^1$ is alkyl (e.g., methyl). In some embodiments, A is —NHC(O)CH($CH_3$)—. In some embodiments, A is —NHC(O)C($CH_3$)—.

In some embodiments, for Formulas (I) and (I-a), L' is a bond, alkyl, or heteroalkyl. In some embodiments, $L^1$ is a bond or alkyl. In some embodiments, L' is a bond. In some embodiments, $L^1$ is alkyl. In some embodiments, L' is $C_1$-$C_6$ alkyl. In some embodiments, $L^1$ is —$CH_2$—, —CH ($CH_3$), —$CH_2CH_2CH_2$, or —$CH_2CH_2$—. In some embodiments, $L^1$ is —$CH_2$— or —$CH_2CH_2$—.

In some embodiments, for Formulas (I) and (I-a), $L^3$ is a bond, alkyl, or heteroalkyl. In some embodiments, $L^3$ is a bond. In some embodiments, $L^3$ is alkyl. In some embodiments, $L^3$ is $C_1$-$C_{12}$ alkyl. In some embodiments, $L^3$ is $C_1$-$C_6$ alkyl. In some embodiments, $L^3$ is —$CH_2$—. In some embodiments, $L^3$ is heteroalkyl. In some embodiments, $L^3$ is $C_1$-$C_{12}$ heteroalkyl, optionally substituted with one or more $R^2$ (e.g., oxo). In some embodiments, $L^3$ is $C_1$-$C_6$ heteroalkyl, optionally substituted with one or more $R^2$ (e.g., oxo). In some embodiments, $L^3$ is —C(O)$OCH_2$—, —$CH_2$($OCH_2CH_2$)$_2$—, —$CH_2$($OCH_2CH_2$)$_3$—, $CH_2CH_2O$—, or —$CH_2O$—. In some embodiments, $L^3$ is —$CH_2O$—.

In some embodiments, for Formulas (I) and (I-a), M is absent, alkyl, heteroalkyl, aryl, or heteroaryl. In some embodiments, M is heteroalkyl, aryl, or heteroaryl. In some embodiments, M is absent. In some embodiments, M is alkyl (e.g., $C_1$-$C_6$ alkyl). In some embodiments, M is —$CH_2$—. In some embodiments, M is heteroalkyl (e.g., $C_1$-$C_6$ heteroalkyl). In some embodiments, M is (—$OCH_2CH_2$-)z, wherein z is an integer selected from 1 to 10. In some embodiments, z is an integer selected from 1 to 5. In some embodiments, M is —$OCH_2CH_2$—, (—$OCH_2CH_2$-)$_2$, (—$OCH_2CH_2$-)$_3$, (—$OCH_2CH_2$-)$_4$, or (—$OCH_2CH_2$-)$_5$. In some embodiments, M is —$OCH_2CH_2$—, (—$OCH_2CH_2$-)$_2$, (—$OCH_2CH_2$-)$_3$, or (—$OCH_2CH_2$-)$_4$. In some embodiments, M is (—$OCH_2CH_2$-)$_3$. In some embodiments, M is aryl. In some embodiments, M is phenyl. In some embodiments, M is unsubstituted phenyl. In some embodiments, M is

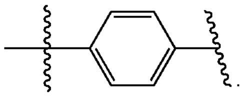

In some embodiments, M is phenyl substituted with $R^7$ (e.g., 1 $R^7$). In some embodiments, M is (1-4)

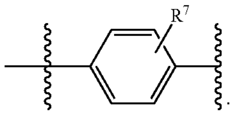

In some embodiments, $R^7$ is $CF_3$.

In some embodiments, for Formulas (I) and (I-a), P is absent, heterocyclyl, or heteroaryl. In some embodiments, P is absent. In some embodiments, for Formulas (I) and (I-a), P is a tricyclic, bicyclic, or monocyclic heteroaryl. In some embodiments, P is a monocyclic heteroaryl. In some embodiments, P is a nitrogen-containing heteroaryl. In some embodiments, P is a monocyclic, nitrogen-containing heteroaryl. In some embodiments, P is a 5-membered heteroaryl. In some embodiments, P is a 5-membered nitrogen-containing heteroaryl. In some embodiments, P is tetrazolyl, imidazolyl, pyrazolyl, or triazolyl, pyrrolyl, oxazolyl, or thiazolyl. In some embodiments, P is tetrazolyl, imidazolyl, pyrazolyl, or triazolyl, or pyrrolyl. In some embodiments, P is imidazolyl. In some embodiments, P is

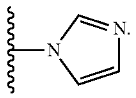

In some embodiments, P is triazolyl. In some embodiments, P is 1,2,3-triazolyl. In some embodiments, P is

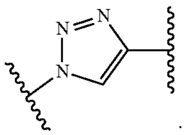 [SMILES: *c1cn(*)nn1]

In some embodiments, P is heterocyclyl. In some embodiments, P is a 5-membered heterocyclyl or a 6-membered heterocyclyl. In some embodiments, P is imidazolidinonyl. In some embodiments, P is

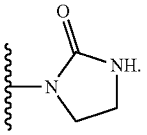 [SMILES: *N1CCNC1=O]

In some embodiments, P is thiomorpholinyl-1,1-dioxidyl. In some embodiments, P is

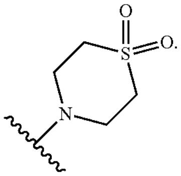 [SMILES: *N1CCS(=O)(=O)CC1]

In some embodiments, for Formulas (I) and (I-a), Z is alkyl, heteroalkyl, cycloalkyl, heterocyclyl, aryl, or heteroaryl. In some embodiments, Z is heterocyclyl. In some embodiments, Z is monocyclic or bicyclic heterocyclyl. In some embodiments, Z is an oxygen-containing heterocyclyl. In some embodiments, Z is a 4-membered heterocyclyl, 5-membered heterocyclyl, or 6-membered heterocyclyl. In some embodiments, Z is a 6-membered heterocyclyl. In some embodiments, Z is a 6-membered oxygen-containing heterocyclyl. In some embodiments, Z is tetrahydropyranyl. In some embodiments, Z is

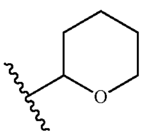, 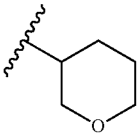, or 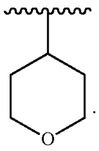.

In some embodiments, Z is a 4-membered oxygen-containing heterocyclyl. In some embodiments, Z is

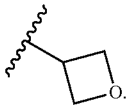

In some embodiments, Z is a bicyclic oxygen-containing heterocyclyl. In some embodiments, Z is phthalic anhydridyl. In some embodiments, Z is a sulfur-containing heterocyclyl. In some embodiments, Z is a 6-membered sulfur-containing heterocyclyl. In some embodiments, Z is a 6-membered heterocyclyl containing a nitrogen atom and a sulfur atom. In some embodiments, Z is thiomorpholinyl-1,1-dioxidyl. In some embodiments, Z is

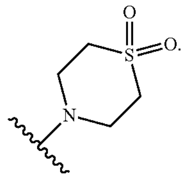 [SMILES: *N1CCS(=O)(=O)CC1]

In some embodiments, Z is a nitrogen-containing heterocyclyl. In some embodiments, Z is a 6-membered nitrogen-containing heterocyclyl. In some embodiments, Z is

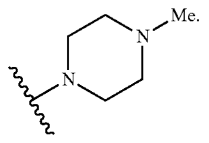 [SMILES: *N1CCN(C)CC1]

In some embodiments, Z is a bicyclic heterocyclyl. In some embodiments, Z is a bicyclic nitrogen-containing heterocyclyl, optionally substituted with one or more $R^5$. In some embodiments, Z is 2-oxa-7-azaspiro[3.5]nonanyl. In some embodiments, Z is

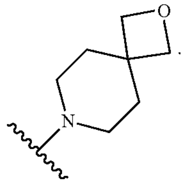 [SMILES: *N1CCC2(CC1)COC2]

In some embodiments, Z is 1-oxa-3,8-diazaspiro[4.5]decan-2-one. In some embodiments, Z is

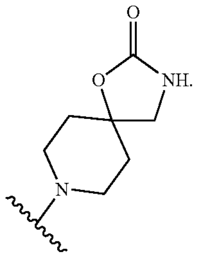 [SMILES: *N1CCC2(CC1)CNC(=O)O2]

In some embodiments, for Formulas (I) and (I-a), Z is aryl. In some embodiments, Z is monocyclic aryl. In some embodiments, Z is phenyl. In some embodiments, Z is monosubstituted phenyl (e.g., with 1 $R^5$). In some embodiments, Z is monosubstituted phenyl, wherein the 1 $R^5$ is a nitrogen-containing group. In some embodiments, Z is monosubstituted phenyl, wherein the 1 $R^5$ is $NH_2$. In some embodiments, Z is monosubstituted phenyl, wherein the 1 $R^5$ is an oxygen-containing group. In some embodiments, Z is monosubstituted phenyl, wherein the 1 $R^5$ is an oxygen-containing heteroalkyl. In some embodiments, Z is monosubstituted phenyl, wherein the 1 $R^5$ is $OCH_3$. In some embodiments, Z is monosubstituted phenyl, wherein the 1 $R^5$ is in the ortho position. In some embodiments, Z is monosubstituted phenyl, wherein the 1 $R^5$ is in the meta position. In some embodiments, Z is monosubstituted phenyl, wherein the 1 $R^5$ is in the para position.

In some embodiments, for Formulas (I) and (I-a), Z is alkyl. In some embodiments, Z is $C_1$-$C_{12}$ alkyl. In some embodiments, Z is $C_1$-$C_{10}$ alkyl. In some embodiments, Z is $C_1$-$C_8$ alkyl. In some embodiments, Z is $C_1$-$C_8$ alkyl substituted with 1-5 $R^5$. In some embodiments, Z is $C_1$-$C_8$ alkyl substituted with 1 $R^5$. In some embodiments, Z is $C_1$-$C_8$ alkyl substituted with 1 $R^5$, wherein $R^5$ is alkyl, heteroalkyl, halogen, oxo, —$OR^{A1}$, $C(O)OR^{A1}$, —$C(O)R^{B1}$, —$OC(O)R^{B1}$, or —$N(R^{C1})(R^{D1})$. In some embodiments, Z is $C_1$-$C_8$ alkyl substituted with 1 $R^5$, wherein $R^5$ is —$OR^{A1}$ or —$C(O)OR^{A1}$. In some embodiments, Z is $C_1$-$C_8$ alkyl substituted with 1 $R^5$, wherein $R^5$ is —$OR^{A1}$ or —C(O)OH. In some embodiments, Z is —$CH_3$.

In some embodiments, for Formulas (I) and (I-a), Z is heteroalkyl. In some embodiments, Z is $C_1$-$C_{12}$ heteroalkyl. In some embodiments, Z is $C_1$-$C_{10}$ heteroalkyl. In some embodiments, Z is $C_1$-$C_8$ heteroalkyl. In some embodiments, Z is $C_1$-$C_6$ heteroalkyl. In some embodiments, Z is a nitrogen-containing heteroalkyl optionally substituted with one or more $R^5$. In some embodiments, Z is a nitrogen and sulfur-containing heteroalkyl substituted with 1-5 $R^5$. In some embodiments, Z is N-methyl-2-(methylsulfonyl)ethan-1-aminyl.

In some embodiments, Z is —$OR^A$ or —$C(O)OR^A$. In some embodiments, Z is —$OR^A$ (e.g., —OH or —$OCH_3$). In some embodiments, Z is —$OCH_3$. In some embodiments, Z is —$C(O)OR^A$ (e.g., —C(O)OH).

In some embodiments, Z is hydrogen.

In some embodiments, $L^2$ is a bond and P and $L^3$ are independently absent. In some embodiments, $L^2$ is a bond, P is heteroaryl, $L^3$ is a bond, and Z is hydrogen. In some embodiments, P is heteroaryl, $L^3$ is heteroalkyl, and Z is alkyl.

In some embodiments, the compound of Formula (I) is a compound of Formula (I-b):

(I-b)

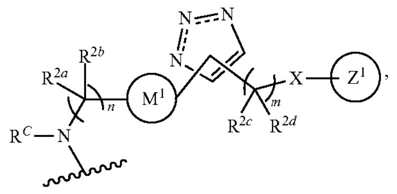

or a pharmaceutically acceptable salt thereof, wherein Ring $M^1$ is cycloalkyl, heterocyclyl, aryl, or heteroaryl, each of which is optionally substituted with 1-5 $R^3$; Ring $Z^1$ is cycloalkyl, heterocyclyl, aryl or heteroaryl, optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl, or each of $R^{2a}$ and $R^{2b}$ or $R^{2c}$ and $R^{2d}$ is taken together to form an oxo group; X is absent, $N(R^{10})(R^{11})$, O, or S; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$, each $R^3$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, cycloalkyl, heterocyclyl, aryl, or heteroaryl; each of $R^{10}$ and $R^{11}$ is independently hydrogen, alkyl, alkenyl, alkynyl, heteroalkyl, —C(O)OR$^{A1}$, —C(O)R$^{B1}$, —OC(O)R$^{B1}$, —C(O)N(R$^{C1}$), cycloalkyl, heterocyclyl, aryl, or heteroaryl; each R$^{A1}$, R$^{B1}$, R$^{C1}$, R$^{D1}$, and R$^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 R$^7$; each R$^7$ is independently alkyl, alkenyl, alkynyl, heteroalkyl, halogen, cyano, oxo, hydroxyl, cycloalkyl, or heterocyclyl; each m and n is independently 1, 2, 3, 4, 5, or 6; and "∿∿" refers to a connection to an attachment group or a polymer described herein. In some embodiments, for each R$^3$ and R$^5$, each alkyl, alkenyl, alkynyl, heteroalkyl, cycloalkyl, heterocyclyl, aryl, or heteroaryl is optionally and independently substituted with halogen, oxo, cyano, cycloalkyl, or heterocyclyl.

In some embodiments, the compound of Formula (I-b) is a compound of Formula (I-b-i):

(I-b-i)

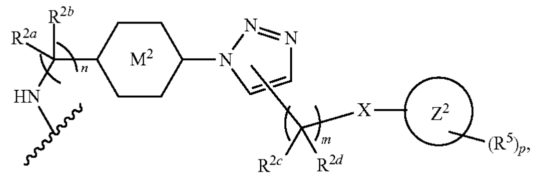

or a pharmaceutically acceptable salt thereof, wherein Ring M$^2$ is aryl or heteroaryl optionally substituted with one or more R$^3$; Ring Z$^2$ is cycloalkyl, heterocyclyl, aryl, or heteroaryl; each of R$^{2a}$, R$^{2b}$, R$^{2c}$, and R$^{2d}$ is independently hydrogen, alkyl, or heteroalkyl, or each of R$^{2a}$ and R$^{2b}$ or R$^{2c}$ and R$^{2d}$ is taken together to form an oxo group; X is absent, O, or S; each R$^3$ and R$^5$ is independently alkyl, heteroalkyl, halogen, oxo, —OR$^{A1}$, —C(O)OR$^{A1}$, or —C(O)R$^{B1}$, wherein each alkyl and heteroalkyl is optionally substituted with halogen; or two R$^5$ are taken together to form a 5-6 membered ring fused to Ring Z$^2$; each R$^{A1}$ and R$^{B1}$ is independently hydrogen, alkyl, or heteroalkyl; m and n are each independently 1, 2, 3, 4, 5, or 6; p is 0, 1, 2, 3, 4, 5, or 6; and "∿∿" refers to a connection to an attachment group or a polymer described herein.

In some embodiments, the compound of Formula (I-b-i) is a compound of Formula (I-b-ii):

(I-b-ii)

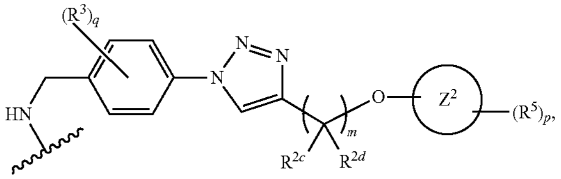

or a pharmaceutically acceptable salt thereof, wherein Ring Z$^2$ is cycloalkyl, heterocyclyl, aryl or heteroaryl; each of R$^{2c}$ and R$^{2d}$ is independently hydrogen, alkyl, or heteroalkyl, or R$^{2c}$ and R$^{2d}$ and taken together to form an oxo group; each R$^3$ and R$^5$ is independently alkyl, heteroalkyl, halogen, oxo, —OR$^{A1}$, —C(O)OR$^{A1}$, or —C(O)R$^{B1}$, wherein each alkyl and heteroalkyl is optionally substituted with halogen; each R$^{A1}$ and R$^{B1}$ is independently hydrogen, alkyl, or heteroalkyl; each of p and q is independently 0, 1, 2, 3, 4, 5, or 6; and "∿∿" refers to a connection to an attachment group or a polymer described herein.

In some embodiments, the compound of Formula (I) is a compound of Formula (I-c):

(I-c)

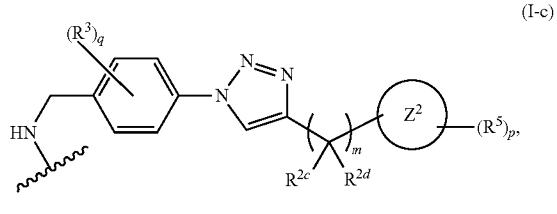

or a pharmaceutically acceptable salt thereof, wherein Ring Z$^2$ is cycloalkyl, heterocyclyl, aryl or heteroaryl; each of R$^{2c}$ and R$^{2d}$ is independently hydrogen, alkyl, or heteroalkyl, or R$^{2c}$ and R$^{2d}$ is taken together to form an oxo group; each R$^3$ and R$^5$ is independently alkyl, heteroalkyl, halogen, oxo, —OR$^{A1}$, —C(O)OR$^{A1}$, or —C(O)R$^{B1}$, wherein each alkyl and heteroalkyl is optionally substituted with halogen; each R$^{A1}$ and R$^{B1}$ is independently hydrogen, alkyl, or heteroalkyl; m is 1, 2, 3, 4, 5, or 6; each of p and q is independently 0, 1, 2, 3, 4, 5, or 6; and "∿∿" refers to a connection to an attachment group or a polymer described herein.

In some embodiments, the compound of Formula (I) is a compound of Formula (I-d):

(I-d)

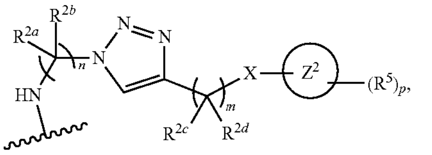

or a pharmaceutically acceptable salt thereof, wherein Ring Z$^2$ is cycloalkyl, heterocyclyl, aryl or heteroaryl; X is absent, O, or S; each of R$^{2a}$, R$^{2b}$, R$^{2c}$, and R$^{2d}$ is independently hydrogen, alkyl, or heteroalkyl, or each of R$^{2a}$ and R$^{2b}$ or R$^{2c}$ and R$^{2d}$ is taken together to form an oxo group; each R$^5$ is independently alkyl, heteroalkyl, halogen, oxo, —OR$^{A1}$, —C(O)OR$^{A1}$, or —C(O)R$^{B1}$, wherein each alkyl and heteroalkyl is optionally substituted with halogen; each R$^{A1}$ and R$^{B1}$ is independently hydrogen, alkyl, or heteroalkyl; each of m and n is independently 1, 2, 3, 4, 5, or 6; p is 0, 1, 2, 3, 4, 5, or 6; and "∿∿" refers to a connection to an attachment group or a polymer described herein.

In some embodiments, the compound of Formula (I) is a compound of Formula (I-e):

(I-e)

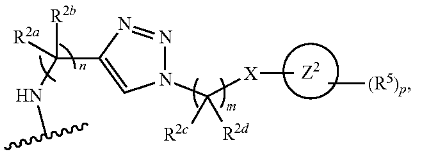

or a pharmaceutically acceptable salt thereof, wherein Ring Z$^2$ is cycloalkyl, heterocyclyl, aryl or heteroaryl; X is absent, O, or S; each of R$^{2a}$, R$^{2b}$, R$^{2c}$, and R$^{2d}$ is independently hydrogen, alkyl, or heteroalkyl, or each of $R^{2a}$ and $R^{2b}$ or $R^{2c}$ and $R^{2d}$ is taken together to form an oxo group; each $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; each of m and n is independently 1, 2, 3, 4, 5, or 6; p is 0, 1, 2, 3, 4, 5, or 6; and "∿∿" refers to a connection to an attachment group or a polymer described herein.

In some embodiments, the compound of Formula (I) is a compound of Formula (I-f):

(I-f)

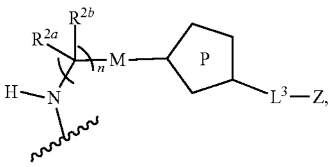

or a pharmaceutically acceptable salt thereof, wherein M is alkyl optionally substituted with one or more $R^3$; Ring P is heteroaryl optionally substituted with one or more $R^4$; $L^3$ is alkyl or heteroalkyl optionally substituted with one or more $R^2$; Z is alkyl, heteroalkyl, cycloalkyl, heterocyclyl, aryl, or heteroaryl, each of which is optionally substituted with one or more $R^5$; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, $R^4$, and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; n is independently 1, 2, 3, 4, 5, or 6; and "∿∿" refers to a connection to an attachment group or a polymer described herein.

In some embodiments, the compound of Formula (I) is a compound of Formula (II):

(II)

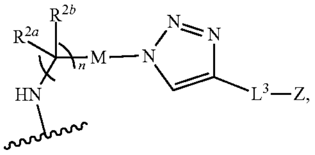

or a pharmaceutically acceptable salt thereof, wherein M is a bond, alkyl or aryl, wherein alkyl and aryl is optionally substituted with one or more $R^3$; $L^3$ is alkyl or heteroalkyl optionally substituted with one or more $R^2$; Z is hydrogen, alkyl, heteroalkyl, cycloalkyl, heterocyclyl, aryl, heteroaryl or —$OR^A$, wherein alkyl, heteroalkyl, cycloalkyl, heterocyclyl, aryl, and heteroaryl is optionally substituted with one or more $R^5$; $R^A$ is hydrogen; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; n is independently 1, 2, 3, 4, 5, or 6; and "∿∿" refers to a connection to an attachment group or a polymer described herein.

In some embodiments, the compound of Formula (II) is a compound of Formula (II-a):

(II-a)

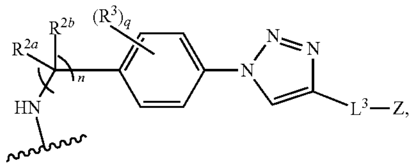

or a pharmaceutically acceptable salt thereof, wherein $L^3$ is alkyl or heteroalkyl, each of which is optionally substituted with one or more $R^2$; Z is hydrogen, alkyl, heteroalkyl, or —$OR^A$, wherein alkyl and heteroalkyl are optionally substituted with one or more $R^5$; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, and $R^5$ is independently alkyl, heteroalkyl, halogen, oxo, —$OR^{A1}$, —$C(O)OR^{A1}$, or —$C(O)R^{B1}$; $R^A$ is hydrogen; each $R^{A1}$ and $R^{B1}$ is independently hydrogen, alkyl, or heteroalkyl; n is independently 1, 2, 3, 4, 5, or 6; and "∿∿" refers to a connection to an attachment group or a polymer described herein.

In some embodiments, the compound of Formula (I) is a compound of Formula (III):

(III)

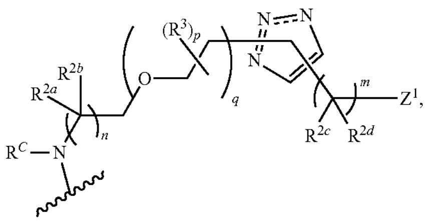

or a pharmaceutically acceptable salt thereof, wherein $Z^1$ is alkyl, alkenyl, alkynyl, heteroalkyl, cycloalkyl, heterocyclyl, aryl, or heteroaryl, each of which is optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; $R^C$ is hydrogen, alkyl, alkenyl, alkynyl, or heteroalkyl, wherein each of alkyl, alkenyl, alkynyl, or heteroalkyl is optionally substituted with 1-6 $R^6$; each of $R^3$, $R^5$, and $R^6$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; q is an integer from 0 to 25; and "∿∿" refers to a connection to an attachment group or a polymer described herein.

In some embodiments, the compound of Formula (III) is a compound of Formula (III-a):

(III-a)

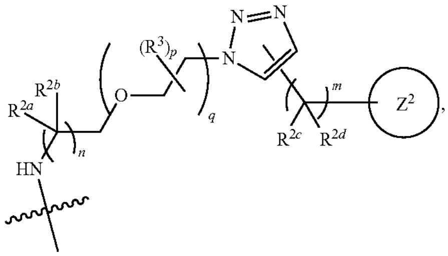

or a pharmaceutically acceptable salt thereof, wherein Ring $Z^2$ is cycloalkyl, heterocyclyl, aryl, or heteroaryl, each of which is optionally substituted with 1-5 $R^5$; each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; o and p are each independently 0, 1, 2, 3, 4, or 5; q is an integer from 0 to 25; and "∿∿" refers to a connection to an attachment group or a polymer described herein.

In some embodiments, the compound of Formula (III-a) is a compound of Formula (III-b):

(III-b)

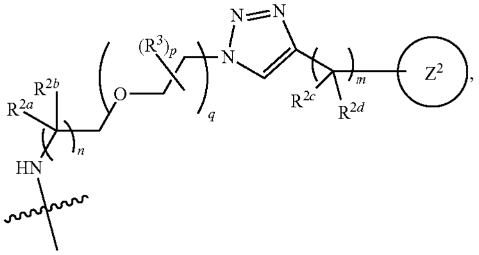

or a pharmaceutically acceptable salt thereof, wherein Ring $Z^2$ is cycloalkyl, heterocyclyl, aryl, or heteroaryl, each of which is optionally substituted with 1-5 $R^5$; each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; o and p are each independently 0, 1, 2, 3, 4, or 5; q is an integer from 0 to 25; and "∿∿" refers to a connection to an attachment group or a polymer described herein.

In some embodiments, the compound of Formula (III-a) is a compound of Formula (III-c):

(III-c)

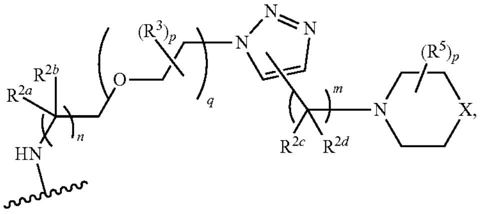

or a pharmaceutically acceptable salt thereof, wherein X is C(R')(R"), N(R'), or S (O) x; each of R' and R" is independently hydrogen, alkyl, halogen, or cycloalkyl; each of $R^{2a}$, $R^{2b}$, $R^{2c}$, and $R^{2d}$ is independently hydrogen, alkyl, heteroalkyl, or halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; p is 0, 1, 2, 3, 4, or 5; q is an integer from 0 to 25; x is 0, 1, or 2; and "∿∿" refers to a connection to an attachment group or a polymer described herein.

In some embodiments, the compound of Formula (III-c) is a compound of Formula (III-d):

(III-d)

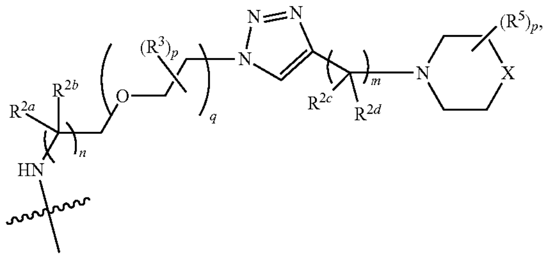

or a pharmaceutically acceptable salt thereof, wherein X is C(R')(R"), N(R'), or $S(O)_x$; each of R' and R" is independently hydrogen, alkyl, halogen, or cycloalkyl; each of $R^{2a}$, $R^{2b}$, $R^{2c}$, and $R^{2d}$ is independently hydrogen, alkyl, heteroalkyl, or halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; p is 0, 1, 2, 3, 4, or 5; q is an integer from 0 to 25; x is 0, 1, or 2; and "∿∿" refers to a connection to an attachment group or a polymer described herein.

In some embodiments, the compound is a compound of Formula (I). In some embodiments, $L^2$ is a bond and P and $L^3$ are independently absent.

In some embodiments, the compound is a compound of Formula (I-a). In some embodiments of Formula (II-a), $L^2$ is a bond, P is heteroaryl, $L^3$ is a bond, and Z is hydrogen. In some embodiments, P is heteroaryl, $L^3$ is heteroalkyl, and Z is alkyl. In some embodiments, $L^2$ is a bond and P and $L^3$ are independently absent. In some embodiments, $L^2$ is a bond, P is heteroaryl, $L^3$ is a bond, and Z is hydrogen. In some embodiments, P is heteroaryl, $L^3$ is heteroalkyl, and Z is alkyl.

In some embodiments, the compound is a compound of Formula (I-b). In some embodiments, P is absent, $L^1$ is —$NHCH_2$, $L^2$ is a bond, M is aryl (e.g., phenyl), $L^3$ is —$CH_2O$, and Z is heterocyclyl (e.g., a nitrogen-containing heterocyclyl, e.g., thiomorpholinyl-1,1-dioxide). In some embodiments, the compound of Formula (I-b) is Compound 116.

In some embodiments of Formula (I-b), P is absent, $L^1$ is —$NHCH_2$, $L^2$ is a bond, M is absent, $L^3$ is a bond, and Z is heterocyclyl (e.g., an oxygen-containing heterocyclyl, e.g., tetrahydropyranyl, tetrahydrofuranyl, oxetanyl, or oxiranyl). In some embodiments, the compound of Formula (I-b) is Compound 105.

In some embodiments, the compound is a compound of Formula (I-b-i). In some embodiments of Formula (I-b-i), each of $R^{2a}$ and $R^{2b}$ is independently hydrogen or $CH_3$, each of $R^{2c}$ and $R^{2d}$ is independently hydrogen, m is 1 or 2, n is 1, X is O, p is 0, $M^2$ is phenyl optionally substituted with one or more $R^3$, $R^3$ is —$CF_3$, and $Z^2$ is heterocyclyl (e.g., an oxygen-containing heterocyclyl, e.g., tetrahydropyranyl, tetrahydrofuranyl, oxetanyl, or oxiranyl). In some embodiments, the compound of Formula (I-b-i) is Compound 100, Compound 106, Compound 107, Compound 108, Compound 109, or Compound 111.

In some embodiments, the compound is a compound of Formula (I-b-ii). In some embodiments of Formula (I-b-ii), each of $R^{2a}$, $R^{2b}$, $R^{2c}$, and $R^{2d}$ is independently hydrogen, q is 0, p is 0, m is 1, and $Z^2$ is heterocyclyl (e.g., an oxygen-containing heterocyclyl, e.g., tetrahydropyranyl). In some embodiments, the compound of Formula (I-b-ii) is Compound 100.

In some embodiments, the compound is a compound of Formula (I-c). In some embodiments of Formula (I-c), each of $R^{2c}$ and $R^{2d}$ is independently hydrogen, m is 1, p is 1, q is 0, $R^5$ is —$CH_3$, and Z is heterocyclyl (e.g., a nitrogen-containing heterocyclyl, e.g., piperazinyl). In some embodiments, the compound of Formula (I-c) is Compound 113.

In some embodiments, the compound is a compound of Formula (I-d). In some embodiments of Formula (I-d), each of $R^{2a}$, $R^{2b}$, $R^{2c}$, and $R^{2d}$ is independently hydrogen, m is 1, n is 3, X is O, p is 0, and Z is heterocyclyl (e.g., an oxygen-containing heterocyclyl, e.g., tetrahydropyranyl, tetrahydrofuranyl, oxetanyl, or oxiranyl). In some embodiments, the compound of Formula (I-d) is Compound 110 or Compound 114.

In some embodiments, the compound is a compound of Formula (I-f). In some embodiments of Formula (I-f), each of $R^{2a}$ and $R^{2b}$ is independently hydrogen, n is 1, M is —$CH_2$—, P is a nitrogen-containing heteroaryl (e.g., imidazolyl), $L^3$ is —C(O)$OCH_2$—, and Z is $CH_3$. In some embodiments, the compound of Formula (I-f) is Compound 115.

In some embodiments, the compound is a compound of Formula (II-a). In some embodiments of Formula (II-a), each of $R^{2a}$ and $R^{2b}$ is independently hydrogen, n is 1, q is 0, $L^3$ is —$CH_2$ $(OCH_2CH_2)_2$, and Z is —$OCH_3$. In some embodiments, the compound of Formula (II-a) is Compound 112.

In some embodiments of Formula (II-a), each of $R^{2a}$ and $R^{2b}$ is independently hydrogen, n is 1, $L^3$ is a bond or —$CH_2$, and Z is hydrogen or —OH. In some embodiments, the compound of Formula (II-a) is Compound 103 or Compound 104.

In some embodiments, the compound is a compound of Formula (III). In some embodiments of Formula (III), each of $R^{2a}$, $R^{2b}$, $R^{2c}$, and $R^{2d}$ is independently hydrogen, m is 1, n is 2, q is 3, p is 0, $R^C$ is hydrogen, and $Z^1$ is heteroalkyl optionally substituted with $R^5$ (e.g., —$N(CH_3)(CH_2CH_2)S(O)_2CH_3$). In some embodiments, the compound of Formula (III) is Compound 120.

In some embodiments, the compound is a compound of Formula (III-b). In some embodiments of Formula (III-b), each of $R^{2a}$, $R^{2b}$, $R^{2c}$, and $R^{2d}$ is independently hydrogen, m is 0, n is 2, q is 3, p is 0, and $Z^2$ is aryl (e.g., phenyl) substituted with 1 $R^5$ (e.g., —$NH_2$). In some embodiments, the compound of Formula (III-b) is Compound 102.

In some embodiments, the compound is a compound of Formula (III-b). In some embodiments of Formula (III-b), each of $R^{2a}$, $R^{2b}$, $R^{2c}$, and $R^{2d}$ is independently hydrogen, m is 1, n is 2, q is 3, p is 0, $R^C$ is hydrogen, and $Z^2$ is heterocyclyl (e.g., a nitrogen-containing heterocyclyl, e.g., a nitrogen-containing spiro heterocyclyl, e.g., 2-oxa-7-azaspiro[3.5]nonanyl). In some embodiments, the compound of Formula (III-b) is Compound 121.

In some embodiments, the compound is a compound of Formula (III-d). In some embodiments of Formula (III-d), each of $R^{2a}$, $R^{2b}$, $R^{2c}$, and $R^{2d}$ is independently hydrogen, m is 1, n is 2, q is 1, 2, 3, or 4, p is 0, and X is S $(O)_2$. In some embodiments of Formula (III-d), each of $R^{2a}$ and $R^{2b}$ is independently hydrogen, m is 1, n is 2, q is 1, 2, 3, or 4, p is 0, and X is S $(O)_2$. In some embodiments, the compound of Formula (III-d) is Compound 101, Compound 117, Compound 118, or Compound 119.

In some embodiments, the compound is a compound of Formula (I-b), (I-d), or (I-e). In some embodiments, the compound is a compound of Formula (I-b), (I-d), or (II). In some embodiments, the compound is a compound of Formula (I-b), (I-d), or (I-f). In some embodiments, the compound is a compound of Formula (I-b), (I-d), or (III).

In some embodiments, the compound of Formula (I) is not a compound disclosed in WO2012/112982, WO2012/167223, WO2014/153126, WO2016/019391, WO 2017/075630, US2012-0213708, US 2016-0030359 or US 2016-0030360.

In some embodiments, the compound of Formula (I) comprises a compound shown in Table 4, or a pharmaceutically acceptable salt thereof. In some embodiments, the exterior surface and/or one or more compartments within a device described herein comprises a small molecule compound shown in Table 4, or a pharmaceutically acceptable salt thereof.

TABLE 4
| Compound No. | Structure |
|---|---|
| | Exemplary small molecule compounds |
| 100 | 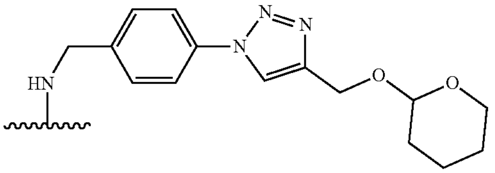 [SMILES: *NCc1ccc(-n2cc(COC3CCCCO3)nn2)cc1] |
| 101 | 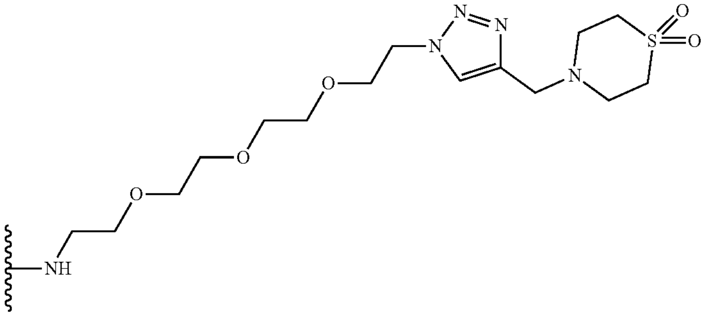 [SMILES: *NCCOCCOCCOCCn1cc(CN2CCS(=O)(=O)CC2)nn1] |
| 102 | 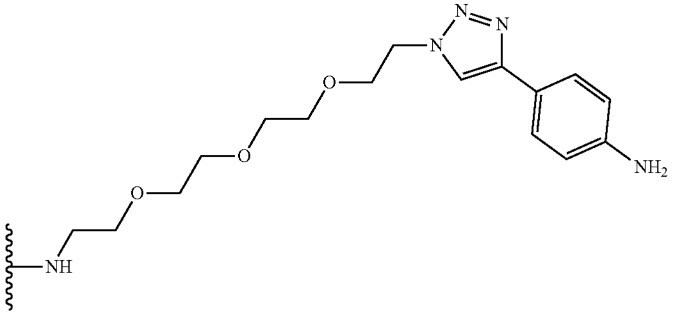 [SMILES: *NCCOCCOCCOCCn1cc(-c2ccc(N)cc2)nn1] |
| 103 | 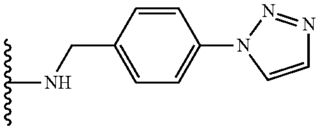 [SMILES: *NCc1ccc(-n2ccnn2)cc1] |
| 104 | 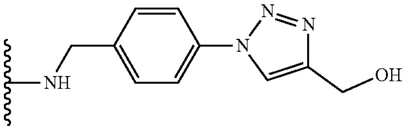 [SMILES: *NCc1ccc(-n2cc(CO)nn2)cc1] |
| 105 | 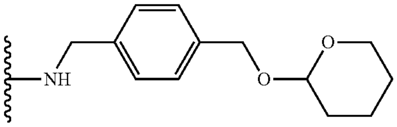 [SMILES: *NCc1ccc(COC2CCCCO2)cc1] |
| 106 | 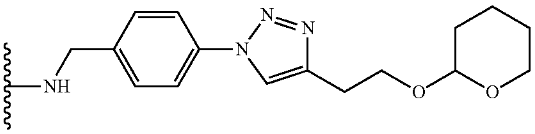 [SMILES: *NCc1ccc(-n2cc(CCOC3CCCCO3)nn2)cc1] |
| 107 | 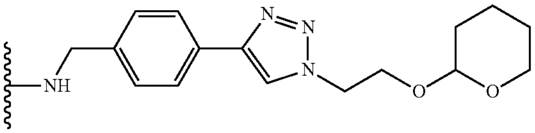 [SMILES: *NCc1ccc(-c2cn(CCOC3CCCCO3)nn2)cc1] |

TABLE 4-continued
| Exemplary small molecule compounds | |
|---|---|
| Compound No. | Structure |
| 108 | 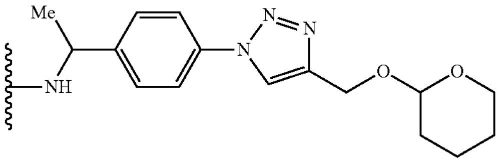 [SMILES: *NC(C)c1ccc(-n2cc(COC3CCCCO3)nn2)cc1] |
| 109 | 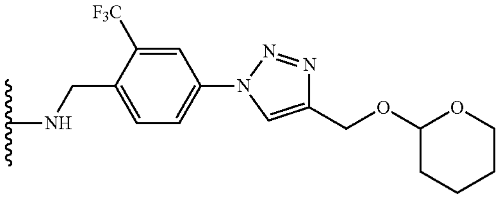 [SMILES: *NCc1ccc(-n2cc(COC3CCCCO3)nn2)cc1C(F)(F)F] |
| 110 | 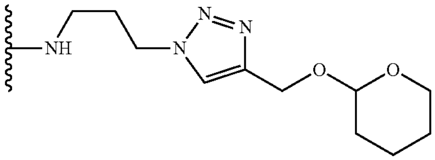 [SMILES: *NCCCn1cc(COC2CCCCO2)nn1] |
| 111 | 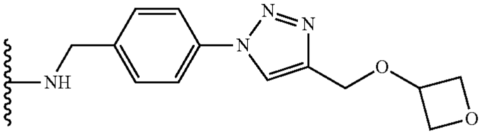 [SMILES: *NCc1ccc(-n2cc(COC3COC3)nn2)cc1] |
| 112 | 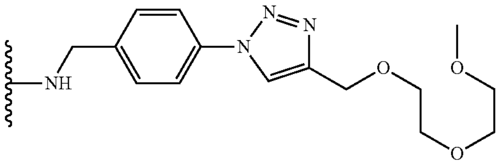 [SMILES: *NCc1ccc(-n2cc(COCCOCCOC)nn2)cc1] |
| 113 | 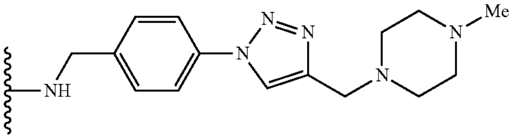 [SMILES: *NCc1ccc(-n2cc(CN3CCN(C)CC3)nn2)cc1] |
| 114 | 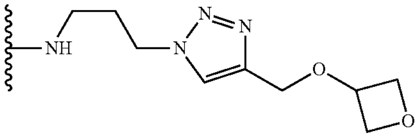 [SMILES: *NCCCn1cc(COC2COC2)nn1] |
| 115 | 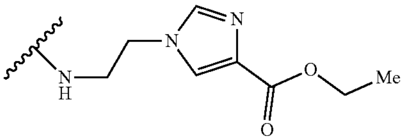 [SMILES: *NCCn1cnc(C(=O)OCC)c1] |
| 116 | 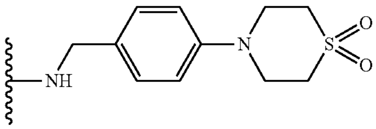 [SMILES: *NCc1ccc(N2CCS(=O)(=O)CC2)cc1] |

TABLE 4-continued

| Exemplary small molecule compounds | |
|---|---|
| Compound No. | Structure |
| 117 | 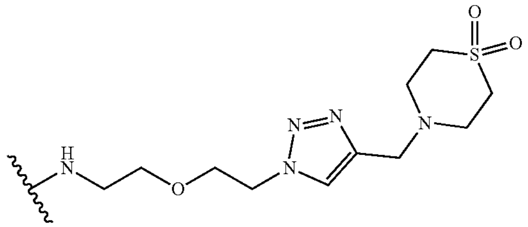 [SMILES: *NCCOCCn1cc(CN2CCS(=O)(=O)CC2)nn1] |
| 118 | 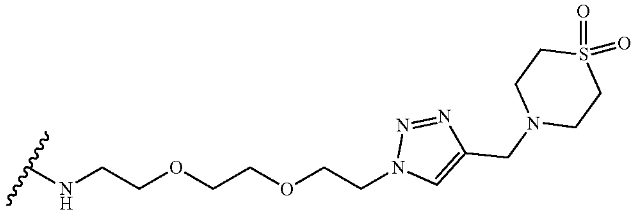 [SMILES: *NCCOCCOCCn1cc(CN2CCS(=O)(=O)CC2)nn1] |
| 119 | 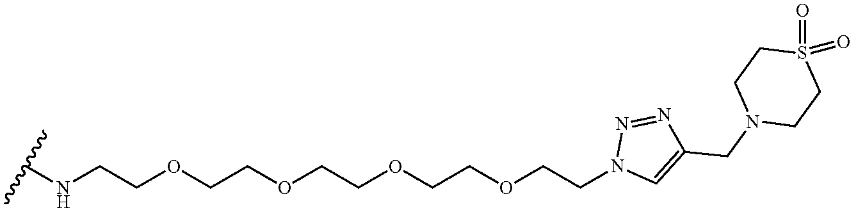 [SMILES: *NCCOCCOCCOCCOCCn1cc(CN2CCS(=O)(=O)CC2)nn1] |
| 120 | 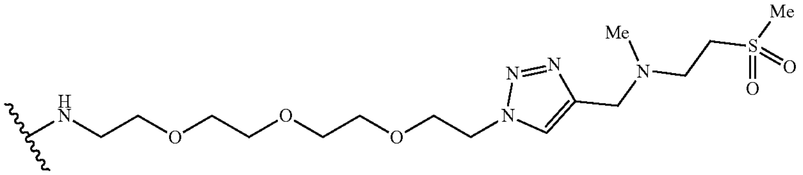 [SMILES: *NCCOCCOCCOCCn1cc(CN(C)CCS(C)(=O)=O)nn1] |
| 121 | 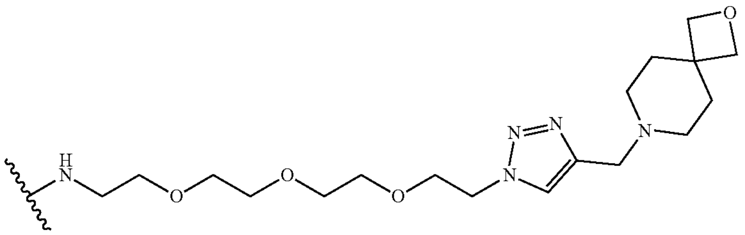 [SMILES: *NCCOCCOCCOCCn1cc(CN2CCC3(CC2)COC3)nn1] |

Conjugation of any of the compounds in Table 4 to a polymer (e.g., an alginate) may be performed as described in Example 2 of WO 2019/195055 or any other suitable chemical reaction.

In some embodiments, the compound is a compound of Formula (I) (e.g., Formulas (I-a), (I-b), (I-c), (I-d), (I-e), (I-f), (II), (II-a), (II), (III-a), (III-b), (II-c), or (III-d)), or a pharmaceutically acceptable salt thereof and is selected from:

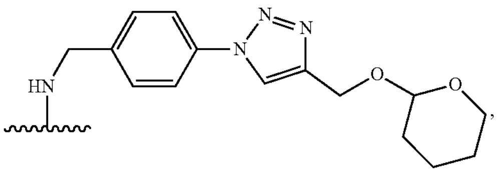

,

-continued

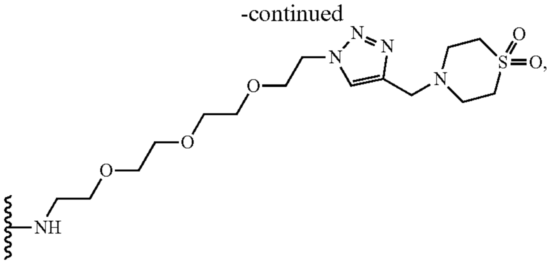

, and

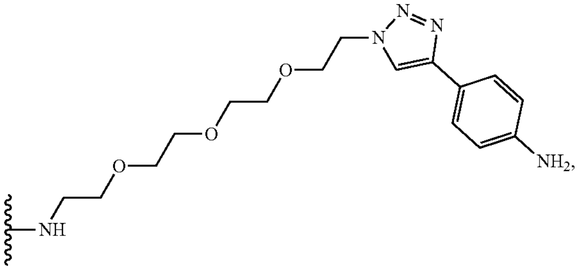

, or a pharmaceutically acceptable salt thereof.

In some embodiments, the device described herein comprises the compound of

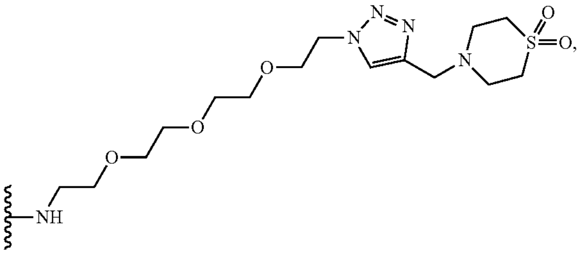

,

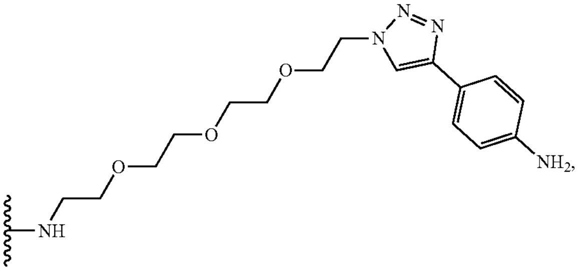

, or a pharmaceutically acceptable salt of either compound.

In some embodiments, a compound of Formula (I) (e.g., Compound 101 in Table 4) is covalently attached to an alginate (e.g., an alginate with approximate MW<75 kDa, G: M ratio ≥1.5) at a conjugation density of at least 2.0% and less than 9.0%, or 3.0% to 8.0%, 4.0-7.0, 5.0 to 7.0, or 6.0 to 7.0 or about 6.8 as determined by combustion analysis for percent nitrogen as described in WO 2020/069429.

Preparation of Two-Compartment Hydrogel Capsules

Each compartment of a device described herein may comprise an unmodified polymer, a polymer modified with a compound of Formula (I), or a blend thereof. Briefly, to prepare a device configured as a two-compartment hydrogel capsule, a volume of a first polymer solution (e.g., comprising an unmodified polymer, a polymer modified with a compound of Formula (I), or a blend thereof, and optionally containing cells,) is loaded into a first syringe connected to the inner lumen of a coaxial needle. The first syringe may then be connected to a syringe pump oriented vertically above a vessel containing an aqueous cross-linking solution which comprises a cross-linking agent, a buffer, and an osmolarity-adjusting agent. A volume of the second polymer solution (e.g., comprising an unmodified polymer, a polymer modified with a compound of Formula (I), or a blend thereof, and optionally containing cells) is loaded into a second syringe connected to the outer lumen of the coaxial needle. The second syringe may then be connected to a syringe pump oriented horizontally with respect to the vessel containing the cross-linking solution. A high voltage power generator may then be connected to the top and bottom of the needle. The syringe pumps and power generator can then be used to extrude the first and second polymer solutions through the syringes with settings determined to achieve a desired droplet rate of polymer solution into the cross-linking solution. The skilled artisan may readily determine various combinations of needle lumen sizes, voltage range, flow rates, droplet rate and drop distance to create 2-compartment hydrogel capsule compositions in which the majority (e.g., at least 80%, 85%, 90% or more) of the capsules are within 10% of the target size and desired shape. After exhausting the first and second volumes of polymer solution, the droplets may be allowed to cross-link in the cross-linking solution for certain amount of time, e.g., about five minutes.

An exemplary process for preparing a composition of millicapsules (e.g., 1.5 mm diameter) is described in WO 2019/195055.

ENUMERATED EMBODIMENTS

1. An implantable device for inducing a protective immune response to an infectious agent, the device comprising a first antigen-expressing cell that is engineered to express and secrete one or more antigens of the infectious agent, wherein the device is configured to exhibit one or more of following properties when implanted into a subject:
(a) immune cells do not contact the antigen-expressing cell;
(b) the first antigen-expressing cell does not exit the device; and
(c) the antigen of the infection agent is secreted to the subject in an amount and for an antigen-delivery time period effective to elicit the protective immune response in the subject; and wherein the device comprises one or more of the following features:
(i) the first antigen-expressing cell is engineered to express and secrete at least two, three or more different antigens of the infectious agent;
(ii) the device comprises a second antigen-expressing cell that is engineered to express and secrete at least one antigen of the infectious agent that is different than each antigen secreted by the first antigen-expressing cell;
(iii) the device comprises a third antigen-expressing cell that is engineered to express and secrete at least one antigen of the infectious agent that is different than each antigen secreted by the first antigen-expressing cell and the second antigen-expressing cell;
(iv) the device is configured to continuously deliver to the subject throughout the antigen-delivery time period at least one immunomodulatory agent that enhances the protective immune response to the infectious agent, wherein the immunomodulatory agent is expressed and secreted by any of the antigen-expressing cells or by a different cell;

(v) the device comprises an ARPE-19 cell that endogenously expresses and secretes interleukin-6 and monocyte chemoattractant protein (MCP-1), wherein the ARPE-19 cell is the same or different than the first antigen-expressing cell;

(vi) at least one of the antigens expressed by the first antigen-expressing cell comprises a secretory signal peptide sequence of MGWRAAGALLLALLLHGRLLA (SEQ ID NO:1);

(vii) a compound or polymer disposed on the surface of the device that mitigates the foreign body response (FBR) to the device; and (viii) the surface of the device does not contain alginate.

2. The device of embodiment 1, wherein the antigen-delivery time period is at least any of 1 week, 2 weeks, 4 weeks, 8 weeks, 16 weeks or 32 weeks, and optionally the antigen-delivery time period is no longer than 52 weeks or 48 weeks.
3. The implantable device of any one of embodiments 1 or 2, wherein the protective immune response comprises one or more of (i) production of neutralizing antibodies (NAbs) of at least two antibody isotypes, (ii) production of follicular helper T ($T_{FH}$) cells specific for the antigen and (iii) production of cytotoxic CD8 positive cells specific for the antigen.
4. The implantable device of any one of embodiments 1 to 3, which comprises one or more of features (i), feature (ii) and feature (iii).
5. The implantable device of any one of embodiments 1 to 4, which comprises feature (iv), wherein delivery of the immunomodulatory agent promotes one of more of the following immune responses: generation of $T_{FH}$ cells, generation of memory B cells, differentiation of antibody secreting cells into long-lived plasma cells.
6. The implantable device of embodiment 5, wherein the immunomodulatory agent is interleukin-6 (IL-6), monocyte chemoattractant protein (MCP-1), interleukin-21 (IL-21), interleukin-4 (IL-4), interleukin-5 (IL-5), interleukin-10 (IL-10), interleukin-13 (IL-13), secondary lymphoid-tissue chemokine (SLC), B cell activating Factor (BAFF), anti-CTLA4, anti-PD1, anti-PDL1, or anti-PDL2.
7. The implantable device of any one of embodiments 1 to 6, which comprises feature (v).
8. The implantable device of any one of embodiments 1 to 7, which comprises feature (vi).
9. The implantable device of any one of embodiments 1 to 8, which comprises feature (vii).
10. The implantable device of any one of embodiments 1 to 3, which comprises feature (v) and feature (vii).
11. The implantable device of any one of embodiments 1 to 3, which comprises feature (i), feature (v) and feature (vii).
12. The implantable device of any one of embodiments 1 to 3, which comprises feature (v) and feature (vi).
13. The implantable device of any one of embodiments 1 to 12, wherein expression of each antigen is regulated by a controllable expression system.
14. The device of any one of embodiments 1 to 13, which comprises feature (iv) and expression of each immunomodulatory agent is regulated by a controllable system.
15. The device of embodiment 13 or 14, wherein the controllable expression system comprises an inducible promoter.
16. The device of any one of embodiments 1 to 15, wherein the infectious agent is a virus, a bacteria or a parasite.
17. The device of embodiment 16, wherein the infectious agent is a virus.
18. The device of embodiment 17, wherein the infectious agent is a coronavirus (e.g., severe acute respiratory syndrome coronavirus 2 (SARS-COV-2), SARS-associated coronavirus (SARS-CoV), MERS-associated coronavirus)), a Human Immunodeficiency Virus (HIV), an Epstein Barr Virus (EBV) or a Respiratory Syncytial Virus (RSV).
19. The device of embodiment 18, wherein the virus is SARS-COV-2 and the first antigen-expressing cell is engineered to secrete one, two or more of the antigens shown in FIGS. 1A-1G.
20. The device of any one of embodiments 18-19, wherein the antigen comprises the SARS-CoV-2 surface glycoprotein.
21. The device of any one of embodiments 18-20, wherein the antigen has about 80%, 85%, 90%, 91%, 92%, 93%, 94%, 95%, 96%, 97%, 98%, 99% sequence identity to SEQ ID NO: 2. 22. The device of any one of embodiments 18-21, wherein the antigen comprises the sequence of SEQ ID NO: 2.
23. The device of embodiment 18, wherein the virus is an HIV and the first antigen-expressing cell is engineered to secrete one, two or more of the antigens shown in FIGS. 2A-2M.
24. The device of any one of embodiment 18 or embodiment 23, wherein the antigen comprises BG505 Olio6.CD4KO.
25. The device of any one of embodiment 18 or embodiments 23-24, wherein the antigen has about 80%, 85%, 90%, 91%, 92%, 93%, 94%, 95%, 96%, 97%, 98%, 99% sequence identity to SEQ ID NO: 21.
26. The device of any one of embodiment 18 or embodiments 23-25, wherein the antigen comprises the sequence of SEQ ID NO: 21.
27. The device of embodiment 18, wherein the virus is an EBV, and the first antigen-expressing cell is engineered to secrete one, two or more of the antigens shown in FIGS. 3A-3C.
28. The device of embodiment 18, wherein the virus is an RSV, and the first antigen-expressing cell is engineered to secrete one, two or more of the antigens shown in FIGS. 4A-4C.
29. The device of any one of embodiment 18 or embodiment 28, wherein the antigen comprises fusion glycoprotein F0.
30. The device of any one of embodiment 18 or embodiments 28-29, wherein the antigen has about 80%, 85%, 90%, 91%, 92%, 93%, 94%, 95%, 96%, 97%, 98%, 99% sequence identity to SEQ ID NO: 27.
31. The device of any one of embodiment 18 or embodiments 28-30, wherein the antigen comprises the sequence of SEQ ID NO: 27.
32. The device of any one of embodiments 1 to 31, wherein the device is configured to continuously deliver one or more cell-secreted antigens of at least one additional infectious agent.
33. The device of any one of embodiments 1 to 32, wherein each antigen-expressing cell and each immunomodulatory agent is contained in a cell-containing compartment surrounded by a barrier compartment.

34. The device of embodiment 33, wherein the barrier compartment comprises a hydrogel-forming polymer, e.g., an alginate.

35. The device of embodiment 33 or embodiment 34, wherein the cell-containing compartment comprises a hydrogel-forming polymer, e.g., an alginate.

36. The device of any one of embodiments 1 to 35, which comprises two or more compartments that contain antigen-expressing cells.

37. The device of any one of embodiments 1 to 36, which comprises feature (vii) and the FBR-mitigating compound is a compound of Formula (I):

(I)

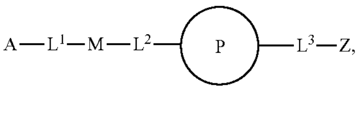

or a pharmaceutically acceptable salt thereof, wherein:

A is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O), —C(O)N($R^C$)—, —N($R^C$)C(O)($C_1$-$C_6$-alkylene)-, —N($R^C$)C(O)($C_1$-$C_6$-alkenylene)-, —N($R^C$)N($R^D$)—, —NCN—, —C(=N($R^C$)($R^D$))O—, —S—, —S(O)—, —OS(O)—, —N(R)S(O)—, —S(O), N($R^C$)—, —P($R^F$)$_y$—, —Si($OR^A$)$_2$—, —Si($R^G$)($OR^A$)—, —B($OR^A$)—, or a metal, each of which is optionally linked to an attachment group (e.g., an attachment group described herein) and is optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond;

M is absent, alkyl, heteroalkyl, cycloalkyl, heterocyclyl, aryl, or heteroaryl, each of which is optionally substituted by one or more $R^3$;

P is absent, cycloalkyl, heterocyclyl, or heteroaryl, each of which is optionally substituted by one or more $R^4$;

Z is hydrogen, alkyl, alkenyl, alkynyl, heteroalkyl, —$OR^A$, C(O)$R^A$, —C(O)$OR^A$, —C(O)N($R^C$)($R^D$), —N($R^C$)C(O)$R^A$, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted by one or more $R^5$;

each $R^A$, $R^B$, $R^C$, $R^D$, $R^E$, $R^E$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring (e.g., a 5-7 membered ring), optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), $SR^{E1}$, S(O)$_x$$R^{E1}$, —OS(O)$_x$$R^{E1}$, —N($R^{C1}$)S(O)$_x$ $R^{E1}$, —S(O)$_x$N($R^{C1}$)($R^{D1}$), —P($R^{F1}$)$_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

38. The device of embodiment 37, wherein the FBR-mitigating compound is selected from the compounds shown in Table 4, or a pharmaceutically acceptable salt thereof.

39 The device of embodiment 38, wherein the FBR-mitigating compound is:

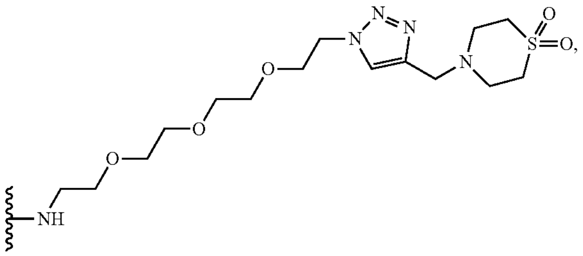 [SMILES: *NCCOCCOCCOCCn1cc(CN2CCS(=O)(=O)CC2)nn1]

or a pharmaceutically acceptable salt thereof.

40. The device of embodiment 38, wherein the FBR-mitigating compound is

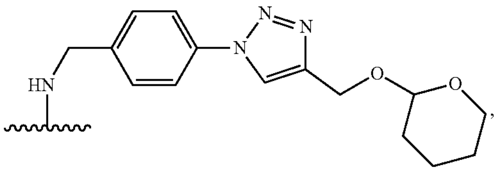 [SMILES: *NCc1ccc(-n2cc(COC3CCCCO3)nn2)cc1]

or a pharmaceutically acceptable salt thereof.

41. A hydrogel capsule comprising:

(a) a cell-containing compartment which comprises cells (e.g., living cells) encapsulated in a first polymer composition, wherein at least a portion of the cells are engineered to continuously express and secrete a first antigen of an infectious agent; and (b) a barrier compartment surrounding the cell-binding compartment and comprising a second polymer composition which comprises an alginate covalently modified with at least one compound selected from the group consisting of Compound 100, Compound 101, Compound 110, Compound 112, Compound 113 and Compound 114 shown in Table 4 above, or a pharmaceutically acceptable salt of the compound, wherein the hydrogel capsule has a spherical shape and has a diameter of 0.5 millimeter to 5 millimeters.

42. The hydrogel capsule of embodiment 41, wherein the barrier compartment comprises an alginate covalently modified with

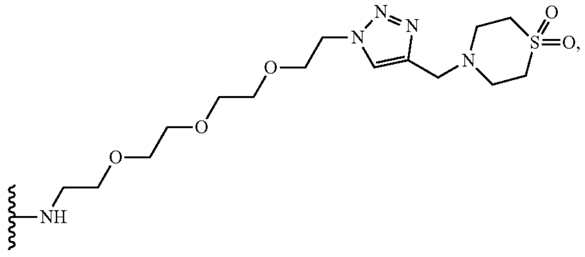 [SMILES: *NCCOCCOCCOCCn1cc(CN2CCS(=O)(=O)CC2)nn1]

or a pharmaceutically acceptable salt thereof.

43. The hydrogel capsule of embodiment 40 or embodiment 41, wherein the barrier compartment has an average thickness of about 10 to about 300 microns, about 20 to about 150 microns, or about 40 to about 75 microns.

44. The hydrogel capsule of any one of embodiments 40 to 43, wherein the barrier compartment further comprises an unmodified alginate.

45. The hydrogel capsules of any one of embodiments 40-44, wherein at least a portion of the cells are engineered to continuously express and secrete a second antigen for the infectious agent, optionally wherein the first and second antigens are expressed and secreted by the same cells.

46. The hydrogel capsule of any one of embodiments 40-45, wherein at least a portion of the cells are engineered to continuously express and secrete a third antigen for the infectious agent, optionally wherein two or more of the first, second and third antigens are expressed and secreted by the same cells.

47. The hydrogel capsule of any one of embodiments 40-46, wherein at least a portion of the cells express and secrete at least one immunomodulatory agent that enhances the immune response to the infectious agent when the capsule is implanted into a subject.

48. The hydrogel capsule of embodiment 47, wherein each antigen and each immunomodulatory agent are expressed and secreted by the same cells.

49. The hydrogel capsule of any one of embodiments 40-48, wherein the cells comprise a regulatable expression system capable of regulating one or both of antigen expression and immunomodulatory agent expression in response to one or more exogenous signals.

50. The hydrogel capsule of any one of embodiments 40-49, wherein all of the cells are ARPE-19 cells that endogenously express IL-6 and MCP-1.

51. A vaccine composition comprising a preparation of hydrogel capsules and a pharmaceutically acceptable excipient, wherein each hydrogel capsule in the preparation is a hydrogel capsule as defined in any of embodiments 40-50.

52. The vaccine composition of embodiment 51, which has a volume of less than 10 milliliters, optionally less than 8 ml, or less than 5 ml.

53. A method of inducing a neutralizing antibody (NAb) response to an infectious agent comprising implanting into a subject the device of any one of embodiments 1 to 39, the hydrogel capsule of any one of embodiments 40-51 or the vaccine composition of embodiments 51-52.

54. The method of embodiment 53, wherein the device, capsule or vaccine composition is implanted by subcutaneous injection.

55. The method of embodiment 53, wherein the device, capsule or vaccine composition is implanted into the peritoneal cavity of the subject.

EXAMPLES

In order that the disclosure described herein may be more fully understood, the following examples are set forth. The examples described in this application are offered to illustrate the implantable devices, and compositions and methods provided herein and are not to be construed in any way as limiting their scope.

Figure 5B:
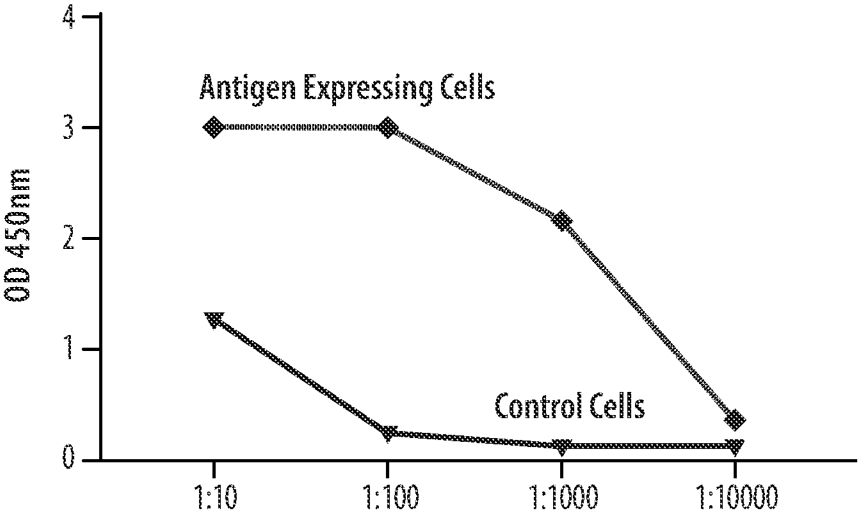

Example 1. Generation of Antibody Response to Model Antigen Delivered by Implanted Capsules Containing Antigen-Expressing Cells Antigen-producing capsules and control capsules were generated by encapsulating (i) ARPE-19 cells engineered to express a model antigen (a human protein) or (ii) normal (i.e., parental) ARPE-19 cells in the inner compartment of two-compartment hydrogel capsules. The alginate solution used to form the inner compartment of the capsules contained about 20 million cells/mL. The alginate solution used to form the outer compartment of the capsules contained a mixture of an unmodified alginate and an alginate chemically-modified with Compound 101 in Table 4. Two groups of four C57BL/6 mice were implanted with about 0.250 mL of the antigen-producing capsules or the control capsules. An Elisa assay was used to quantitate the amount of antigen-specific IgG antibodies in serial dilutions of plasma samples retrieved at 3 weeks and 7 weeks post-implantation. The results are shown in FIG. 5.

Equivalents and Scope

This application refers to various issued patents, published patent applications, journal articles, and other publications, all of which are incorporated herein by reference in their entirety. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, Figures, or Examples but rather is as set forth in the appended claims. Those of ordinary skill in the art will appreciate that various changes and modifications to this description may be made without departing from the spirit or scope of the present disclosure, as defined in the following claims.

The invention claimed is:

1. An implantable device for inducing a protective immune response to an infectious agent, the device comprising a first antigen-expressing cell that is engineered to express and secrete a first antigen of the infectious agent, wherein the device is configured to exhibit the following properties when implanted into a subject:

(a) an immune cell of the subject does not contact the first antigen-expressing cell;

(b) the first antigen-expressing cell does not exit the device; and (c) continuous delivery of the first antigen to the subject in an amount and for a time period effective to elicit the protective immune response, and wherein the device comprises at least one of the following features:

(i) the first antigen-expressing cell is engineered to express and secrete at least two, three or more different antigens of the infectious agent;

(ii) the device comprises a second antigen-expressing cell that is engineered to express and secrete a second antigen of the infectious agent;

(iii) the device comprises a third antigen-expressing cell that is engineered to express and secrete a third antigen of the infectious agent that is different than each antigen secreted by the first antigen-expressing cell and the antigen-expressing second cell;

(iv) the device is configured to deliver to the subject an immunomodulatory agent that enhances the protective immune response to the infectious agent;

(v) the first antigen comprises a secretory signal peptide sequence of MGWRAAGALLLALLLHGRLLA (SEQ ID NO: 1);

(vi) a foreign body response (FBR) mitigating compound is disposed on the surface of the device; and, (vii) the surface of the device does not contain alginate.

2. The device of claim 1, wherein the time period is greater than 1 week.

3. The implantable device of claim 1, wherein the protective immune response comprises one or more of (i) production of neutralizing antibodies (NAbs) of at least two antibody isotypes, (ii) production of follicular helper T ($T_{FH}$) cells specific for the antigen and (iii) production of cytotoxic CD8 positive cells specific for the antigen.

4. The implantable device of claim 1, which comprises one or more of features (i), feature (ii) and feature (iii).

5. The implantable device of claim 1, which comprises feature (iv), wherein delivery of the immunomodulatory agent promotes one of more of the following immune responses: generation of $T_{FH}$ cells, generation of memory B cells, differentiation of antibody secreting cells into long-lived plasma cells.

6. The implantable device of claim 1, wherein the immunomodulatory agent is interleukin-6 (IL-6), monocyte chemoattractant protein (MCP-1), interleukin-21 (IL-21), interleukin-4 (IL-4), interleukin-5 (IL-5), interleukin-10 (IL-10), interleukin-13 (IL-13), secondary lymphoid-tissue chemokine (SLC), B cell activating Factor (BAFF), anti-CTLA4, anti-PD1, anti-PDL1, or anti-PDL2.

7. The implantable device of claim 1, which comprises feature (v) or (vi) or (vii).

8. The implantable device of claim 1, wherein expression of the first antigen is regulated by a controllable expression system.

9. The device of claim 1, which comprises feature (iv) and expression of the immunomodulatory agent is regulated by a controllable system.

10. The device of claim 1, wherein the infectious agent is a virus, a bacterium or a parasite.

11. The device of claim 10, wherein the infectious agent is a virus selected from the group consisting of a severe acute respiratory syndrome coronavirus 2 (SARS-COV-2), SARS-associated coronavirus (SARS-COV), MERS-associated coronavirus, a Human Immunodeficiency Virus (HIV), an Epstein Barr Virus (EBV) and a Respiratory Syncytial Virus (RSV).

12. The device of claim 1, wherein the first antigen producing cell and immunomodulatory agent is contained in a cell-containing compartment surrounded by a barrier compartment.

13. The device of claim 12, wherein the barrier compartment comprises a hydrogel-forming polymer and the cell-containing compartment comprises a hydrogel-forming polymer.

14. The device of claim 1, which comprises feature (vi) and the FBR-mitigating compound is a compound of Formula (I):

(I)

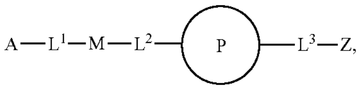

or a pharmaceutically acceptable salt thereof, wherein:

A is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)C(O)($C_1$-$C_6$-alkylene)-, —N($R^C$)C(O)($C_1$-$C_6$-alkenylene)-, —N($R^C$)N($R^D$)—, —NCN—, —C(=N($R^C$)($R^D$))O—, —S—, —S(O)$_x$—, —OS(O)—, —N($R^C$)S(O)—, —S(O)$_x$N($R^C$)—, —P($R^F$)$_y$—, —Si(O$R^A$)$_2$—, —Si($R^G$)(O$R^A$)—, —B(O$R^A$)—, or a metal, each of which is optionally linked to an attachment group and is optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond;

M is absent, alkyl, heteroalkyl, cycloalkyl, heterocyclyl, aryl, or heteroaryl, each of which is optionally substituted by one or more $R^3$;

P is absent, cycloalkyl, heterocyclyl, or heteroaryl, each of which is optionally substituted by one or more $R^4$;

Z is hydrogen, alkyl, alkenyl, alkynyl, heteroalkyl, —O$R^A$, —C(O)$R^A$, C(O)O$R^A$, C(O)N($R^C$)($R^D$), —N($R^C$)C(O)$R^A$, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring, optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —O$R^{A1}$, —C(O)O$R^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), S$R^{E1}$, S(O)$_x$$R^{E1}$, —OS(O)$_x$$R^{E1}$, —N($R^{C1}$)S(O)$_x$$R^{E1}$, —S(O)$_x$N($R^{C1}$)($R^{D1}$), —P($R^{F1}$)$_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

15. The device of claim 14, wherein the FBR-mitigating compound is selected from

| Compound No. | Structure |
|---|---|
| 100 | 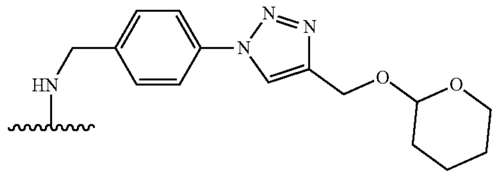 [SMILES: *NCc1ccc(-n2cc(COC3CCCCO3)nn2)cc1] |

-continued
| Compound No. | Structure |
|---|---|
| 101 | 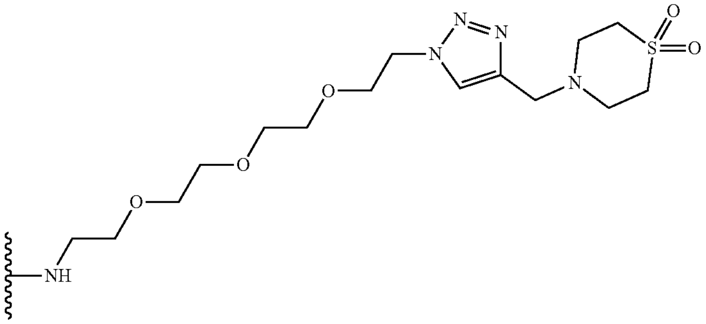 [SMILES: *NCCOCCOCCOCCn1cc(CN2CCS(=O)(=O)CC2)nn1] |
| 102 | 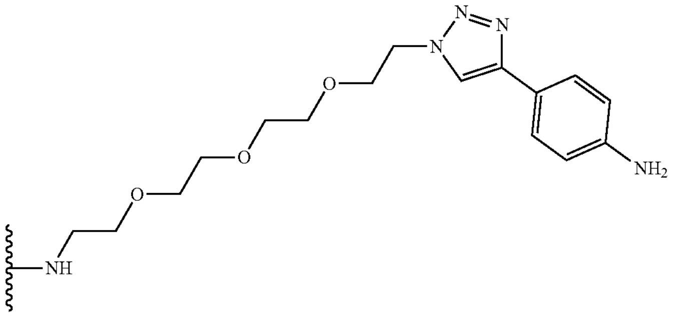 [SMILES: *NCCOCCOCCOCCn1cc(-c2ccc(N)cc2)nn1] |
| 103 | 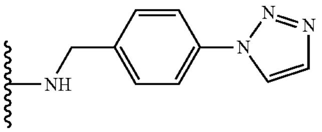 [SMILES: *NCc1ccc(-n2ccnn2)cc1] |
| 104 | 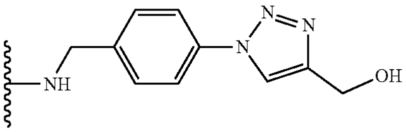 [SMILES: *NCc1ccc(-n2cc(CO)nn2)cc1] |
| 105 | 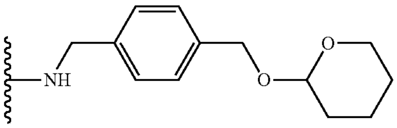 [SMILES: *NCc1ccc(COC2CCCCO2)cc1] |
| 106 | 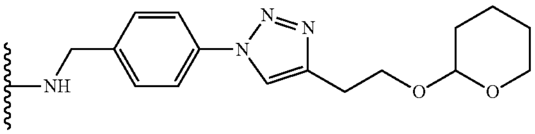 [SMILES: *NCc1ccc(-n2cc(CCOC3CCCCO3)nn2)cc1] |
| 107 | 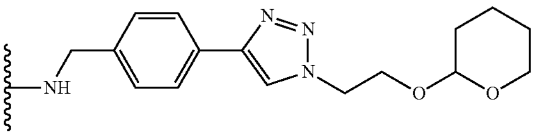 [SMILES: *NCc1ccc(-c2cn(CCOC3CCCCO3)nn2)cc1] |
| 108 | 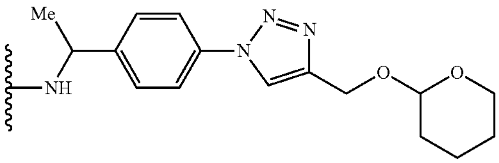 [SMILES: *NC(C)c1ccc(-n2cc(COC3CCCCO3)nn2)cc1] |

-continued
| Compound No. | Structure |
|---|---|
| 109 | 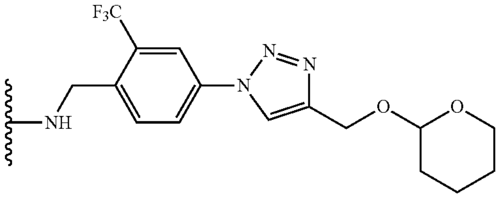 [SMILES: *NCc1ccc(-n2cc(COC3CCCCO3)nn2)cc1C(F)(F)F] |
| 110 | 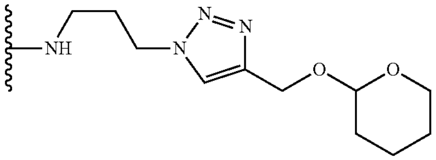 [SMILES: *NCCCn1cc(COC2CCCCO2)nn1] |
| 111 | 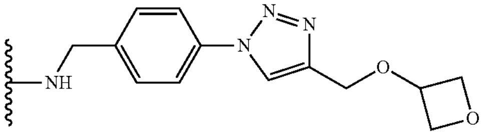 [SMILES: *NCc1ccc(-n2cc(COC3COC3)nn2)cc1] |
| 112 | 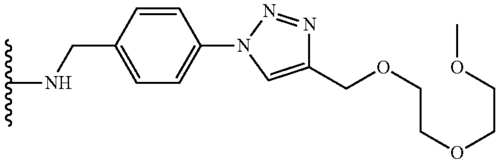 [SMILES: *NCc1ccc(-n2cc(COCCOCCOC)nn2)cc1] |
| 113 | 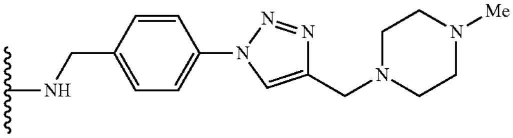 [SMILES: *NCc1ccc(-n2cc(CN3CCN(C)CC3)nn2)cc1] |
| 114 | 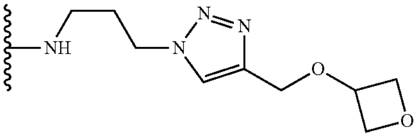 [SMILES: *NCCCn1cc(COC2COC2)nn1] |
| 115 | 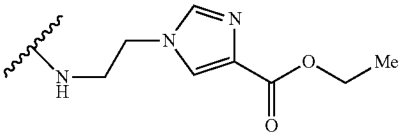 [SMILES: *NCCn1cnc(C(=O)OCC)c1] |
| 116 | 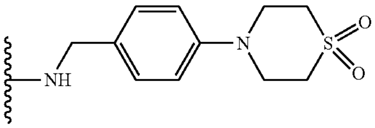 [SMILES: *NCc1ccc(N2CCS(=O)(=O)CC2)cc1] |
| 117 | 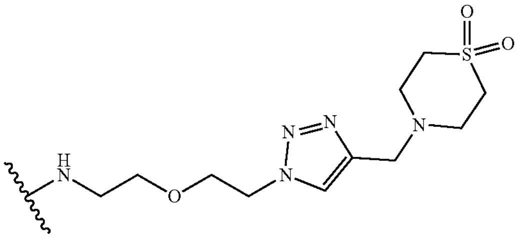 [SMILES: *NCCOCCn1cc(CN2CCS(=O)(=O)CC2)nn1] |

-continued

| Compound No. | Structure |
|---|---|
| 118 | 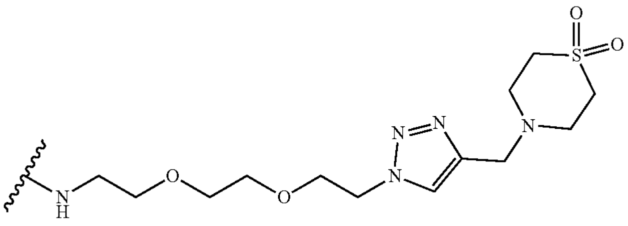 [SMILES: *NCCOCCOCCn1cc(CN2CCS(=O)(=O)CC2)nn1] |
| 119 | 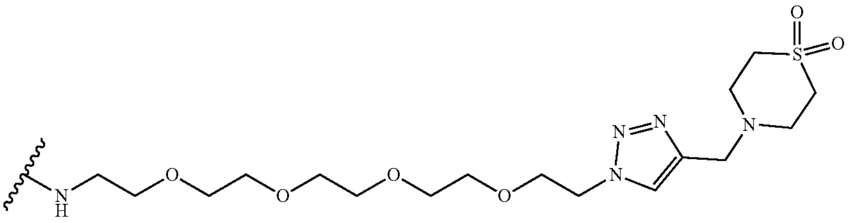 [SMILES: *NCCOCCOCCOCCOCCn1cc(CN2CCS(=O)(=O)CC2)nn1] |
| 120 | 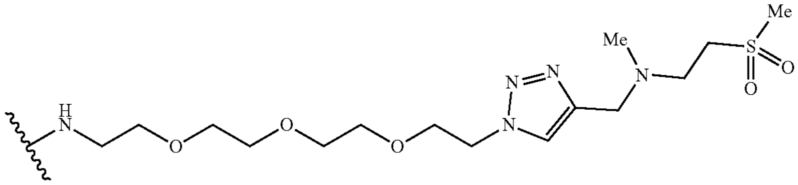 [SMILES: *NCCOCCOCCOCCn1cc(CN(C)CCS(C)(=O)=O)nn1] |
| 121 | 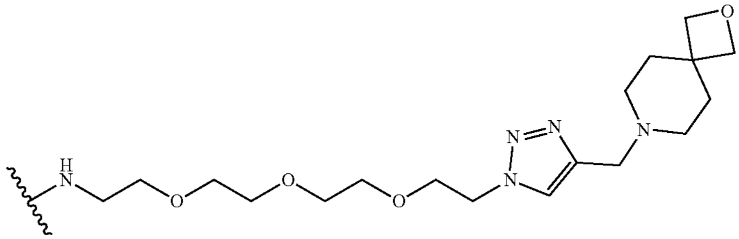, |

or a pharmaceutically acceptable salt thereof.

16. A hydrogel capsule comprising:

(a) a cell-containing compartment which comprises living cells encapsulated in a first polymer composition, wherein the living cells are engineered to continuously express and secrete a first antigen of an infectious agent; and (b) a barrier compartment surrounding the cell-containing compartment and comprising a second polymer composition which comprises an alginate covalently modified with a compound selected from the group consisting of

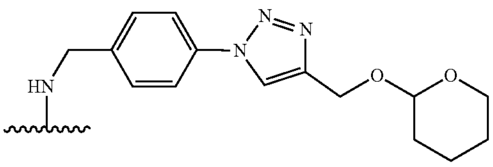

-continued

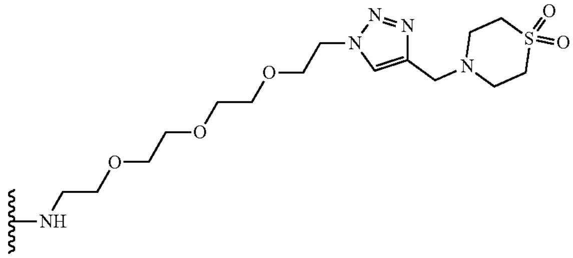

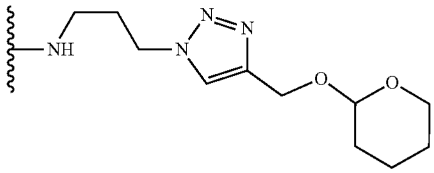

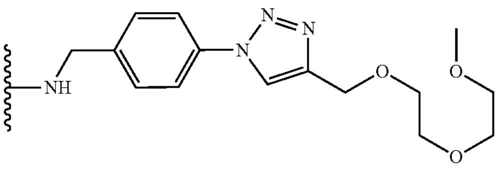

-continued

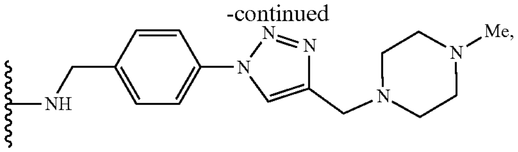

and

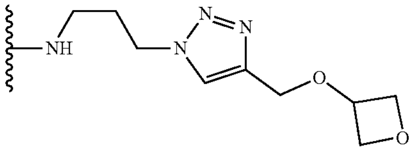

or a pharmaceutically acceptable salt of the compound, wherein the hydrogel capsule has a spherical shape and has a diameter of 0.5 millimeter to 5 millimeters.

17. The hydrogel capsule of claim 16, wherein the barrier compartment has an average thickness of about 10 to about 300 microns, about 20 to about 150 microns, or about 40 to about 75 microns.

18. The hydrogel capsules of claim 16, wherein the living cells are engineered to continuously express and secrete a second antigen for the infectious agent.

19. A vaccine composition comprising a preparation of hydrogel capsules and a pharmaceutically acceptable excipient, wherein each hydrogel capsule in the preparation is a hydrogel capsule of claim 16.

20. The vaccine composition of claim 19, which has a volume of less than 10 milliliters,.

21. A method of inducing a neutralizing antibody (NAb) response to an infectious agent comprising implanting into a subject a device comprising a first antigen-expressing cell that is engineered to express and secrete a first antigen of the infectious agent, wherein the device is configured to exhibit the following properties when implanted into a subject:

(a) an immune cell of the subject does not contact the first antigen-expressing cell;

(b) the first antigen-expressing cell does not exit the device; and (c) delivery of the first secreted antigen to the subject in an amount and for a time period effective to elicit the protective immune response, and wherein the device comprises at least one of the following features;

(i) the device comprises a second antigen-expressing cell that is engineered to express and secrete a second antigen of the infectious agent;

(ii) the device comprises a third antigen-expressing cell that is engineered to express and secrete a third antigen of the infectious agent;

(iii) the device is configured to continuously deliver to the subject throughout the time period an immunomodulatory agent that enhances the protective immune response to the infectious agent;

(iv) the first secreted antigen comprises a secretory signal peptide sequence of MGWRAAGALLLALLLHGRLLA (SEQ ID NO:1);

(v) a compound or polymer disposed on the surface of the device that mitigates the foreign body response (FBR) to the device; and (vi) the surface of the device does not contain alginate.

22. The method of claim 21, wherein the device, capsule or vaccine composition is implanted by sub-cutaneous injection, or is implanted into the peritoneal cavity of the subject.

* * * * *